US007563448B2

(12) United States Patent
Ellenhorn et al.

(10) Patent No.: US 7,563,448 B2
(45) Date of Patent: Jul. 21, 2009

(54) MODIFIED VACCINIA ANKARA EXPRESSING P53 IN CANCER IMMUNOTHERAPY

(75) Inventors: Joshua D.I. Ellenhorn, Beverly Hills, CA (US); Don J. Diamond, Glendora, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 11/805,180

(22) Filed: May 21, 2007

(65) Prior Publication Data

US 2007/0224195 A1 Sep. 27, 2007

Related U.S. Application Data

(62) Division of application No. 10/746,558, filed on Dec. 23, 2003, now Pat. No. 7,256,037.

(60) Provisional application No. 60/436,268, filed on Dec. 23, 2002, provisional application No. 60/466,607, filed on Apr. 30, 2003.

(51) Int. Cl.
*A61K 39/12* (2006.01)
(52) U.S. Cl. ............. 424/199.1; 424/204.1; 424/205.1; 424/232.1; 424/277.1
(58) Field of Classification Search ........................ None
See application file for complete search history.

(56) References Cited

U.S. PATENT DOCUMENTS

| | | | |
|---|---|---|---|
| 5,185,146 | A | 2/1993 | Alternburger |
| 6,045,802 | A | 4/2000 | Schlom |
| 6,410,010 | B1 | 6/2002 | Zhang |

FOREIGN PATENT DOCUMENTS

WO WO 2004/074493 A 9/2004

OTHER PUBLICATIONS

Ashur-Fabian et al (PNAS, 2004, 101:12236-12241).*
Bhaskaran et al (Environmental and Molecular Mutagenesis, 1999, 33:177-184).*
Ober et al (Journal of Virology, Aug. 2002, 76:7713-7723).*
Hernandez et al (J of Immunology, 2001, 166:3908-3914).*
Oxenius et al (J of Virology, 1999, 73:4120-4126).*
Allred, D.C., et al., "Biomarkers in early breach neoplasia," *J. Cell Biochem Suppl* 1993; 17G:125-131.
Antoine, G., et al., "The complete genomic sequence of the modified vaccinia Ankara strain: comparison with other orthopoxviruses," *Virology* 1998; 244:365-396.
Baines, J. et al., "Immune-mediated tumor regression induced by CpG-containing oligodeoxynucleotides," *Clin Cancer Res* 2003; 9:2693-2700.
Ballas, Z.K., et al., "Divergent therapeutic and immunologic effects of oligodeoxynucleotides with distinct CpG motifs," *J Immunol* 2001; 167:4878-4886.

Baral, R.N., et al., "Immunostimulatory CpG oligonucleotides enhance the immune response of anti-idiotype vaccine that mimics carcinoembryonic antigen," *Cancer Immunol Immunother* 2003; 52:317-327.
Berns, E.M., et al., "p53 protein accumulation predicts poor response to tamoxifen therapy of patients with recurrent breast cancer," *J Clin Oncol* 1998; 16:121-127.
Berns, E.M., et al., "Complete sequencing of TP53 predicts poor response to systemic therapy of advanced breast cancer," *Cancer Res* 2000; 60:2155-2162.
Berson, J.F., et al., "A seven-transmembrane domain receptor involved in fusion and entry of T-cell-tropic human immunodeficiency virus type 1 strain," *J Virol* 1996; 70:6288-6295.
Blanchard, T.J., et al., "Modified vaccinia virus Ankara undergoes limited replication in human cells and lacks several immunomodulatory proteins: implications for use as a human vaccine," *J Gen Virol* 1998; 79(Pt 5):1159-1167.
Bruggerman, M., et al., "Human antibody production in transgenic mice: expression from 100 kb of the human IgH locus," *Eur J Immunol* 1991; 5:1323-1326.
Carpentier, A.F., et al., "Oligodeoxynucleotides containing CpG motifs can induce rejection of a neuroblastoma in mice," *Cancer Res* 1999; 59:5429-5432.
Carroll, M.W., et al., "Host range and cytopathogenicity of the highly attenuated MVA strain of vaccinia virus: propagation and generation of recombinant viruses in a nonhuman mammalian cell line," *Virology* 1997a; 238:198-211.
Carroll, M.W., et al., "Highly attenuated modified vaccinia virus Ankara (MVA) as an effective recombinant vector: a murine tumor model," *Vacccine* 1997b; 15:387-394.
Chakrabarti, S., et al., "Vaccinia virus expression vector: coexpression of beta-galactosidase provides visual screening of recombinant virus plaques," *Mol Cell Biol* 1985; 5:3403-3409.
Chu, R.S., et al., "CpG oligodeoxynucleotides act as adjuvants that switch on T helper 1 (Th1) immunity," *J Exp Med* 1997; 186:1623-1631.

(Continued)

*Primary Examiner*—Laura B Goddard
(74) *Attorney, Agent, or Firm*—Perkins Coie LLP; Patrick D. Morris

(57) ABSTRACT

Mutations to the tumor suppressor protein p53 have been observed in 40-60% of all human cancers. These mutations are often associated with high nuclear and cytoplasmic concentrations of p53. Since many tumors exhibit highly elevated p53 levels, the protein is an attractive target for cancer immunotherapy. Unfortunately, p53 is an autoantigen that is likely to be tolerated as a self-protein by the immune system. The present invention is based on the discovery that this self-tolerance can be overcome by administration of recombinant modified vaccinia Ankara (MVA) containing a nucleic acid that encodes p53 (rMVAp53). The invention discloses a method of generating a p53-specific CTL response to tumor cells expressing mutated p53 by administering a composition comprising rMVAp53. Administration of rMVAp53 decreases tumor development, tumor growth, and mortality in a variety of malignant cell types. These effects are enhanced by administration of CTLA-4 blocker and/or CpG oligodeoxynucleotide immunomodulators.

6 Claims, 17 Drawing Sheets

OTHER PUBLICATIONS

Collier, L.H., "Safety of recombinant vaccinia vaccines," *Lancet* 1991; 337:1035-1036.

Davila, E., et al., "Repeated administration of cytosine-phosphorothiolated guanine-containing oligonucleotides together with peptide/protein immunization results enhanced CTL responses with anti-tumor activity," *J Immunol* 2000; 165:539-547.

DeLeo, A.B., et al., "Cell surface antigens of chemically induced sarcomas of the mouse. I. Murine leukemia virus-related antigens and alloantigens on cultured fibroblasts and sarcoma cells: description of a unique antigen on BALB/c Meth A sarcoma," *J Exp Med* 1977; 146:720-734.

Dialynas, D.P., et al., "Characterization of the murine antigenic determinant, designated L3T4a, recognized by monoclonal antibody GK1.5: expression of L3T4a by functional T cell clones appears to correlate primarily with class II MHC antigen-reactivity," *Immunol Rev* 1983; 74:29-56.

Diamond, D.J., et al., "Development of a candidate HLA A*0201 restricted peptide-based vaccine against human cytomegalovirus infection," *Blood* 1997; 90:1751-1767.

Drexler, I., et al., "Modified vaccinia virus Ankara for delivery of human tyrosinase as melanoma-associated antigen: induction of tyrosi," *Cancer Res* 1999; 59:4955-4963.

Egen, J.G., et al., "CTLA-4: new insights into its biological function and use in tumor immunotherapy," *Nat Immunol* 2002; 3:611-618.

Eliyahu, D., et al., "Wild-type p53 can inhibit oncogene-mediated focus formation," *Proc Natl Acad Sci USA* 1989; 86:8763-8767.

Elkhuizen, P.H., et al., "High local recurrence risk after breast-conserving therapy in node-negative premenopausal breast cancer patients is greatly reduced by one course of perioperative chemotherapy: A European Organization for Research and Treatment of Cancer Breast Cancer Cooperative Group Study," *J Clin Oncol* 2000; 18:1075-1083.

Erdile, L.F., et al., "CD40 activation enhances the magnitude of cellular immune responses against p53 but not the avidity of the effectors," *Cancer Immunol Immunother* 2000; 49:410-416.

Espenschied, J., et al., "CTLA-4 blockade enhances the therapeutic effect of an attenuated poxvirus vacinne targeting p53 in an established murine tumor model," *J Immunol* 2003; 170:3401-3407.

Finlay, C.A., et al., "Activating mutations for transformation by p53 produce a gene product that forms an hsc70-p53 complex with an altered half-life," *Mol Cell Biol* 1998; 8:531-539.

Finlay, C.A., et al., "The p53 proto-oncogene can act as a suppressor of transformation," *Cell* 1989; 57:1083-1093.

Foote, J., et al., Antibody framework residues affecting the conformation of the hypervariable loops, *J Mol Biol* 1992; 224(2):487-499.

Gibson, L., et al., "Human Cytomegalovirus Proteins pp65 and IE1 are Common Targets for CD8+ T cell Responses in Children with Congenital and Postnatal HCMV infection," *J Immunol*, in press.

Gurney, E.G., et al., "Monoclonal antibodies against simian virus 40 T antigens: evidence for distinct subclasses of large T antigen and for similarities among nonviral T antigens," *J Virol* 1980; 34:752-763.

Hainaut, P., et al., "p53 and human cancer: the first ten thousand mutations," *Adv Cancer Res* 2000; 77:81-137.

Halevy, O., et al., "Frequent p53 mutations in chemically induced murine fibrosarcoma," *Oncogene* 1991; 6:1593-1600.

He, T.C., et al., "A simplified system for generating recombinant adenoviruses," *Proc Natl Acad Sci USA* 1998; 95:2509-2514.

Heckelsmiller, K., et al., "Combined dendritic cell- and CpG oligonucleotide-based immune therapy cures large tumors that resist chemotherapy," *Eur J Immunol* 2002; 32:3235-3245.

Hemmi, H., et al., "A Toll-like receptor recognizes bacterial DNA," *Nature* 2000; 408:740-745.

Hernandez, J., et al., "The use of HLA A2.1/p53 peptide tetramers to visualize the impact of self tolerance on the TCR repertoire," *J Immunol* 2000; 164:596-602.

Hilburger, R.M., et al., "Characterization of CD8+ cytotoxic T lymphocyte/tumor cell interactions reflecting recognition of an endogenously expressed murine wild-type p53 determinant," *Cancer Immunol Immunother* 2001; 49:603-612.

Hurwitz, A.A., et al., "CTLA-4 blockade synergizes with tumor-derived granulocyte-macrophage colony-stimulating for treatment of an experimental mammary carcinoma," *Proc. Natl Acad Sci USA* 1998; 95:10067-10071.

Hurwitz, A.A., et al., "Combination immunotherapy of primary prostate cancer in a transgenic mouse model using CTLA-4 blockade," *Cancer Res* 2000; 60:2444-2448.

Jones, P.T., et al., "Replacing complementarity-determining regions in a human antibody with those from a mouse," *Nature* 1986; 321(6069):522-525.

Kawarada, Y., et al., "NK-and CD8(+) T cell-mediated eradication of established tumors by peritumoral injection of CpG-containing oligodeoxynucleotides," *J Immunol* 2001; 167:5247-5253.

Kim, T.Y., et al., "Both E7 and CpG-oligodeoxynucleotide are required for protective immunity against challenge with human papillomavirus 16 (E6/E7) immortalized tumor cells: involvement of CD4+ and CD8+ T cells in protection," *Cancer Res* 2002; 62:7273-7240.

Kit, S., et al., "Enhanced thmidine kinase activity following infection of green monkey kidney cells by simian adenoviruses, simiam papovavirus SV40, and an adenovirus-SV40 'hybrid'," *Virology* 1965; 27:453-457.

Koo, G.C., et al., "Establishment of monoclonal anti-Nk-1.1 antibody," *Hybridoma* 1984; 3:301-303.

Krieg, A.M., et al., "CpG motifs in bacterial DNA and their immune effects," *Annu Rev Immunol* 2002; 20:709-760.

Krieg, A.M., et al., "CpG motifs: the active ingredient in bacterial extracts?" *Nat Med* 2003; 9:831-835.

Krummel, M.F., et al., "CD28 and CTLA-4 have opposing effects on the response of T cells to stimulation," *J Exp Med* 1995; 182:459-465.

Levine, A.J., et al., "p53, the cellular gatekeeper for growth and division," *Cell* 1997; 88:323-331.

Low, N.M., et al., "Mimicking somatic hypermutation: affinity maturation," *J Mol Biol* 1986; 260:359-368.

MacPherson, I., et al., "Polyoma transformation of hamster cell clones—an investigation of genetic factors affecting cell competence," *Virology* 1962; 16:147-151.

Mayordomo, J.I., et al., "Therapy of murine tumors with p53 wild-type and mutant sequence peptide-based vaccines," *J Exp Med* 1996; 183:1357-1365.

Mayr, A., et al., "[The smallpox vaccination strain MVA: marker, genetic structure, experience gained with the parenteral vaccination and behavior in organisms with a debilitated defence mechanism (author's transl)]," *Zentralbl Bakteriol [B]* 1978; 167:375-390.

Mayr, A., et al., "[Historical review of smallpox, the eradication of smallpox and the attenuated smallpox MVA vaccin]," *Berlin Munch Tierarztl Wochenschr* 1999; 112:322-328.

Mendez, M.J., et al., "Functional transplant of megabase human immunoglobin loci recapitulates human antibody response in mice," *Nat Genet* 1997; 2:146-156.

Meyer, H., et al., "Mapping of deletions in the genome of the highly attenuated vaccinia virus MVA and their influence on virulence," *J Gen Virol* 1991; 72(Pt 5):1031-1038.

Miconnet, I., et al., "Cancer vaccine design: a novel bacterial adjuvant for peptide-specific CTL induction," *J Immunol* 2001; 166:4612-4619.

Millikan, R., et al., "p53 mutations in benign breast tissue," *J Clin Oncol* 1995; 13:2293-2300.

Moldoveanu, Z., et al., "CpG DNA, a novel immune enhancer for systemic and mucosal immunization with influenza virus," *Vaccine* 1998; 16:1216-1224.

Mulryan, K., et al., "Attenuated recombinant vaccinia virus expressing oncofetal antigen (tumor-associated antigen) 5T4 induces activity therapy of established tumors," *Mol Cancer* 2002; 1:1129-1137.

Noguchi, Y., et al., "Infuence of interleukin 12 on p53 peptide vaccination againt established Meth A sarcoma," *Proc. Natl Acad Sci USA* 1995; 92:2219-2223.

Norbury, C.C., et al., "Visualizing priming of virus-specific CD8+ cells by infected dendritic cells in vivo," *Nat Immunol* 2002; 3:265-271.

Offringa, R., et al., "p53: a potential target antigen for immunotherapy of cancer," *ANN N Y Acad Sci*; 910:223-233.

Ourmanov, I. et al., "Comparative efficacy of recombinant modified vaccinia virus Ankara expressing simian immunodeficiency virus (SIV) Gag-Pol and/or Env in macaques challenged with pathogenic SIV," *J Virol* 2000; 74:2740-2751.

Pasare, C., et al., "Toll pathway-dependent blockade of CD4+CD25+ T-cell mediated supression by dendritic cells," *Science* 2003; 299:1033-1036.

Pratap, R., et al., "Breach carcinoma in women under the age of 50: relationship between p53 immunostaining, tumour grade, and axillary lymph node status," *Breast Cancer Res Treat* 1998; 49:35-39.

Querzoli, P., et al., "Modulation of biomarkers in minimal breast carcinoma: a model for human breast carcinoma progression," *Cancer* 1998; 83:89-97.

Querzoli, P., et al., "Biophenotypes and Survival of BRCA1 and TP53 Deleted Breast Cancer in Young Women," *Breast Cancer Res Treatment* 2001; 66:135-142.

Ramirez, J.C., et al., "Attenuated modified vaccinia virus Ankara can be used as an immunizing agent under conditions of preexisting immunity to the vector," *J Virol* 2000; 74:7651-7655.

Ramirez, J.C., et al., "Biology of attenuated vaccinia virus Ankara recombinant vector in mice: virus fate and activation," *J Virol* 2000; 74:923-933.

Read, S., et al., "Cytotoxic T lymphocyte-associated antigen 4 plays an essential role in the function of CD25(+)CD4(+) regulatory cells that control intestinal inflammation," *J Exp Med* 2000; 192:295-302.

Redfield, R.R., et al., "Disseminated vaccinia in military recruit with human immunodeficiency virus (HIV) disease," *N Engl J Med* 1987; 316:673-676.

Reich, N.C., et al., "Growth regulation of a cellular tumour antigen, p53, in nontransformed cells," *Nature* 1984; 308:199-201.

Rosales, C., et al., "A recombinant vaccinia virus containing the papilloma E2 protein promotes tumor regression by stimulating macrophage antibody-dependent cytotoxicity," *Cancer Immunol Immunother* 2003; 49:347-360.

Rosenberg, S.A., "Progress in human immunology and immunotherapy," *Nature* 2001; 411:380-384.

Sandler, A.D., et al., "CpG oligonucleotides enhance the tumor antigen-specific immune response of a granulocyte macrophage colony-stimulating factor-based vaccine strategy in neuroblastoma," *Cancer Res* 2003; 63:394-399.

Schmid, P., et al., "Expression of p53 during mouse embryogenesis," *Development* 1997; 113:857-865.

Selvanayagam, C.S., et al., "Latent expression of p53 mutations and radiation-induced mammary cancer," *Cancer Res* 1995; 55:3310-3317.

Sharma, S., et al., "Intra-tumoral injection of CpG results in the inhibition of tumor growth in murine Colon-26 and B-16 tumors," *Biotechnol Lett* 2003; 25:149-153.

Sirvent, J.J., et al., "Prognostic value of p53 protein expression and clincopathological factors in infiltrating ductal carcinoma of the breast," *Histol Histopathol* 2001; 16:99-106.

Stern, B.V., et al., "Vaccination with tumor peptide in CpG adjuvant protects via IFN-gamma-dependent CD4 cell immunity," *J Immonol* 2002; 168:6099-6105.

Stittelaar, K.J., et al., "Safety of a modified vaccinia virus Ankara (MVA) in immune-suppressed macaques," *Vaccine* 2001; 19: 3700-3709.

Sukumar, S., et al., "Animal models for breat cancer," *Mutat Res* 1995; 333:37-34.

Sutter, G., et al., "Nonreplicating vaccinia virus vector efficiently expresses recombinant genes," *Proc Natl Acad Sci USA* 1992; 89:10847-10851.

Tan, M.H., et al., "Murine colon adenocarcinomas: methods for selective culture in vitro," *J Natl Cancer Inst* 1976; 56:871-873.

Theobald, M., et al., "Tolerance to p53 by A2.1-restricted cytotoxic T lymphocytes," *J Exp Med* 1997; 185:833-841.

Turner, B.C., et al., "Mutant p53 protein overexpression in women with ipsilateral breast tumor recurrence following lumpectomy and radiation therapy," *Cancer* 2000; 88:1091-1098.

Van Elsas, A., et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," *J Exp Med* 1999; 190:355-366.

Vierboom, M.P., et al., "High steady-state levels of p53 are not a prerequisite for tumor eradication by wild-type p53-specific cytotoxic T lymphocytes," *Cancer Res* 2000; 60:5508-5513.

Vierboom, M.P., et al., "Cyclophosphamide enhances anti-tumor effect of wild-type p53-specific CTL," *Int J Cancer* 2000; 87:253-260.

Vierboom, M.P., et al., "Tumor eradication by wild-type p53-specific cytotoxic T lymphocytes," *J Exp Med* 1997; 186:695-704.

Weiner, G.J., et al., "Immunostimulatory oligodeoxynucleotides containing the CpG motif are effective as immune adjuvants in tumor antigen immunization," *Proc Natl Acad Sci USA* 1997; 94:10833-10837.

Wiedenfeld, E.A., et al., "Evidence for selection against human lung cancers bearing p53 missense mutations which occur within the HLA A*0201 peptide consensus motif," *Cancer Res* 1994; 54:1175-1177.

Winter, G., et al., "Making antibodies by phage display technology," *Annu Rev Immunology* 1994; 12:433-455.

Zambetti, G.P., et al., "A comparison of the biological activities of wild-type and mutant p53," 1993; 7:855-865.

Zellars, R.C., et al., "Prognostic value of p53 for local failure in mastectomy-treated breast cancer patients," *J Clin Oncol* 2000; 18:1906-1913.

Glazko, G.V. et al., "Mutation Hotspots in the p53 gene in Tumors of Different Origin: Correlation with Evolutionary Conservation and Signs of Positive Selection" *Biochemica et Biophysica Acta* 2004; 1679:95-106.

Ober, B.T. et al., "Immunogenicity and Safety of Defective Vaccinia Virus Lister: Comparison with Modified Vaccinia Virus Ankara," *Journal of Virology* 2002; 76:7713-7723.

Timiryasova, T.M. et al., "Vaccinia Virus-Mediated Expression of Wild-Type p53 Suppresses Glioma Cell Growth and Induces Apoptosis," *International Journal of Oncology* 1999; 14:845-854.

Carroll, et al., *Vaccine* 1997; 15:387-394, IDS.

Stratagene, 1988 catalog (p. 39).

"Transient Host Range Selection for Genetic Engineering of Modified Vaccinia Virus Ankara," BioTechniques 28:1137-1148 (Jun. 2000), vol. 28, No. 6, pp. 1137-1148.

Supplementary European Search Report dated Jul. 25, 2007 for European Patent Application No. EP03814346, 5 pages.

* cited by examiner

SEQUENCE LISTING

<160> NUMBER OF SEQ ID NOS: 7

<210> SEQ ID NO 1
<211> LENGTH: 1173
<212> TYPE: DNA
<213> ORGANISM: Mus musculus

<400> SEQUENCE: 1

-continued

| | | |
|---|---|---|
| atgactgcca tggaggagtc acagtcggat atcagcctcg agctccctct gagccaggag | 60 | |
| acattttcag gcttatggaa actacttcct ccagaagata tcctgccatc acctcactgc | 120 | |
| atggacgatc tgttgctgcc ccaggatgtt gaggagtttt ttgaaggccc aagtgaagcc | 180 | |
| ctccgagtgt caggagctcc tgcagcacag gaccctgtca ccgagacccc tgggccagtg | 240 | |
| gcccctgccc cagccactcc atggcccctg tcatcttttg tcccttctca aaaaacttac | 300 | |
| cagggcaact atggcttcca cctgggcttc ctgcagtctg gacagccaa gtctgttatg | 360 | |
| tgcacgtact ctcctcccct caataagcta ttctgccagc tggtgaagac gtgccctgtg | 420 | |
| cagttgtggg tcagcgccac acctccagct gggagccgtg tccgcgccat ggccatctac | 480 | |
| aagaagtcac agcacatgac ggaggtcgtg agacgctgcc ccaccatga gcgctgctcc | 540 | |
| gatggtgatg gcctggctcc tccccagcat cttatccggg tggaaggaaa tttgtatccc | 600 | |
| gagtatctgg aagacaggca gacttttcgc cacagcgtgg tggtacctta tgagccaccc | 660 | |
| gaggccggct ctgagtatac caccatccac tacaagtaca tgtgtaatag ctcctgcatg | 720 | |
| gggggcatga accgccgacc tatccttacc atcatcacac tggaagactc cagtgggaac | 780 | |
| cttctgggac gggacagctt tgaggttcgt gtttgtgcct gccctgggag agaccgccgt | 840 | |
| acagaagaag aaaatttccg caaaaaggaa gtcctttgcc ctgaactgcc cccagggagc | 900 | |
| gcaaagagag cgctgcccac ctgcacaagc gcctctcccc gcaaaagaa aaaccactt | 960 | |
| gatggagagt atttcacccct caagatccgc gggcgtaaac gcttcgagat gttccgggag | 1020 | |
| ctgaatgagg ccttagagtt aaaggatgcc catgctacag aggagtctgg agacagcagg | 1080 | |
| gctcactcca gctacctgaa gaccaagaag ggccagtcta cttcccgcca taaaaaaaca | 1140 | |
| atggtcaaga agtgggggcc tgactcagac tga | 1173 | |

<210> SEQ ID NO 2
<211> LENGTH: 1182
<212> TYPE: DNA
<213> ORGANISM: Homo sapiens

<400> SEQUENCE: 2

| | | |
|---|---|---|
| atggaggagc cgcagtcaga tcctagcgtc gagccccctc tgagtcagga aacattttca | 60 | |
| gacctatgga aactacttcc tgaaaacaac gttctgtccc ccttgccgtc ccaagcaatg | 120 | |
| gatgatttga tgctgtcccc ggacgatatt gaacaatggt tcactgaaga cccaggtcca | 180 | |
| gatgaagctc ccagaatgcc agaggctgct ccccgcgtgg ccctgcacc agcagctcct | 240 | |
| acaccggcgg cccctgcacc agcccctcc tggcccctgt catcttctgt cccttcccag | 300 | |
| aaaacctacc agggcagcta cggtttccgt ctgggcttct tgcattctgg gacagccaag | 360 | |
| tctgtgactt gcacgtactc ccctgccctc aacaagatgt tttgccaact ggccaagacc | 420 | |
| tgccctgtgc agctgtgggt tgattccaca ccccgcccg gcacccgcgt ccgcgccatg | 480 | |
| gccatctaca agcagtcaca gcacatgacg gaggttgtga ggcgctgccc caccatgag | 540 | |
| cgctgctcag atagcgatgg tctggcccct cctcagcatc ttatccgagt ggaaggaaat | 600 | |
| ttgcgtgtgg agtatttgga tgacagaaac acttttcgac atagtgtggt ggtgccctat | 660 | |
| gagccgcctg aggttggctc tgactgtacc accatccact acaactacat gtgtaacagt | 720 | |
| tcctgcatgg gcggcatgaa ccggaggccc atcctcacca tcatcacact ggaagactcc | 780 | |
| agtggtaatc tactgggacg gaacagcttt gaggtgcatg tttgtgcctg tcctgggaga | 840 | |
| gaccggcgca cagaggaaga gaatctccgc aagaaagggg agcctcacca cgagctgccc | 900 | |
| ccagggagca ctaagcgagc actgtccaac aacaccagct cctctcccca gccaaagaag | 960 | |

```
aaaccactgg atggagaata tttcacccct cagatccgtg ggcgtgagcg cttcgagatg    1020
ttccgagagc tgaatgaggc cttggaactc aaggatgccc aggctgggaa ggagccaggg    1080
gggagcaggg ctcactccag ccacctgaag tccaaaaagg gtcagtctac ctcccgccat    1140
aaaaaactca tgttcaagac agaagggcct gactcagact ga                      1182
```

```
<210> SEQ ID NO 3
<211> LENGTH: 41
<212> TYPE: DNA
<213> ORGANISM: Artificial
<220> FEATURE:
<223> OTHER INFORMATION: forward primer for amplification of wt human
      p53

<400> SEQUENCE: 3
agctttgttt aaacgccacc acccacgctt ccctggattg g                        41

<210> SEQ ID NO 4
<211> LENGTH: 37
<212> TYPE: DNA
<213> ORGANISM: artificial
<220> FEATURE:
<223> OTHER INFORMATION: reverse primer for amplification of wt human
      p53

<400> SEQUENCE: 4
ttggcgcgcc tttatttcag tctgagtcag gcccttc                             37

<210> SEQ ID NO 5
<211> LENGTH: 8618
<212> TYPE: DNA
<213> ORGANISM: Artificial
<220> FEATURE:
<223> OTHER INFORMATION: pLW22 plasmid containing wt human p53 insert
<220> FEATURE:
<221> NAME/KEY: misc_feature
<222> LOCATION: (3810)..(3817)
<223> OTHER INFORMATION: Asc-1 cutting site
<220> FEATURE:
<221> NAME/KEY: misc_feature
<222> LOCATION: (3810)..(3823)
<223> OTHER INFORMATION: Segment of PCR primer sequence
<220> FEATURE:
<221> NAME/KEY: misc_feature
<222> LOCATION: (3824)..(5051)
<223> OTHER INFORMATION: wt human p53 sequence
<220> FEATURE:
<221> NAME/KEY: misc_feature
<222> LOCATION: (5052)..(5068)
<223> OTHER INFORMATION: Segment of PCR primer sequence
<220> FEATURE:
<221> NAME/KEY: misc_feature
<222> LOCATION: (5061)..(5068)
<223> OTHER INFORMATION: Pme-1 cutting site

<400> SEQUENCE: 5
cctcctgaaa aactggaatt taatacacca tttgtgttca tcatcagaca tgatattact     60
ggatttatat tgtttatggg taaggtagaa tctccttaat atgggtacgg tgtaaggaat    120
cattatttta tttatattga tgggtacgtg aaatctgaat tttcttaata aatattattt    180
ttattaaatg tgtatatgtt gttttgcgat agccatgtat ctactaatca gatctattag    240
agatattatt aattctggtg caatatgaca aaaattatac actaattagc gtctcgtttc    300
agacatggat ctgtcacgaa ttaatacttg gaagtctaag cagctgaaaa gctttctctc    360
tagcaaagat gcatttaagg cggatgtcca tggacatagt gccttgtatt atgcaatagc    420
```

```
tgataataac gtgcgtctag tatgtacgtt gttgaacgct ggagcattga aaaatcttct    480
agagaatgaa tttccattac atcaggcagc cacattggaa gataccaaaa tagtaaagat    540
tttggctatt cagtggactg gatgattcga ggtacccgat cccccctgcc cggttattat    600 tattttttgac accagaccaa ctggtaatgg tagcgaccgg cgctcagctg aattccgccg    660
atactgacgg gctccaggag tcgtcgccac caatccccat atggaaaccg tcgatattca    720
gccatgtgcc ttcttccgcg tgcagcagat ggcgatggct ggtttccatc agttgctgtt    780
gactgtagcg gctgatgttg aactggaagt cgccgcgcca ctggtgtggg ccataattca    840
attcgcgcgt cccgcagcgc agaccgtttt cgctcgggaa gacgtacggg gtatacatgt    900
ctgacaatgg cagatcccag cggtcaaaac aggcggcagt aaggcggtcg ggatagtttt    960
cttgcggccc taatccgagc cagtttaccc gctctgctac ctgcgccagc tggcagttca   1020
ggccaatccg cgccggatgc ggtgtatcgc tcgccacttc aacatcaacg gtaatcgcca   1080
tttgaccact accatcaatc cggtaggttt tccggctgat aaataaggtt ttcccctgat   1140
gctgccacgc gtgagcggtc gtaatcagca ccgcatcagc aagtgtatct gccgtgcact   1200
gcaacaacgc tgcttcggcc tggtaatggc ccgccgcctt ccagcgttcg acccaggcgt   1260
tagggtcaat gcgggtcgct tcacttacgc caatgtcgtt atccagcggt gcacgggtga   1320
actgatcgcg cagcggcgtc agcagttgtt ttttatcgcc aatccacatc tgtgaaagaa   1380
agcctgactg gcggttaaat tgccaacgct tattacccag ctcgatgcaa aaatccattt   1440
cgctggtggt cagatgcggg atggcgtggg acgcggcggg gagcgtcaca ctgaggtttt   1500
ccgccagacg ccactgctgc caggcgctga tgtgcccggc ttctgaccat gcggtcgcgt   1560
tcggttgcac tacgcgtact gtgagccaga gttgcccggc gctctccggc tgcggtagtt   1620
caggcagttc aatcaactgt ttaccttgtg gagcgacatc cagaggcact tcaccgcttg   1680
ccagcggctt accatccagc gccaccatcc agtgcaggag ctcgttatcg ctatgacgga   1740
acaggtattc gctggtcact tcgatggttt gcccggataa acggaactgg aaaaactgct   1800
gctggtgttt tgcttccgtc agcgctggat gcggcgtgcg gtcggcaaag accagaccgt   1860
tcatacagaa ctggcgatcg ttcggcgtat cgccaaaatc accgccgtaa gccgaccacg   1920
ggttgccgtt ttcatcatat ttaatcagcg actgatccac ccagtcccag acgaagccgc   1980
cctgtaaacg gggatactga cgaaacgcct gccagtattt agcgaaaccg ccaagactgt   2040
tacccatcgc gtgggcgtat tcgcaaagga tcagcgggcg cgtctctcca ggtagcgaaa   2100
gccatttttt gatggaccat ttcggcacag ccgggaaggg ctggtcttca tccacgcgcg   2160
cgtacatcgg gcaaataata tcggtggccg tggtgtcggc tccgccgcct tcatactgca   2220
ccgggcggga aggatcgaca gatttgatcc agcgatacag cgcgtcgtga ttagcgccgt   2280
ggcctgattc attccccagc gaccagatga tcacactcgg gtgattacga tcgcgctgca   2340
ccattcgcgt tacgcgttcg ctcatcgccg gtagccagcg cggatcatcg gtcagacgat   2400
tcattggcac catgccgtgg gtttcaatat tggcttcatc caccacatac aggccgtagc   2460
ggtcgcacac cgtgtaccac agcggatggt tcggataatg cgaacagcgc acggcgttaa   2520
agttgttctg cttcatcagc aggatatcct gcaccatcgt ctgctcatcc atgacctgac   2580
catgcagagg atgatgctcg tgacggttaa cgcctcgaat cagcaacggc ttgccgttca   2640
gcagcagcag accattttca atccgcacct cgcggaaacc gacatcgcag gcttctgctt   2700
caatcagcgt gccgtcggcg gtgtgcagtt caaccaccgc acgatagaga ttcgggattt   2760
cggcgctcca cagtttcggg ttttcgacgt tgagacgtag tgtgacgcga tcggcataac   2820
```

```
caccacgctc atcgataatt tcaccgccga aaggcgcggt gccgctggcg acctgcgttt    2880 cacccctgcca taaagaaact gttacccgta ggtagtcacg caactcgccg cacatctgaa   2940
cttcagcctc cagtacagcg cggctgaaat catcattaaa gcgagtggca acatggaaat   3000
cgctgatttg tgtagtcggt ttatgcagca acgagacgtc acggaaaatg ccgctcatcc   3060
gccacatatc ctgatcttcc agataactgc cgtcactcca acgcagcacc atcaccgcga   3120
ggcggttttc tccggcgcgt aaaaatgcgc tcaggtcaaa ttcagacggc aaacgactgt   3180
cctggccgta accgacccag cgcccgttgc accacagatg aaacgccgag ttaacgccat   3240
caaaaataat tcgcgtctgg ccttcctgta gccagctttc atcaacatta aatgtgagcg   3300
agtaacaacc cgtcggattc tccgtgggaa caaacggcgg attgaccgta atgggatagg   3360
ttacgttggt gtagatgggc gcatcgtaac cgtgcatctg ccagtttgag gggacgacga   3420
cagtatcggc ctcaggaaga tcgcactcca gccagctttc cggcaccgct tctggtgccg   3480
gaaaccaggc aaagcgccat cgccattca ggctgcgcaa ctgttgggaa gggcgatcgg   3540
tgcgggcctc ttcgctatta cgccagctgg cgaaaggggg atgtgctgca aggcgattaa   3600
gttgggtaac gccagggttt tcccagtcac gacgttgtaa aacgacggga tctcccatgc   3660
tcgagttatg atctacttcc ttaccgtgca ataaattaga atatattttc tacttttacg   3720
agaaattaat tattgtattt attatttatg ggtgaaaaac ttactataaa aagcgggtgg   3780
gtttggaatt agtgaaagct gggagatctg gcgcgccttt atttcagtct gagtcaggcc   3840
cttctgtctt gaacatgagt tttttatggc gggaggtaga ctgaccctttt ttggacttca   3900 ggtggctgga gtgagccctg ctccccctg gctccttccc agcctgggca tccttgagtt   3960
ccaaggcctc attcagctct cggaacatct cgaagcgctc acgccacgg atctgaaggg   4020 tgaaatattc tccatccagt ggtttcttct ttggctgggg agaggagctg gtgttgttgg   4080
gcagtgctcg cttagtgctc cctgggggca gctcgtggtg aggctcccct tcttgcgga   4140 gattctcttc ctctgtgcgc cggtctctcc caggacaggc acaaacacgc acctcaaagc   4200
tgttccgtcc cagtagatta ccactggagt cttccagtgt gatgatggtg aggatgggcc   4260
tccggttcat gccgcccatg caggaactgt tacacatgta gttgtagtgg atggtggtac   4320
agtcagagcc aacctcaggc ggctcatagg gcaccaccac actatgtcga aaagtgtttc   4380
tgtcatccaa atactccaca cgcaaatttc cttccactcg gataagatgc tgaggagggg   4440
ccagaccatc gctatctgag cagcgctcat ggtgggggca gcgcctcaca acctccgtca   4500
tgtgctgtga ctgcttgtag atggccatgg cgcggacgcg ggtgccgggc ggggggtgtgg   4560 aatcaaccca cagctgcaca gggcaggtct tggccagttg gcaaaacatc ttgttgaggg   4620
caggggagta cgtgcaagtc acagacttgg ctgtcccaga atgcaagaag cccagacgga   4680
aaccgtagct gccctggtag gttttctggg aagggacaga agatgacagg ggccaggagg   4740
gggctggtgc aggggccgcc ggtgtaggag ctgctggtgc aggggccacg ggggagcag    4800 cctctggcat tctgggagct tcatctggac ctgggtcttc agtgaaccat tgttcaatat   4860
cgtccgggga cagcatcaaa tcatccattg cttgggacgg caaggggac agaacgttgt    4920 tttcaggaag tagtttccat aggtctgaaa atgtttcctg actcagaggg ggctcgacgc   4980
taggatctga ctgcggctcc tccatggcag tgacccggaa ggcagtctgg ctgccaatcc   5040
agggaagcgt gggtggtggc gtttaaacgg atcccgagct tatttatatt ccaaaaaaaa   5100
aaaataaaat ttcaatttttt aagctgggga tcctctagag tcgacctgca ggcatgctcg   5160
```

```
agcggccgcc agtgtgatgg atatctgcag aattcggctt gggggctgc aggtggatgc    5220 gatcatgacg tcctctgcaa tggataacaa tgaacctaaa gtactagaaa tggtatatga    5280
tgctacaatt ttacccgaag gtagtagcat ggattgtata aacagacaca tcaatatgtg    5340
tatacaacgc acctatagtt ctagtataat tgccatattg gatagattcc taatgatgaa    5400
caaggatgaa ctaaataata cacagtgtca tataattaaa gaatttatga catacgaaca    5460
aatggcgatt gaccattatg gagaatatgt aaacgctatt ctatatcaaa ttcgtaaaag    5520
acctaatcaa catcacacca ttaatctgtt taaaaaaata aaaagaaccc ggtatgacac    5580
ttttaaagtg gatcccgtag aattcgtaaa aaagttatc ggatttgtat ctatcttgaa    5640
caaatataaa ccggtttata gttacgtcct gtacgagaac gtcctgtacg atgagttcaa    5700
atgtttcatt gactacgtgg aaactaagta tttctaaaat taatgatgca ttaattttg    5760 tattgattct caatcctaaa aactaaaata tgaataagta ttaaacatag cggtgtacta    5820
attgatttaa cataaaaaat agttgttaac taatcatgag gactctactt attagatata    5880
ttctttggag aaatgacaac gatcaaaccg ggcatgcaag cttgtctccc tatagtgagt    5940
cgtattagag cttggcgtaa tcatggtcat agctgtttcc tgtgtgaaat tgttatccgc    6000
tcacaattcc acacaacata cgagccggaa gcataaagtg taaagcctgg ggtgcctaat    6060
gagtgagcta actcacatta ttgcgttgc gctcactgcc cgctttcgag tcgggaaacc    6120
tgtcgtgcca gctgcattaa tgaatcggcc aacgcgcggg gagaggcggt ttgcgtattg    6180
ggcgctcttc cgcttcctcg ctcactgact cgctgcgctc ggtcgttcgg ctgcggcgag    6240
cggtatcagc tcactcaaag gcggtaatac ggttatccac agaatcaggg gataacgcag    6300
gaaagaacat gtgagcaaaa ggccagcaaa aggccaggaa ccgtaaaaag gccgcgttgc    6360
tggcgttttt cgataggctc cgccccctg acgagcatca aaaaatcga cgctcaagtc    6420 agaggtggcg aaacccgaca ggactataaa gataccaggc gtttccccct ggaagctccc    6480
tcgtgcgctc tcctgttccg acctgccgc ttaccggata cctgtccgcc tttctccctt    6540
cgggaagcgt ggcgctttct catagctcac gctgtaggta tctcagttcg gtgtaggtcg    6600
ttcgctccaa gctgggctgt gtgcacgaac cccccgttca gcccgaccgc tgcgccttat    6660
ccggtaacta tcgtcttgag tccaacccgg taagacacga cttatcgcca ctggcagcag    6720
ccactggtaa caggattagc agagcgaggt atgtaggcgg tgctacagag ttcttgaagt    6780
ggtggcctaa ctacggctac actagaagga cagtatttgg tatctgcgct ctgctgaagc    6840
cagttaccct cggaaaaaga gttggtagct cttgatccgg caaacaaacc accgctggta    6900
gcggtggttt ttttgtttgc aagcagcaga ttacgcgcag aaaaaaagga tctcaagaag    6960
atcctttgat cttttctacg gggtctgacg ctcagtggaa cgaaaactca cgttaaggga    7020
ttttggtcat gagattatca aaaaggatct tcacctagat ccttttaaat taaaaatgaa    7080
gttttaaatc aatctaaagt atatatgagt aaacttggtc tgacagttac caatgcttaa    7140
tcagtgaggc acctatctca gcgatctgtc tatttcgttc atccatagtt gcctgactcc    7200
ccgtcgtgta gataactacg atacgggagg gcttaccatc tggccccagt gctgcaatga    7260
taccgcgaga cccacgctca ccggctccag atttatcagc aataaaccag ccagccggaa    7320
gggccgagcg cagaagtggt cctgcaactt tatccgcctc catccagtct attaattgtt    7380
gccgggaagc tagagtaagt agttcgccag ttaatagttt gcgcaacgtt gttggcattg    7440
ctacaggcat cgtggtgtca cgctcgtcgt ttggtatggc ttcattcagc tccgttccc    7500 aacgatcaag gcgagttaca tgatccccca tgttgtgcaa aaaagcggtt agctccttcg    7560
```

-continued

```
gtcctccgat cgttgtcaga agtaagttgg ccgcagtgtt atcactcatg gttatggcag    7620
cactgcataa ttctcttact gtcatgccat ccgtaagatg cttttctgtg actggtgagt    7680
actcaaccaa gtcattctga gaatagtgta tgcggcgacc gagttgctct tgcccggcgt    7740
caatacggga taataccgcg ccacatagca gaactttaaa agtgctcatc attggaaaac    7800
gttcttcggg gcgaaaactc tcaaggatct taccgctgtt gagatccagt tcgatgtaac    7860
ccactcgtgc acccaactga tcttcagcat cttttacttt caccagcgtt tctgggtgag    7920
caaaaacagg aaggcaaaat gccgcaaaaa agggaataag ggcgacacgg aaatgttgaa    7980
tactcatact cttcctttt caatattatt gaagcattta tcagggttat tgtctcatga    8040
gcggatacat atttgaatgt atttagaaaa ataaacaaat aggggttccg cgcacatttc    8100
cccgaaaagt gccacctgac gtctaagaaa ccattattat catgacatta acctataaaa    8160
ataggcgtat cacgaggccc tttcgtctcg cgcgtttcgg tgatgacggt gaaaacctct    8220
gacacatgca gctcccggag acggtcacag cttgtctgta agcggatgcc gggagcagac    8280
aagcccgtca gggcgcgtca gcgggtgttg gcgggtgtcg ggctggctt aactatgcgg    8340 catcagagca gattgtactg agagtgcacc atatgcggtg tgaaataccg cacagatgcg    8400
taaggagaaa ataccgcatc aggcgccatt cgccattcag gctgcgcaac tgttgggaag    8460
ggcgatcggt gcgggcctct tcgctattac gccagctggc gaaaggggga tgtgctgcaa    8520
ggcgattaag ttgggtaacg ccagggtttt cccagtcacg acgttgtaaa acgacggcca    8580
gtgaattgga tttaggtgac actatagaat acgaattc                            8618
```

<210> SEQ ID NO 6
<211> LENGTH: 20
<212> TYPE: DNA
<213> ORGANISM: artificial
<220> FEATURE:
<223> OTHER INFORMATION: synthetic oligodeoxynucleotide 1826 containing CpG motifs
<220> FEATURE:
<221> NAME/KEY: misc_feature
<222> LOCATION: (6)..(11)
<223> OTHER INFORMATION: CpG motif
<220> FEATURE:
<221> NAME/KEY: misc_feature
<222> LOCATION: (15)..(20)
<223> OTHER INFORMATION: CpG motif

<400> SEQUENCE: 6
tccatgacgt tcctgacgtt    20

<210> SEQ ID NO 7
<211> LENGTH: 20
<212> TYPE: DNA
<213> ORGANISM: artificial
<220> FEATURE:
<223> OTHER INFORMATION: synthetic oligodeoxynucleotide 1982
<300> PUBLICATION INFORMATION:
<301> AUTHORS: Moldoveanu, Z., Love-Homan, L., Huang, W.Q., Krieg, A.M.
<302> TITLE: CpG DNA, a novel immune enhancer for systemic and mucosal immunization with influenza virus
<303> JOURNAL: Vaccine
<304> VOLUME: 16
<306> PAGES: 1216-1224
<307> DATE: 1998

<400> SEQUENCE: 7
tccaggactt ctctcaggtt    20

MODIFIED VACCINIA ANKARA EXPRESSING P53 IN CANCER IMMUNOTHERAPY

CROSS-REFERENCE TO RELATED APPLICATIONS

The present utility application is a divisional of U.S. patent application Ser. No. 10/746,558, filed Dec. 23, 2003, issued as U.S. Pat. No. 7,256,037 on Aug. 14, 2007, and claims priority to U.S. Provisional Application No. 60/436,268, filed Dec. 23, 2002, and U.S. Provisional Application No. 60/466,607, filed Apr. 30, 2003, the disclosures of which are incorporated by reference in their entirety herein.

GOVERNMENT INTEREST

This invention was made with government support in part by grants from the NIH, Division of AIDS (RO1-AI43267 and R21-AI44313) and NCI: RO1-CA77544, PO1-CA30206, R29-CA70819, and CA33572. The government may have certain rights in this invention.

FIELD OF THE INVENTION

The present invention relates to the fields of virology, molecular biology, and tumor immunology. Specifically, this invention relates to compositions and methods for eliciting immune responses effective against malignancies expressing p53.

BACKGROUND p53 is a tumor suppressor protein that regulates the expression of certain genes required for cell cycle arrest or apoptosis. The tumor suppressor gene encoding p53 is activated by DNA damage, cell stress, or the aberrant expression of certain oncogenes (Levine 1997). Once activated, wild type p53 (wt p53) serves to temporarily arrest the cell cycle, allowing time for DNA repair and preventing cells with damaged DNA from proliferating uncontrollably (Levine 1997). p53 is also involved in inducing apoptosis in cells with certain types of physiologic damage (Levine 1997).

Mutations in p53 that functionally inactivate its growth suppressing ability have been observed in 40-60% of all human cancers, and are associated with the malignant phenotype (Hainaut 2000). Mutations to p53 occur as early events in tumorigenesis (Millikan 1995; Querzoli 1998; Allred 1993), abrogating the ability of the protein to suppress cell division (Finlay 1989; Eliyahu 1989). The regulation of p53 expression in cells can occur at the level of p53 mRNA abundance or at the level of p53 protein abundance. Mutations of p53 are often associated with high nuclear and cytoplasmic concentrations of the p53 protein, due to the prolonged half-life of the mutated protein. Many tumors are characterized by highly elevated intracellular p53 levels compared to nonmalignant cells. Other tumors synthesize large amount of mutated p53, but contain low or below normal steady-state levels of intracellular p53, presumably as a result of accelerated intracellular degradation of the protein. Overexpression of p53 is an independent predictor of more aggressive cancers (Turner 2000; Elkhuizen 2000; Zellars 2000), lymph node metastases (Pratap 1998), failure to respond to standard therapies (Berns 1998; Berns 2000), and mortality (Sirvent 2001; Querzoli 2001).

Missense point mutations are the most frequent p53 mutations in cancer, leaving the majority of the p53 protein in its wild type form (wt p53). Although p53 mutations may represent true tumor specific antigens, most of these mutations occur at sites that do not correspond to immunologic epitopes recognized by T cells (Wiedenfeld 1994). Because of this, any widely applicable p53-directed immunotherapy must target wt p53. In experimental models, it has been possible to target p53 because the mutated molecule is associated with high nuclear and cytoplasmic concentrations of the p53 protein (Finlay 1988). p53 is an attractive target for adaptive immune response because the intracellular concentration of nonmutated p53 in healthy cells is very low (Zambetti 1993; Reich 1984). This means that healthy cells expressing non-mutant p53 will most likely escape an enhanced immune response to over-expressed mutant p53 (Offringa 2000).

p53, like most tumor associated antigens that are recognizable by the cellular arm of the immune system, is an autoantigen (Rosenberg 2001). The fact that p53 is an autoantigen widely expressed throughout development (Schmid 1991), coupled with the fact that the majority of mutated p53 being expressed in tumors has the same structure as the wild type protein, means that tumor-expressed p53 is likely to be tolerated as a self-protein by the immune system. This tolerance, which has been shown by functional and tetramer studies in mice to exist at the cytotoxic T lymphocyte level (CTL) (Theobald 1997; Erdile 2000), limits the effectiveness of p53-directed immunotherapies. To be successful, an effective immunotherapy must overcome this tolerance without also inducing autoimmunity against normal cells and tissues (Theobald 1997; Erdile 2000; Hernandez 2000). Small numbers of self-reacting T cells escape during the processes involved in the immune tolerance.

Tumors overexpressing p53 have been eliminated in murine models by the systemic administration of epitope specific CTL (Vierboom 2000a; Vierboom 2000b; Vierboom 1997; Hilburger 2001), epitope pulsed dendritic cells (DC) (Mayordomo 1996), or mutant p53 epitope with IL-12 (Noguchi 1995). Each of these strategies has considerable drawbacks with regards to clinical applicability. CTL infusion and infusion of epitope pulsed dendritic cells are time consuming and expensive, because the isolation, culturing, and reinfusion of cells must be performed individually for each patient. Conversely, in order to produce any effect, the cell-free vaccination strategies previously used required either intratumoral injections or vaccination prior to tumor challenge, neither of which represents a practical approach in the clinical setting. There is thus a need for simplified, efficient, and widely applicable immunotherapeutic strategies in the treatment of cancer.

SUMMARY OF THE INVENTION

The p53 gene product is overexpressed in a majority of cancers, making it an ideal target for cancer immunotherapy. The efficacy of these therapies has been limited, however, by the fact that tumor-expressed p53 is likely to be tolerated as a self-protein by the immune system. The present invention is based on the discovery that this self-tolerance can be overcome by administration of recombinant MVA containing a nucleic acid that encodes p53 (rMVAp53). Administration of p53 is shown to greatly decrease tumor development, tumor growth, and mortality in mice challenged with a variety of malignant cell types. It is also shown that the therapeutic effects of rMVAp53 are enhanced by administration of a CTLA-4 blocker or CpG oligodeoxynucleotide (CpG ODN) immunomodulator. This enhancement is greatest when both immunomodulators are administered. The present invention provides a recombinant MVA composition for use in the treatment of cancer, a method of treating cancer using this composition, and a kit for administration of the composition.

In a first aspect, the present invention provides a composition comprising recombinant MVA that contains a nucleic acid encoding p53. Preferably, the p53 encoded by the recombinant MVA is wt human p53. According to the present invention, the composition may also contain a CTLA-4 blocker and/or a CpG ODN.

In another aspect, the present invention provides a method for treating a subject having a p53-expressing malignancy. This method is based on administration of a recombinant MVA containing a nucleic acid that encodes p53. Preferably, the method also calls for administration of a CTLA-4 blocker and/or CpG ODN as an immunomodulator. In a third aspect, the present invention provides a kit for treating a p53-expressing malignancy. This kit contains a recombinant MVA containing a nucleic acid that encodes p53, and may also contain a CTLA-4 blocker and/or CpG ODN as an immunomodulator. In a final aspect, this invention provides for an MVA recombination plasmid containing a nucleic acid insert that encodes wt human p53.

DETAILED DESCRIPTION

Figure 1:
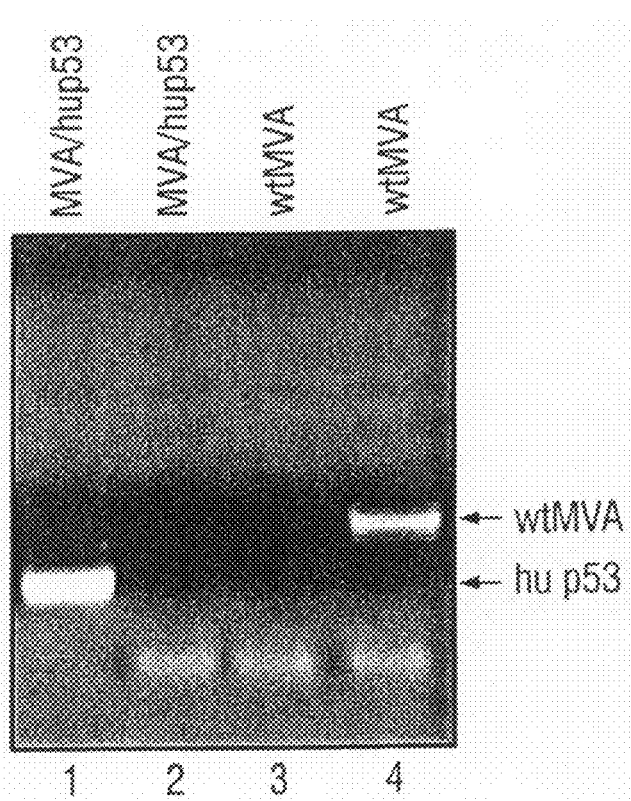
FIG. 1: PCR analysis of the pLW22-hup53 construct. rMVAhup53 injected (lanes 1, 2) and wtMVA infected (lanes 3, 4) BHK cells were subjected to total DNA extraction and PCR amplification using wtMVA (lanes 2, 4) or hup53 (lanes 1, 3) specific primers. The rMVAmup53 product was shown to have no contaminating wtMVA.

The present invention is based on the discovery that self-tolerance to a protein expressed in both normal and cancerous cells can be overcome, and that a strong anti-tumor immune response can be generated without the requirement for intratumoral administration and without the production of systemic toxicity or auto-immunity. The invention provides novel cell-free compositions and methods for the generation of effective immune responses against a wide variety of human malignancies, independent of the subject's haplotype or genotype. The examples discussed below demonstrate that vaccination with a modified vaccinia Ankara vector engineered to express either wild type murine or wild type human p53 (rMVAmup53 or rMVAhup53) stimulates a vigorous p53-specific CTL response. This response can be enhanced by the co-administration of an immunomodulator consisting of a CTLA-4 blocker and/or CpG ODN.

MVA virus (GenBank Accession Number U94848) is a variant of the Ankara strain of vaccinia virus that was derived by over 570 serial passages on primary chicken embryo fibroblast. Several properties of MVA as an attenuated poxvirus make it ideal for the generation of a therapeutic response to tumors expressing p53. One advantage of MVA is that it is able to efficiently replicate its DNA in mammalian cells, yet it is avirulent and does not propagate. This trait is the result of losing two important host range genes among at least 25 additional mutations and deletions that occurred during its passages through chicken embryo fibroblasts (Meyer 1991; Antoine 1998). In contrast to NYVAC (attenuated Copenhagen strain) and ALVAC (host range restricted avipox), both early and late transcription in MVA are unimpaired, allowing for continuous gene expression throughout the viral life cycle (Carroll 1997a; Carroll 1997b; Blanchard 1998; Sutter 1992). MVA has been found to be more immunogenic than the Western Reserve (WR) strain, and can be used in conditions of pre-existing poxvirus immunity (Ramirez 2000a; Ramirez 2000b). The favorable clinical profile of MVA as a recombinant vaccine delivery vehicle is buttressed by its benign safety profile as a smallpox vaccine in Europe in the late 1970's (Mayr 1999; Mayr 1978). MVA was administered to over 120,000 high-risk individuals, including the aged and very young, without serious side effects (Mayr 1978). More recently, MVA has also been administered to immunocompromised non-human primates without adverse outcome (Stittelaar 2001). This is in stark contrast to other vectors, such as retroviruses and adenoviruses, which pose documented risks to the human host. Immunotoxicity of the vector, adjuvant, or immunomodulator used is a particular point of concern in the immunotherapy of cancer, as most cancer patients are severely immunocompromised due to chemotherapy, radiation, or the immunosuppressive effects of the cancer itself. MVA was first developed into a vaccine vehicle in the early 1990's, after it became clear that non-attenuated poxviruses such as the WR strain could not be safely administered to immunocompromised individuals (Redfield 1987; Collier 1991). In summary, the potency of MVA as an expression vector combined with its safety profile in primates and humans make it highly attractive as a delivery system for cancer genes.

Construction of rMVAmup53 and rMVAhup53 is achieved by recombinant DNA techniques that are well known in the art (Sambrook et al., Molecular Cloning, Cold Spring Harbor Laboratory, 2001; Ausubel et al., Current Protocols in Molecular Biology, John Wiley & Sons, 1986 and 2000). The coding sequence of wild type p53 can be conveniently obtained by RT-PCR using p53-specific primers. These primers hybridize to DNA and serve as initiation sites for DNA synthesis. Nucleotide primers are designed to bind at separate sites on opposing duplex strains, thereby defining the intervening sequence as the portion to be amplified. Nucleic acid molecules to be employed as primers will generally include at least a 10 base pair sequence complementary to the DNA segment to be amplified. Primer selection is well known to those of skill in the art. Primers for the amplification of wt mup53 or wt hup53 can be designed to contain appropriate restriction sites for subcloning into a suitable MVA recombination plasmid, such as pMCO3, pLW22, pLW51, pUCII LZ or other MVA transfer vectors well known in the art. The recombination plasmid contains sequences necessary for expression of the foreign gene insert, as well as the flanking sequences necessary for homologous recombination into a chosen site of deletion in the MVA genome. To generate recombinant MVA virus, cells are infected with MVA virus and transfected with the recombination plasmid containing the foreign gene insert. After homologous recombination between virus and plasmid is allowed to occur, recombinant MVA expressing the inserted gene is isolated.

Cellular expression of p53 protein following infection with rMVAmup53 or rMVAhup53 was analyzed to determine the fidelity and extent of its expression from recombinant virus. Meth A cells, which overexpress mutated p53, were used as a positive control, and HCMV IE1 exon4 rMVA infected BHK cells were used as a negative control. Western blot analysis revealed abundant p53 expression by cells infected with rMVAmup53 or rMVAhup53, as well as by Meth A cells. No detectable expression of p53 by HCMV IE1 exon 4-rMVA infected BHK cells was observed. High levels of p53 expression by rMVAp53 infected BHK cells was also observed by fluorescence microscopy. The high level of p53 expression exhibited by rMVAmup53 and rMVAhup53 compared to other viral and cellular forms demonstrates its usefulness in vaccination protocols.

In animal experimental models, MVA based vaccines stimulate tumor specific CTL activity (Espenschied 2003; Drexler 1999) and effect regression of established tumors (Espenschied 2003; Carroll 1997b; Mulryan 2002; Rosales 2000). There are numerous advantages to immunization with whole protein expressed in MVA. In contrast to peptide immunization, multiple epitopes can be expressed, and a polyclonal host response can be stimulated. Antigen-specific cognate help, which is essential to the propagation of a CTL response, can be achieved through expression of a protein in MVA. In addition, expression of whole protein can result in the stimulation of responses to otherwise cryptic epitopes. Immunization with recombinant viruses may also avoid the need for a complex and expensive approach involving the expansion and adoptive transfer of antigen-specific cells, or the need to generate an individualized vaccine for a particular cancer patient. This advantage of a recombinant vaccine approach may encourage more widespread clinical use to prevent recurrence in patients with earlier stages of disease.

In vitro experiments were run to determine whether vaccination with rMVAmup53 could break p53 tolerance, resulting in the generation of p53-specific CTL. Splenocytes were harvested from mice following a single intraperitoneal (i.p.) vaccination with rMVAmup53, and restimulated in vitro with p53 over-expressing cells. The splenocytes recognized and lysed wt p53 over-expressing targets. In contrast, splenocytes from mice vaccinated with rMVApp65, which stimulates vigorous pp65 specific CTL responses, did not recognize the p53 over-expressing targets, demonstrating the specificity of the lymphocyte response. rMVAmup53 vaccination can also stimulate CTL recognition of Meth A cells, which express mutated p53. Restimulated splenocytes from mice vaccinated with rMVAmup53 recognized mutant p53 over-expressing Meth A, whereas control mice vaccinated with rMVApp65 did not.

Since a single vaccination with rMVAmup53 resulted in enhanced CTL response, there was sufficient justification to examine the effect of rMVAmup53 vaccination on the growth of Meth A tumor cells in vivo. Administration of rMVAmup53 was shown to inhibit the outgrowth of murine sarcoma Meth A, an immunogenic tumor cells line that overexpresses mutant p53. Mice inoculated with a lethal dose of Meth A tumor cells and vaccinated with rMVAmup53 by i.p. injection three days later exhibited slower tumor growth and higher survival rates than control animals. A majority of the vaccinated mice failed to develop tumors entirely, and these mice were resistant to rechallenge with Meth A after 52 days (Espenschied 2003).

The above results demonstrate the efficacy of a novel rMVAmup53 cell-free vaccine at targeting p53 expressed by a malignant tumor. Additional experiments were performed to determine whether this effect could be enhanced by addition of a CTLA4 blocker or CpG ODN immunomodulator. Immunization with vaccinia viral constructs results in the uptake and presentation of viral proteins by DC (Norbury 2002). In draining lymph nodes, the DC present antigen to naïve $CD8^+$ T cells, resulting in T cell activation and the subsequent propagation of an immune response (Norbury 2002). Immunomodulator experiments were designed to determine the feasibility of augmenting the response to rMVAp53 by addressing both the initiation of the response and its propagation.

One potent strategy for optimizing tumor vaccines involves manipulating negative regulation of T cell responsiveness by using a molecule that blocks CTLA4 engagement with ligand, a phenomenon referred to as "CTLA-4 blockade." CTLA-4 is a cell surface receptor found on T cells. Activation of CTLA4 leads to inhibition of T cell responses. CTLA-4 plays a significant role in regulating peripheral T-cell tolerance by interfering with T-cell activation through both passive and active mechanisms (Egen 2002). Application of a CTLA-4 blocker in combination with cancer vaccines expressing tumor associated autoantigens can, in some cases, result in tumor rejection along with breaking of tolerance, albeit with the concomitant induction of autoimmunity (Espenschied 2003; Hurwitz 2000; van Elsas 1999). In vitro, CTLA-4 blockade lowers the T-cell activation threshold and removes the attenuating effects of CTLA-4. CTLA-4 blockade also inhibits Treg cell activity in vivo (Read 2000). When combined with GM-CSF producing tumor cell vaccines, CTLA-4 blockade results in rejection of established poorly immunogenic melanoma, mammary carcinoma, and prostate carcinoma grafts (Hurwitz 1998; Hurwitz 2000; van Elsas 1999). This occurs through a process, which involves breaking tolerance to tumor associated antigens. CTLA-4 blocking agents are molecules that specifically bind to the CTLA-4 receptor and interfere with the binding of CTLA-4 to its counter-receptors. A CTLA-4 blocking agent can be a monoclonal or polyclonal antibody, a fragment of an antibody, a peptide, a small organic molecule, a peptidomimetic, a nucleic acid such as interfering RNA (iRNA) or antisense molecule, an aptamer, or any domains from CTLA-4 ligands, including members of the B7 family of CTLA-4 ligands, wherein said ligands can be preferably synthesized as recombinant soluble proteins capable of binding CTLA-4 present on immune cells and blocking CTLA-4 function. Anti-CTLA-4 antibodies may be generated by immunizing a host animal with CTLA-4 protein or with cells expressing CTLA-4. Monoclonal antibodies to CTLA-4 (anti-CTLA-4 mAb) can be produced by conventional techniques, namely fusing a hybridoma cell with a mammalian immune cell that produces anti-CTLA-4 antibody. Mammalian cells used to generated anti-CTLA-4 mAb may include rat, mouse, hamster, sheep, or human cells. Anti-CTLA-4 mAbs may be purified from hybridoma cell supernatants or from ascites fluid. Anti-CTLA-4 antibodies may be human antibodies generated using transgenic animals (Bruggemann 1991; Mendez 1997) or human immunoglobulin phage display libraries (Winter 1994). Anti-CTLA-4 antibodies also encompasses chimeric and humanized (or "reshaped") antibodies. Chimeric antibodies to CTLA-4 may be generated through recombinant methods to contain the CTLA-4 binding domain of a non-human antibody and the constant domain of a human antibody. Humanized antibodies to CTLA-4 may be generated by recombinant methods to contain only the CDR regions of non-human anti-CTLA-4 antibodies placed on a human antibody structural framework (Jones 1986; Low 1986). Individual residues within the non-human region may be substituted with residues from the human antibody framework. Conversely, individual residues within the human antibody framework may be substituted with residues from the non-human antibody (Foote 1992). Such substitutions may be used to increase the binding capabilities of the humanized antibody or to decrease the immune response against the antibody. Humanized antibodies to CTLA-4 can be the product of an animal having transgenic human immunoglobulin constant region genes. They can also be engineered by recombinant DNA techniques to substitute the $C_H1$, $C_H2$, $C_H3$, hinge domains, or other domains with the corresponding human sequence, by methods known in the art.

Oligodeoxynucleotides containing unmethylated CpG (cytosine-phosphate-guanine) motifs are potent immunostimulatory agents that can enhance vaccine potency (Krieg 2002). Immune activation by CpG ODN initiates with specific binding to the Toll-like Receptor-9 (TLR9) in B cells and plasmacytoid dendritic cells (Krieg 2002). TLR9 ligation in DC results in secondary activation of lymphocyte, macrophage, monocyte, natural killer (NK), and T-cell populations through the elaboration of cytokines generating a $T_H1$ cytokine milieu (Krieg 2003). This results in increased NK activity, improved antigen presentation, and T cell help that can augment both humoral and cell-mediated immune responses. In addition, TLR9 ligation results in the production of IL-6 by DCs, which helps overcome the suppressive effect of $CD4^+$ $CD25^+$ Treg cells (Pasare 2003). Administration of CpG ODN alone has been shown to exert modest anti-tumor effects in a number of murine tumor models (Carpentier 1999; Kawarada 2001; Ballas 2001; Baines 2003; Sharma 2003). CpG ODN has been shown to be an effective adjuvant for a variety of experimental tumor vaccines in mice. It is at least as effective as Freund's adjuvant, but with higher $T_H1$ activity and less toxicity (Chu 1997; Weiner 1997). CpG ODN can enhance the effect of peptide (Davila 2000; Stern 2002), protein (Kim 2002), DC (Heckelsmiller 2002), idiotype (Baral 2003), and GM-CSF secreting tumor cell vaccines (Sandler 2003). The ability of CpG ODN to prime for $T_H1$ responses and stimulation of NK cells probably accounts for the immunomodulator activity in these vaccine approaches and in those described below.

To determine whether administration of a CTLA-4 blocking agent in conjunction with rMVAmup53 vaccination would be beneficial or would induce autoimmune disease, a monoclonal antibody specific to CTLA-4 (anti-CTLA-4 mAb) was used. Vaccination with rMVAmup53 and anti-CTLA-4 mAb was shown to effect the rejection of established, palpable Meth A tumors. Mice injected with a high dose of Meth A and vaccinated with rMVAmup53 and anti-CTLA-4 mAb (9H10) only after formation of a palpable tumor nodule exhibited complete tumor regression and lasting tumor immunity. In vivo antibody depletion studies confirmed that this antitumor effect was primarily $CD8^+$, and to a lesser extent $CD4^+$, dependent.

To establish that the above results were not tumor specific, vaccination with rMVAmup53 and a CTLA-4 blocker immunomodulator was performed on mice injected with 11A-1 or MC-38 tumor cells. 11A-1 is a rapidly growing malignant cell line that is poorly immunogenic. MC-38 is a colon carcinoma cell line. Mice injected with 11A-1 or MC-38 tumor cells and vaccinated 4 days later with rMVAmup53 and anti-CTLA-4 mAb rejected their tumors. Similar results were seen when the anti-CTLA-4 mAb was replaced with CpG ODN. The majority of mice treated with rMVAmup53 and CpG ODN did not develop palpable tumors and developed lasting tumor immunity, rejecting a rechallenge at 60 days.

The potential additive effect of the anti-CTLA-4 mAb and CpG ODN immunomodulators was examined by administering both immunomodulators in conjunction with rMVAmup53 to 11A-1 injected mice with palpable tumors. Tumor rejection and prolonged survival were observed in the majority of mice receiving both immunomodulators in conjunction with rMVAmup53. Mice that received only one immunomodulator in conjunction with rMVA, on the other hand, all eventually succumbed to tumor growth. Not only did the combination of both immunomodulators provide a greater benefit than either immunomodulator acting alone, but their combined benefit was greater than the simple addition of the effects of the immunomodulators. Similar results were seen in mice bearing MC 38 tumors.

To determine the efficacy of a recombinant MVA containing a human p53 sequence, rMVAhup53 was administered to hupki mice injected with 4T1 (H-$2^d$) cells that had been transfected with human p53. 4T1 (H-$2^d$) is a murine breast carcinoma cell line. Mice were vaccinated with rMVAhup53 6 days after injection with 4T1 cells, and vaccinated again ten days later. During the second vaccination, CpG ODN and anti-CTLA-4 mAb were administered as well. Mice treated with vaccine and both immunomodulators exhibited a statistically significant improvement in survival.

The above results demonstrate the efficacy of a novel rMVAmup53 or rMVAhup53 cell-free vaccine at eliciting an immune response targeting p53 in a variety of malignant tumor types, as well as the efficacy of anti-CTLA-4 mAb and CpG ODN as immunomodulators to this vaccine. Accordingly, the present invention provides a composition comprising a recombinant MVA virus engineered to express p53 (rMVAp53). The present invention further provides an immunotherapeutic method for eliciting an immune response against a wide range of p53-expressing malignancies by administering rMVAp53

Introduction of rMVAp53 into a subject can be performed by any procedure known to those skilled in the art, and is not dependent on the location of tumor nodules for efficacy or safety. Thus, rMVAp53 can be administered by intravascular, subcutaneous, peritoneal, intramuscular, intradermal or transdermal injection, to name a few possible modes of delivery. rMVAp53 can be prepared as a formulation at an effective dose in pharmaceutically acceptable media, such as normal saline, vegetable oil, mineral oil, PBS, etc. Therapeutic preparations may include physiologically tolerable liquids, gel or solid carriers, diluents, adjuvants and excipients. Additives may include bactericidal agents, additives that maintain isotonicity (e.g., NaCl, mannitol), additives that maintain chemical stability (e.g., buffers, preservatives) and other ingredients. For parenteral administration, the rMVAp53 may be formulated as a solution, suspension, emulsion or lyophilized powder in association with a pharmaceutically acceptable parenteral vehicle. Liposomes or non-aqueous vehicles, such as fixed oils, may also be used. The formulation may be sterilized by techniques known in the art.

The rMVAp53 formulation can be further enhanced with a costimulator, such as a cytokine, tumor antigen, an antigen derived from a pathogen, or any immunomodulator. The costimulator can be any agent that directly or indirectly stimulates an immune response in combination with the rMVAp53, and may be selected for its ability to modulate APC or T-cell function. For example, MVA can be engineered to express GM-CSF, IL-12, or other stimulatory cytokines to produce a costimulator, and the combination of rMVAp53 and costimulator (here: MVA expressing the stimulatory cytokine) can be introduced into the subject. The treatment may be performed in combination with administration of cytokines that stimulate antigen presenting cells, such as granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), and others well known in the art. Other costimulators include cytokine-transduced tumor cells, such as tumor cells transduced with GM-CSF, as well as tumor cells that have been irradiated and/or treated with a chemotherapeutic agent ex vivo or in vivo. Chemotherapeutic or radiotherapeutic agents are further examples of costimulators. Thus, rMVAp53 can be administered in conjunction with a variety of costimulators known to those of skill in the art.

The formulation is administered at a dose effective to increase the response of T cells to antigenic stimulation. The determination of the T cell response will vary with the condition that is being treated. Useful measures of T cell activity are proliferation, the release of cytokines, including, IL-2, IFNγ, TNFα, etc; T cell expression of markers such as CD25 and CD69; and other measures of T cell activity as known in the art. The dosage of the therapeutic formulation will vary widely, depending upon the stage of the cancer, the frequency of administration, the manner or purpose of the administration, the clearance of rMVAp53 from the subject, and other considerations. The dosage administered will vary depending on known factors, such as the pharmacodynamic characteristics of the particular agent, mode and route of administration, age, health and weight of the recipient, nature and extent of symptoms, concurrent treatments, frequency of treatment, and effect desired. The dose may be administered as infrequently as weekly or biweekly, or fractionated into smaller doses and administered daily, semi-weekly, etc., to maintain an effective dosage level.

Generally, a daily dosage of active ingredient can be about $10^6$-$10^{11}$ IU (infectious units)/kg of body weight. Dosage forms suitable for internal administration generally contain from about $10^6$ to $10^{12}$ IU of active ingredient per unit. The active ingredient may vary from 0.5 to 95% by weight based on the total weight of the composition. In some cases it may be desirable to limit the period of treatment due to excessive T cell proliferation. The limitations will be empirically determined, depending on the response of the patient to therapy, the number of T cells in the patient, etc. The number of T cells may be monitored in a patient by methods known in the art, including staining with T cell specific antibodies and flow cytometry.

In a preferred embodiment of the present invention, rMVAp53 is administered in conjunction with an immunomodulator, specifically a CTLA-4 blocking agent or a CpG ODN. The combined administration of rMVAp53 and the CTLA4 blocking agent anti-CTLA4 mAb is unexpectedly potent in producing regression of advanced tumors that are rapidly lethal when left untreated. The same is true of the combined administration of rMVAp53 and CpG ODN. Potency is even greater when both immunomodulators are administered in conjunction with rMVAp53. In addition, the anti-CTLA4 mAb CpG ODN immunomodulators are non-toxic to the subject, and capable of generating long lasting immunity to lethal challenges with tumor cells when administered in conjunction with rMVAp53. As is the case with rMVAp53 alone, introduction of rMVAp53 plus anti-CTLA-4 mAb and/or CpG ODN into a subject can be performed by any procedure known to those skilled in the art, and is not dependent on the location of tumor nodules for efficacy or safety. Thus, rMVAp53, anti-CTLA4 mAb, and CpG ODN can be administered by intravascular, subcutaneous, peritoneal, intramuscular, intradermal or transdermal injection, to name a few possible modes of delivery. rMVAp53, anti-CTLA-4 mAb, and CpG ODN can be administered together, separately, or sequentially, in any order, by the same route of administration or by different routes. rMVAp53 plus anti-CTLA-4 mAb and/or CpG ODN can be prepared as formulations at an effective dose in pharmaceutically acceptable media, for example normal saline, vegetable oil, mineral oil, PBS, etc. Therapeutic preparations may include physiologically tolerable liquids, gel or solid carriers, diluents, adjuvants and excipients. Additives may include bactericidal agents, additives that maintain isotonicity, e.g. NaCl, mannitol; and chemical stability, e.g. buffers and preservatives and other ingredients. rMVAmup53 plus anti-CTLA-4 mAb and/or CpG ODN may be administered as a cocktail or as single agents. For parenteral administration, anti-CTLA-4 mAb and CpG ODN may be formulated as a solution, suspension, emulsion or lyophilized powder in association with a pharmaceutically acceptable parenteral vehicle. Liposomes or non-aqueous vehicles, such as fixed oils, may also be used. The formulation may be sterilized by techniques as known in the art.

The rMVAp53 plus anti-CTLA-4 mAb and/or CpG ODN combination can be further enhanced with a costimulator such as a cytokine, tumor antigen, or antigen derived from a pathogen. A costimulator can be any agent that directly or indirectly stimulates an immune response in combination with rMVAp53 or in combination with rMVAp53 plus anti-CTLA-4 mAb and/or CpG ODN. For example, MVA can be engineered to express GM-CSF, IL-12, or other stimulatory cytokine to produce a costimulator, and the combination of rMVAp53 and costimulator (here: MVA expressing the stimulatory cytokine), or rMVAp53 plus anti-CTLA-4 mAb and/or CpG ODN and costimulator can be introduced into the subject. The treatment may be performed in combination with administration of cytokines that stimulate antigen presenting cells, such as granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12) and others well known in the art. Other costimulators include cytokine-transduced tumor cells such as tumor cells transduced with GM-CSF, or tumor cells that have been irradiated and/or treated with a chemotherapeutic agent ex vivo or in vivo. Chemotherapeutic or radiotherapeutic agents are further examples of costimulators. Thus, rMVAp53 either alone or in combination with anti-CTLA-4 mAb and/or CpG ODN can be administered in conjunction with a variety of costimulators known to those of skill in the art.

The dosage of the therapeutic formulation will vary widely, depending upon the stage of the cancer, the frequency of administration, the manner or purpose of the administration, and the clearance of rMVAp53, anti-CTLA-4 mAb, and CpG ODN from the subject, among other considerations. The dosage administered will vary depending on known factors, such as the pharmacodynamic characteristics of the particular agent, mode and route of administration, age, health and weight of the recipient, nature and extent of symptoms, concurrent treatments, frequency of treatment and effect desired. The dose may be administered as infrequently as weekly or biweekly, or fractionated into smaller doses and administered daily, semi-weekly, etc. to maintain an effective dosage level.

Generally, a daily dosage of active ingredient (antibody) can be about 0.1 to 100 mg/kg of body weight. Dosage forms suitable for internal administration generally contain from about 0.1 mg to 500 mgs of active ingredient per unit. The active ingredient may vary from 0.5 to 95% by weight based on the total weight of the composition. In some cases it may be desirable to limit the period of treatment due to excessive T cell proliferation. The limitations will be empirically determined, depending on the response of the patient to therapy, the number of T cells in the patient, etc. The number of T cells may be monitored in a patient by methods known in the art, including staining with T cell specific antibodies and flow cytometry. The formulation is administered at a dose effective to increase the response of T cells to antigenic stimulation. The determination of the T cell response will vary with the condition that is being treated. Useful measures of T cell activity are proliferation, the release of cytokines, including. IL-2, IFNγ, TNFα, etc; T cell expression of markers such as CD25 and CD69; and other measures of T cell activity as known in the art.

The present invention further provides a kit that will allow the artisan to prepare an immunotherapeutic regimen for eliciting an immune response against a p53-expressing malignancy. An example of a kit comprises rMVAp53, a CTLA-4 blocking agent and/or a CpG ODN, and instructions for using these compounds to elicit an immune response against a p53-expressing malignancy in a subject. The kit may further comprise one or more pharmaceutically acceptable carriers. When administered, the compositions of the kit are administered in pharmaceutically acceptable preparations. The terms administration, administering, and introducing refer to providing the compositions of the invention as a medicament to an individual in need of treatment or prevention of a p53-expressing malignancy. This medicament, which contains compositions of the present invention as the principal or active ingredients, can be administered in a wide variety of therapeutic dosage forms in the conventional vehicles for topical, oral, systemic, local, and parenteral administration. Thus, the kits of the invention provide compositions for parenteral administration that comprise a solution of the compositions dissolved or suspended in an acceptable carrier, preferably an aqueous carrier. The compositions may contain pharmaceutically acceptable auxiliary substances as required to approximate physiological conditions, such as pH adjusting and buffering agents, tonicity adjusting agents, wetting agents and the like, including sodium acetate, sodium lactate, sodium chloride, potassium chloride, calcium chloride, sorbitan monolaurate, triethanolamine oleate, and many others. Actual methods for preparing compounds for parenteral administration will be known or apparent to those skilled in the art and are described in more detail in, for example, Remington: The Science and Practice of Pharmacy ("Remington's Pharmaceutical Sciences") Gennaro A R ed. $20^{th}$ edition, 2000: Williams & Wilkins PA, USA, which is incorporated herein by reference.

Such preparations may routinely contain pharmaceutically acceptable concentrations of salt, buffering agents, preservatives, compatible carriers, supplementary immune potentiating agents such as adjuvants and cytokines and optionally other therapeutic agents. All the preparations of the invention are administered in effective amounts. An effective amount is that amount of a pharmaceutical preparation that alone, or together with further doses, stimulates the desired response. In the case of treating cancer, the desired response is inhibiting the initiation or progression of the cancer, or producing regression of the cancer. This may involve only slowing the progression of the disease temporarily, although more preferably, it involves halting the progression of the disease permanently. These desired responses can be monitored by routine methods or can be monitored according to diagnostic methods of the invention discussed herein. It is believed that doses of immunogens ranging from $10^4$ IU/kilogram to $10^{11}$ IU/kilogram, depending upon the mode of administration, would be effective. The preferred range is believed to be between $10^6$ IU and $10^9$ IU per kilogram. The absolute amount will depend upon a variety of factors, including the combination selected for administration, whether the administration is in single or multiple doses, and individual patient parameters including age, physical condition, size, weight, and the stage of the disease. These factors are well known to those of ordinary skill in the art and can be addressed with no more than routine experimentation.

The following examples are provided to better illustrate the claimed invention and are not to be interpreted as limiting the scope of the invention. To the extent that specific materials are mentioned, it is merely for purposes of illustration and is not intended to limit the invention. Unless otherwise specified, general cloning procedures, such as those set forth in Sambrook et al., Molecular Cloning, Cold Spring Harbor Laboratory (2001), Ausubel et al. (Eds.) Current Protocols in Molecular Biology, John Wiley & Sons (1986, 2000) are used. One skilled in the art may develop equivalent means or reactants without the exercise of inventive capacity and without departing from the scope of the invention.

It will be understood that many variations can be made in the procedures herein described while still remaining within the bounds of the present invention. Likewise, it is understood that, due to the degeneracy of the genetic code, nucleic acid sequences with codons equivalent to those disclosed will encode functionally equivalent or identical proteins as disclosed herein. It is the intention of the inventors that such variations are included within the scope of the invention.

EXAMPLES

Materials and Methods

Animals

Female 6-8 week old Balb/c, C57BL/6, B6.129S2-IL6$^{tm1Kopf}$ (IL-6$^{-/-}$, and IFN-γ knock out (IFN-γ$^{KO}$) mice on the Balb/c background were obtained from The Jackson Laboratory (Bar Harbor, Me.). TLR9$^{-/-}$ mice were a kind gift from Dr. Shizuo Akira (Osaka University, Osaka, Japan). Mice were maintained in a specific pathogen-free environment. All studies were approved by the Research Animal Care Committee of the City of Hope National Medical Center, and performed under the AAALAC guidelines.

Cell Lines

CV-1 (Kit 1965), TK$^-$ (Berson 1996), and Baby Hamster Kidney cells (BHK-21) (Macpherson 1962) were purchased from American Type Culture Collection (ATCC) (Manassas, Va.), and grown in MEM supplemented with non-essential amino acids, L-glutamine, and 10% FCS. 11A-1 (Selvanayagam 1995) was a kind gift from Dr. R. L. Ullrich (University of Texas Medical Branch, Galveston, Tex.). Hek 293 cells and p53null 10.1 cells were kind gifts from Dr. K. K. Wong and Dr. Susan Kane (City of Hope National Medical Center, Duarte, Calif.). MC-38 (Tan 1976) was a kind gift from Dr. S. A. Rosenberg (National Cancer Institute, Bethesda, Md. Meth A sarcoma cells (Meth A) (DeLeo 1977) were a kind gift from Dr. L. J. Old (Memorial Sloan-Kettering Cancer Center, New York, N.Y.). Meth A was passaged as an ascitic tumor. Cells were harvested, counted and washed with PBS prior to use. The characteristics of the Meth A, 11A-1, and MC-38 tumor cell lines are summarized in the following table:

| Cell line | Tumor | MHC Background | P53 mutation position(s) |
|---|---|---|---|
| Meth A | Fibrosarcoma | H-2$^d$ | 132, 168, 234 |
| 11A-1 | Mammary cell carcinoma | H-2$^d$ | 173 |
| MC-38 | Colon carcinoma | H-2$^b$ | 242 |

Antibodies

Anti-CD4 (GK1.5) (Dialynas 1983) and anti-NK1.1 (PK136) (Koo 1984) were purchased from ATCC. Anti-CD8 (H35) (Miconnet 2001) and anti-CTLA-4 mAb (9H10) (Krummel 1995) were kind gifts from James P. Allison (University of California, Berkeley, Calif.). Antibodies were produced using a CELLine Device (BD Biosciences, Bedford, Mass.). IgG antibodies were purified by absorbance over protein G-Sepharose (Amersham, Uppsala, Sweden) followed by elution with 0.1M Glycine-HCl, pH 2.7. The product was then dialyzed against phosphate-buffered normal saline (PBS) and concentrated using a Centriplus centrifugal filter device (Millipore, Bedford, Mass.). Control Syrian Hamster IgG was obtained from Jackson Immuno Research (West Grove, Pa.).

Viral Constructs rMVA Expressing Murine p53 (rMVAmup53):

Wild type MVA (wtMVA) was obtained from Dr. Bernard Moss and Dr. Linda Wyatt (National Institutes of Health Bethesda, Md.). wtMVA stocks for the generation of recombinant MVA (rMVA) containing mup53 are propagated on specific pathogen free chicken embryo fibroblasts (SPF/CEF). The wtMVA stock is titrated by immunostaining, aliquoted, and stored at −80° C.

Murine p53 (mup53) is analogous to human p53, with 80% sequence homology (Halevy 1991; Sukumar 1995). The mRNA coding sequence for full-length wild type mup53 is shown in SEQ ID NO: 1. The level of homology between murine and human p53 makes the murine system an excellent preclinical model for evaluating immunologic approaches for overcoming tolerance to p53. rMVA expressing murine p53 was generated by homologous recombination of wtMVA and a pMCO3 insertion vector containing a murine p53 insert, as described in Espenschied 2003. The entire cDNA of murine wild type p53 was amplified by PCR of mRNA obtained from murine splenocytes. The murine p53 PCR product was ligated into the cloning site of the MVA expression vector pMCO3 (also obtained from Dr. Moss and Dr. Wyatt). This vector contains sequences that insert into deletion III of the MVA genome, and also contains the gus (E. coli B-glucuronidase) operon for screening purposes (Ourmanov 2000). Generation of recombinant MVA was achieved on monolayers of BHK-21 cells (Espenschied 2003). Briefly, BHK-21 cells were transfected with 20 μg of plasmid DNA using Lipofectin (Invitrogen, Carlsbad, Calif.) and infected with wtMVA at an moi of 0.01. The infected cells were incubated for 48 hours, then harvested, pelleted, and subjected to 3 cycles of freeze/thaw and sonication to lyse the cells. rMVA virus expressing murine p53 (rMVAmup53) was screened for gus expression by adding X-GlcA (5-Bromo-4-Chloro-3-indolyl B-D-Glucuronide, Sigma-Aldrich, St Louis, Mo.). After 10 rounds of purification, the rMVAmup53 was expanded on BHK-21 monolayers. The rMVAmup53 titer was determined by immunostaining infected cultures using the Vectastain Elite ABC Kit (Vector Laboratories, Burlingame, Calif.).

rMVA Expressing Human p53 (rMVAhup53):

Two different constructs of rMVA expressing human p53 (rMVAhup53) were made. The mRNA sequence encoding full-length wild type hup53 is shown in SEQ ID NO: 2. The first was made using the pLW51 insertion plasmid, while the second was made using the pLW22 insertion plasmid. wtMVA used to make the first construct was propagated on SPF/CEF. wtMVA used to make the second construct was propagated on BHK-21 (BHK) cells. wtMVA stock was titrated by immunostaining, aliquoted, and stored at −80° C.

pLW51 was used as the insertion plasmid for generating the first rMVAhup53 construct. pLW51 has four important features. First, it contains MVA flanking regions of deletion III that allow it to insert into the deletion III region of MVA via homologous recombination. Second, it contains a color screening marker gene, β-glucoronidase (gus), under control of a vaccinia promoter called $P_{11}$. Third, it contains two direct repeats composed of MVA sequence (designated as DR1 and DR2) flanking the gus screening marker gene to allow the gus gene to be removed from recombinant MVA. Finally, it contains two vaccinia promoters ($P_{SYN}$ and $P_{7.5}$) and two multiple cloning sites (MCS), permitting the insertion of two separate foreign genes under the control of the $P_{SYN}$ and $P_{7.5}$ promoters. The first MCS is behind an early/late $P_{SYN}$ promoter, while the second MCS uses an early/late $P_{mH5}$ promoter. This enables the elimination of the gus marker gene through recombination via a set of direct repeats, which flank it. The generation of the initial rMVA stock is done on CEF utilizing methods that were previously described for BHK cells, with modifications to account for good laboratory practice (GLP) conditions. About 40-50 foci are pulled from the first rounds of screening to ensure that a correct recombinant will be found, after which 5-10 are pulled in each subsequent round. After each round of selection, either immunostaining or immunofluorescence is performed on each plug to make sure that the plug is expressing the hup53 gene. To achieve a virus that will be deleted of the bacterial gene marker, purified rMVA expressing hup53 is plated at low dilution in 24 well plates. Wells that do not have a color reaction demonstrating the gus gene are further analyzed for the presence of the hup53 gene product. This is accomplished by antibody staining using conditions that allow recovery of the virus from the cells. Those wells that exhibit hup53 immunostaining in the absence of a color reaction are further propagated and confirmed to be the correct phenotype. A portion of the viral plug pulled from the final round of screening absent the gus marker is expanded in a 100 mm tissue culture dish of CEF. This is followed by DNA extraction and PCR analysis (discussed below).

pLW22 was used as the insertion plasmid for generating the second rMVAhup53 construct. pLW22 has MVA flanking regions that allow it to insert into MVA via homologous recombination. It also has a color screening marker gene, β-galactosidase. To obtain DNA encoding wt hup53, pHp53B plasmid in E. coli was obtained from the ATCC (#57254). Hup53 was amplified from the pHp53B plasmid using the forward primer of SEQ ID NO: 3 and the reverse primer of SEQ ID NO: 4. Amplified wt hup53 DNA was inserted into the pLW22 vector between restriction sites Pme-1 and Asc-1, generating pLW22-hup53. The plasmid sequence of pLW22-hup53 is shown in SEQ ID NO: 5.

Generation of rMVA was achieved on monolayers of BHK cells. BHK cells were transfected with 20 μg of plasmid DNA using Lipofectin (Invitrogen, Carlsbad, Calif.), and infected with wtMVA at an moi of 0.01. The infected cells were incubated for 48 hours, then harvested, pelleted, and subjected to three cycles of freeze/thaw and sonication to lyse the cells. rMVA expressing hup53 was screened for β-gal expression by adding presence of Bluo-gal™ substrate (Sigma-Aldrich, St Louis, Mo.) (Chakrabarti 1985). After 10 rounds of purification, the rMVAhup53 was expanded on BHK monolayers. The rMVA titer was determined by immunostaining infected cultures using the Vectastain Elite ABC kit (Vector Laboratories, Burlingame, Calif.).

For both constructs, a standard DNA extraction is performed. Ethanol precipitation of 50 μL of the cell lysate resulted in enough DNA to run a PCR reaction to assure the absence of contaminating wtMVA. One set of PCR primers are designed outside the flanking regions of the recombination site for which the gene has been inserted. The presence of unmodified wtMVA sequence will generate a 500 bp PCR product, whereas the insertion of the sequence containing hup53 has a much larger fragment (>6 kb), which is usually difficult to amplify under standard PCR conditions. A second set of PCR primers are designed to amplify a sequence within the hup53 insert. The presence of the hup53 insert will generate a 300 bp PCR product. The PCR samples are run on a 1% agarose gel and analyzed to determine if additional screenings are necessary to remove any remaining wtMVA. Examples of purified MVA containing human p53 have been shown to be absolutely homogenous (FIG. 1).

rMVA Expressing pp65 (rMVApp65):

rMVA expressing pp65 (rMVApp65), a CMV tegument protein, was constructed using techniques similar to those used to construct rMVAmup53 (Gibson).

rVV Expressing Murine p53 or pp65:

Recombinant Western Reserve strain Vaccinia Virus expressing murine wild type p53 or pp65 (rVVp53, rVVpp65) was constructed using published techniques (Diamond 1997).

rAd Expressing Murine p53:

Recombinant adenovirus expressing wild type murine p53 (rAd-mup53) was constructed using the pAd Easy system (He 1998). Both pAd Track-CMV and pAd Easy-1 plasmids were kindly provided by Dr. Bert Vogelstein (Johns Hopkins Oncology Center, Baltimore, Md.). Wild type murine p53 cDNA was cloned into the BgI II and Xba I site of a pAd Track-CMV shuttle vector containing green fluorescent protein (GFP) with a CMV promoter (p53-pAd Track-CMV). The p53-pAd Track-CMV was cotransformed into BJ5183 cells with the pAd Easy-1 plasmid to generate the p53 recombinant adenoviral construct by homologous recombination. The presence of the p53 gene in the recombinants was confirmed by DNA sequencing. The p53 recombinant adenoviral construct was cleaved with Pac I and transfected into HEK-293 cells. rAd-mup53 was harvested 5 days after transfection and p53 protein expression was confirmed by western blot. The adenovirus was expanded on HEK-293 cells and purified by cesium chloride gradient. The purified virus was dialyzed in PBS, titered on HEK-293 cells, and stored at −80° C. in 20% glycerol.

Oligodeoxynucleotides (ODN)

Synthetic ODN 1826 with CpG motifs (SEQ ID NO: 6) and non-CpG ODN 1982 (SEQ ID NO: 7) (Moldoveanu 1998) were synthesized with nuclease-resistant phosphorothioate backbones by Trilink (San Diego, Calif.). The Na$^+$ salts of the ODNs were resuspended at 5 mg ml$^{-1}$ in 10 mM Tris (pH 7.0) 1 mM EDTA and stored as 50 μl aliquots at −20° C. before dilution in aqueous 0.9% sodium chloride solution prior to injection.

Example 1

Expression of Murine p53 Protein by rMVAmup53

Figure 2:
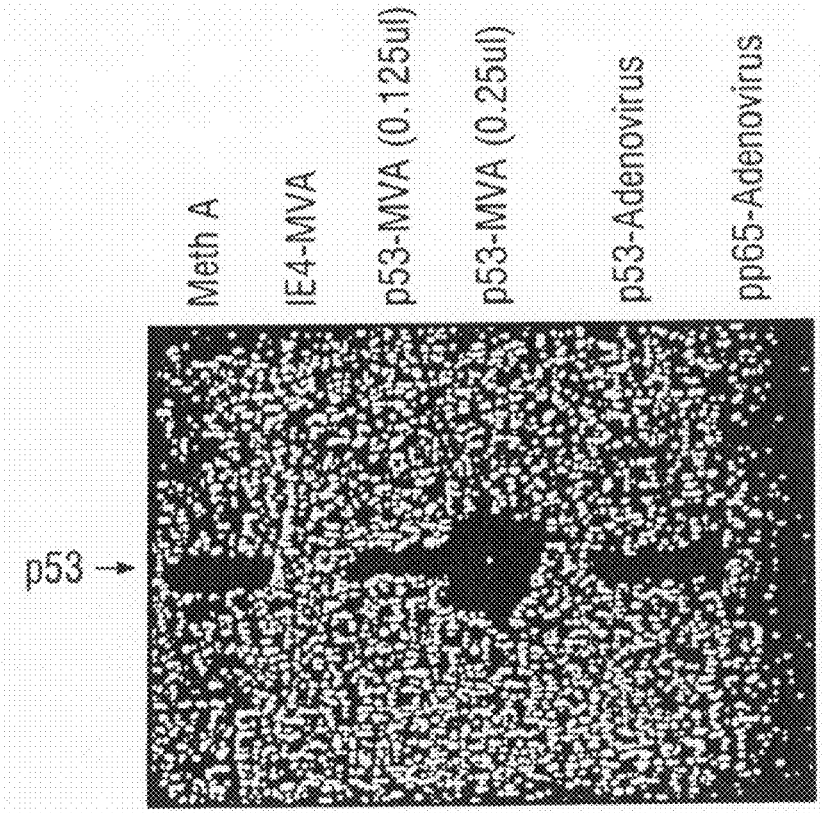
FIG. 2: Expression of mup53 by cells infected with rMVAmup53. Cells infected with rMVAmup53 express mup53 at high levels, confirming that MVA is a suitable vaccine vector. Cell lysates were subjected to SDS-PAGE and Western blotting. The lanes are designated as follows: 1) Meth A, unmanipulated Meth A sarcoma cells, 2) HCMV IE1 exon4-rMVA infected BHK cells, 3-4) rMVAmup53 infected BHK cells (loaded 0.125 ul, 0.25 ul cell lysates respectively), 5) rAdp53, and 6) rAdpp65 infected HEK 293 cells. All lanes were loaded with 20 µl sample unless indicated specifically.

Expression of murine p53 protein following infection with rMVAmup53 was analyzed to determine the fidelity and extent of its expression from recombinant virus. Lysates were prepared from BHK or HEK 293 cells infected with rMVAmup53 and subjected to SDS-PAGE and Western blotting. Standard Western Blotting techniques were performed using an ECL Western Blot Kit (Amersham Pharmacia Biotech, England). The samples were incubated with a purified mouse anti-p53 monoclonal antibody, PAb 122 (Gurney 1980), followed by incubation with a peroxidase labeled goat anti-mouse secondary antibody provided in the ECL Western Blot kit. Western blot analysis of BHK cells infected with rMVAmup53 demonstrates abundant p53 expression (FIG. 2). The remarkable level of expression exhibited by rMVAmup53 compared to other viral and cellular forms demonstrates its usefulness in vaccination protocols. As shown in FIG. 1, the volume on the rMVAmup53 lane is between 80-160 fold less than what was applied to the gel in the other lanes, yet the intensity of the band is several fold higher. This demonstrates a very high level of p53 expression by rMVAmup53. Meth A cells were used as a positive control and BHK cells infected with HCMV IE1 exon 4 rMVA were used as negative controls. Meth A is a Balb/c derived, tumorigenic 3-methyl-cholanthrene-induced sarcoma that over-expresses mutated p53. A 53 kilodalton band was observed in both the p53 overexpressing Meth A sarcoma and the rMVAmup53 infected BHK cells (FIG. 1). This contrasts with the absence of detectable p53 expression in the HCMV IE1 exon 4-rMVA infected BHK cells. Strong p53 expression was also observed by fluorescence microscopy in BHK cells infected with rMVAmup53 (data not shown).

Example 2

In vitro Generation of a p53-Specific CTL Response by rMVAmup53

Figure 3A:
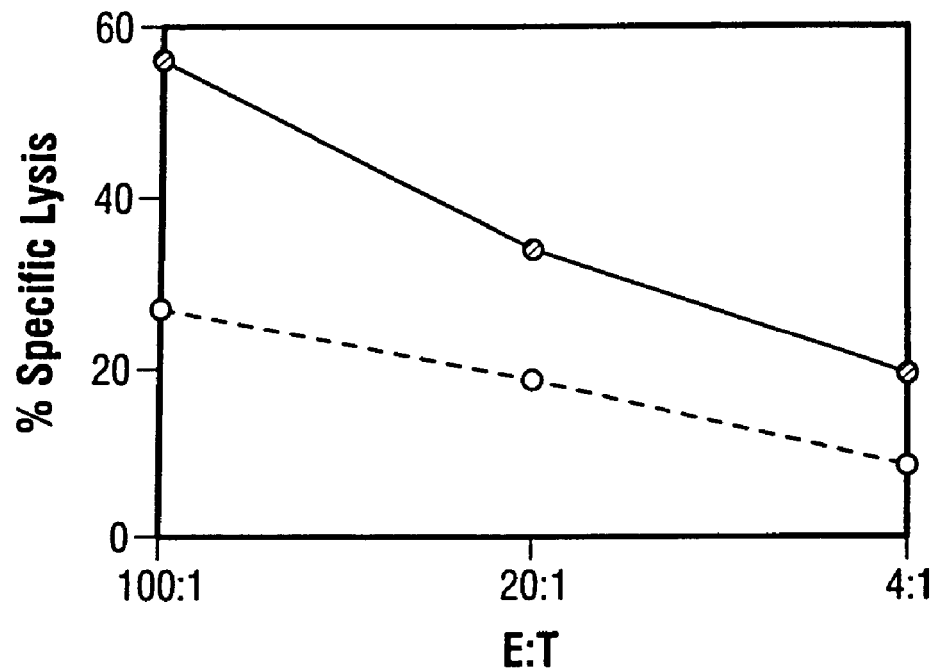
FIG. 3: Generation of a p53-specific CTL response by rMVAmup53 in vitro. A single intraperitoneal (i.p.) vaccination with rMVAmup53 generates p53 specific CTL responses that efficiently kill cells overexpressing p53. (a) Splenocytes from mice treated with rMVAmup53 were harvested at 14 days and restimulated in vitro for 6 days with rAdp53 infected syngeneic LPS blasts. CTL activity was evaluated in a standard 4-h $^{51}$Cr release assay using rVVp53 (solid line) or rVVpp65 (dashed line) infected 10.1 cells. (b) Splenocytes from rMVAmup53 (solid line) or rMVApp65 (dashed line) vaccinated mice were harvested at 14 days following vaccination and restimulated in vitro for 6 days with rAdp53 infected syngeneic LPS blasts. Cytotoxicity was measured against rVVp53 infected 10.1 cells. (c) Splenocytes harvested 14 days after rMVAmup53 (solid line) or rMVApp65 (dashed line) vaccination were restimulated in vitro for 6 days using syngeneic LPS blasts infected with rMVAp53. Cytotoxicity was measured against Meth A cells by a standard 4-h $^{51}$Cr release assay.
Figure 3B:
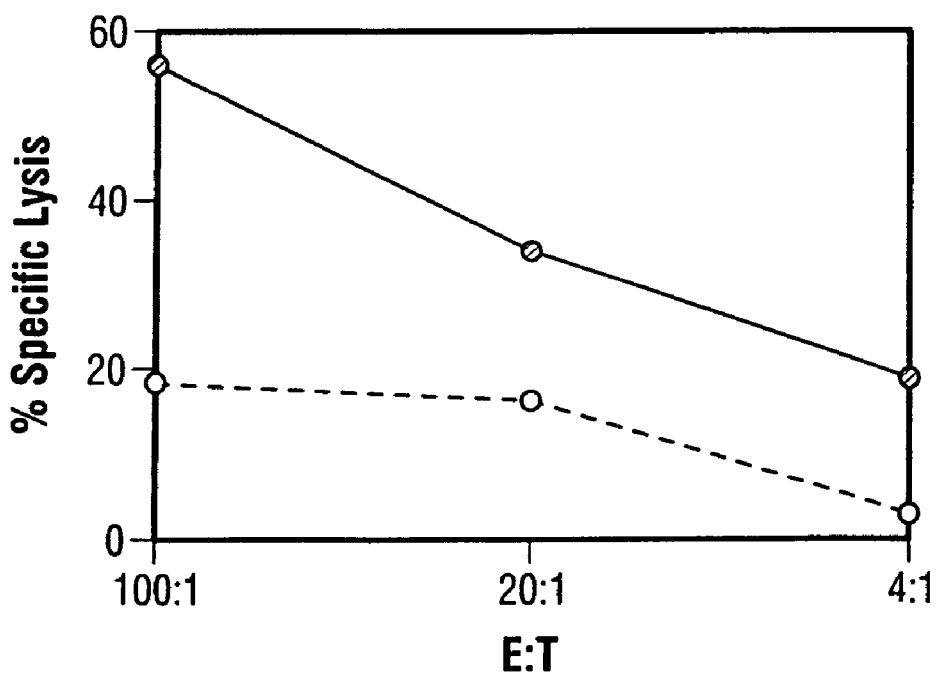
Figure 3C:
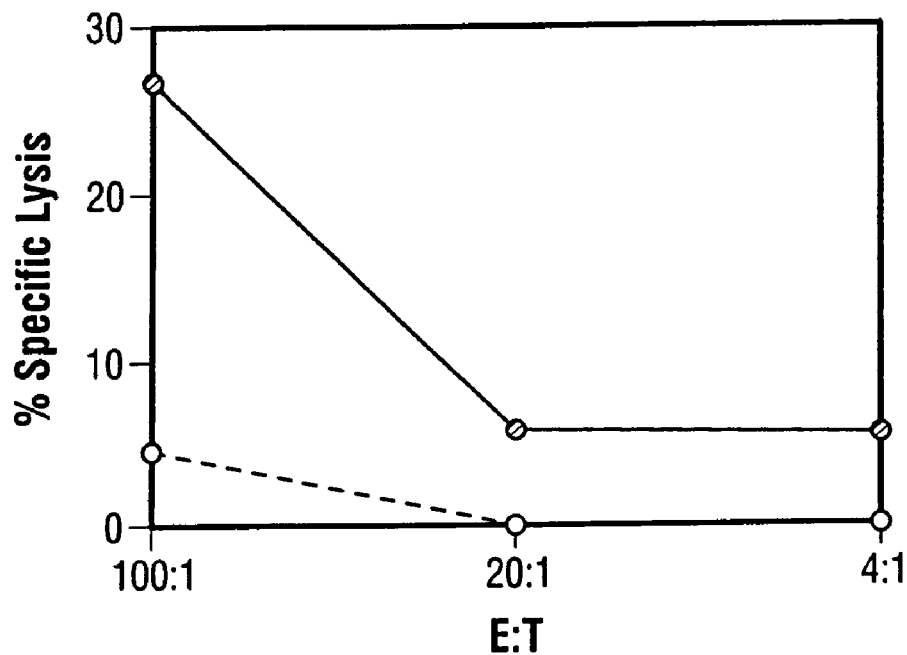

Vaccination of mice with rMVA expressing viral and tumor associated antigens results in enhanced antigen specific CTL responses. One goal of this example was to determine if vaccination with rMVAmup53 could break p53 tolerance, resulting in the generation of p53-specific CTL. Mice were vaccinated i.p. with $5\times10^7$ pfu of either rMVAmup53 or rMVApp65. After two weeks, spleens were harvested and disassociated, and splenocytes were washed and counted. Splenocytes were restimulated in vitro for 6 days with syngeneic LPS blasts infected with rAd-mup53 or rMVAmup53. Na—$^{51}$CrO$_4$-labeled target cells that overexpress wt p53 were added to 96 well plates with the effectors, in triplicate, at various effector to target ratios, in 200 µl of complete medium. The plates were incubated for 4 hours at 37° C., and the supernatant was harvested and analyzed. Percent specific lysis was calculated using the formula: percent specific release=(experimental release−spontaneous release)/(total release−spontaneous release)×100. Splenocytes vaccinated with rMVAmup53 recognized and lysed target cells that over-expressed wt p53 (FIG. 3). In contrast, splenocytes from mice vaccinated with rMVApp65, which stimulates a vigorous pp65 specific CTL response, did not recognize the p53 over-expressing targets (FIG. 3B), demonstrating the specificity of the lymphocyte response. rMVAmup53 vaccination can also stimulate CTL recognition of a cell line bearing mutated p53, Meth A. Restimulated splenocytes vaccinated with rMVA-mup53 recognized mutant p53 over-expressing Meth A cells, but splenocytes vaccinated with rMVAmup53 did not (FIG. 3c).

Example 3

In vivo rMVAmup53 Tumor Challenge Experiments

Since a single vaccination with rMVAmup53 resulted in enhanced CTL responses, there was sufficient justification to examine the effect of rMVAmup53 vaccination on the growth of tumor cells in vivo.

Statistical Methods

For experiments where the growth rate of some tumors necessitated early sacrifice, growth curves were compared by the time to a fixed size using a logrank test. Contrasts of single groups to all others were conducted after a single omnibus test. For cell depletion experiments, all mice were followed for a fixed amount of time, and final tumor size was compared by the Wilcoxon rank-sum test, after a significant Kruskal-Wallis test if there were more than two groups. For survival experiments, a logrank test was used.

rMVAmup53 vs. Meth A Cells

Figure 4:
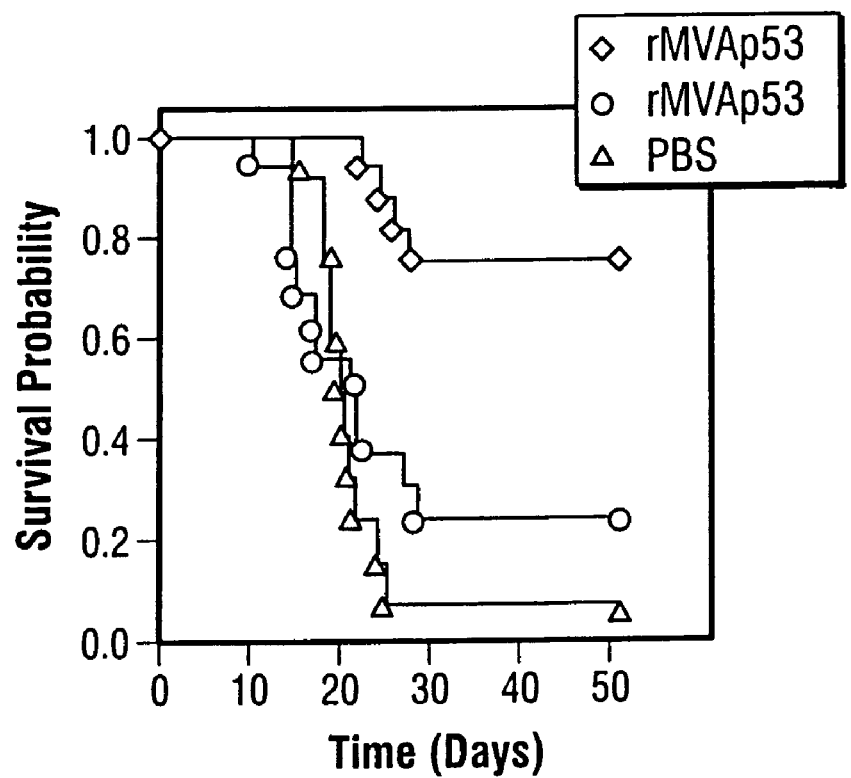
FIG. 4: Effect of vaccination with rMVAmup53 on Meth A tumor prevention. Balb/c mice were injected subcutaneously (s.c.) with $5\times10^5$ Meth A cells. On day 5, mice were vaccinated with either $5\times10^7$ pfu of rMVAmup53 (MVAp53) (n=16), $5\times10^7$ pfu rMVApp65 (MVApp65) (n=16), or PBS (n=12). The survival plot shows the proportion of surviving animals in each group as a function of days post tumor challenge. The improvement of the mice vaccinated with rMVAmup53 over both control groups is statistically significant (P<1) as determined by the log rank test.

Six-week-old female Balb/c mice were injected by subcutaneous (s.c.) route in the left flank with $5\times10^5$ Meth A cells. Mice injected s.c. with Meth A cells develop a rapidly growing fibrosarcoma that kills the majority of mice within 21 days (FIG. 3). On day 3, the mice were vaccinated with $5\times10^7$ pfu of rMVAmup53 by intraperitoneal (i.p.) injection. Negative control mice were injected with $5\times10^7$ rMVApp65 or PBS. The s.c. tumors were measured twice weekly in three dimensions with calipers. Tumors in rMVAmup53 treated animals grew at a much slower rate than those in control animals. At 14 days, the mean s.c. tumor volume for the rMVAmup53 treated group (n=16) was dramatically lower than both the rMVApp65 (n=16) and PBS (n=12) controls (22 mm$^3$ versus 348 mm$^3$, p<0.001 and 22 mm$^3$ versus 252 mm$^3$, p<0.001 by Student's t-test). Survival of rMVAmup53 treated animals was also significantly prolonged compared to either control group (FIG. 4). 12 of the 16 rMVAmup53 immunized mice failed to develop tumors entirely. The 12 tumor free rMVA-mup53 treated animals were re-challenged at day 52 with $5\times10^5$ Meth A tumor cells. All animals remained tumor free for the duration of a 30 day observation period (data not shown).

rMVAmup53 Plus Anti-CTLA-4 mAb vs. Meth A Cells

Figure 5:
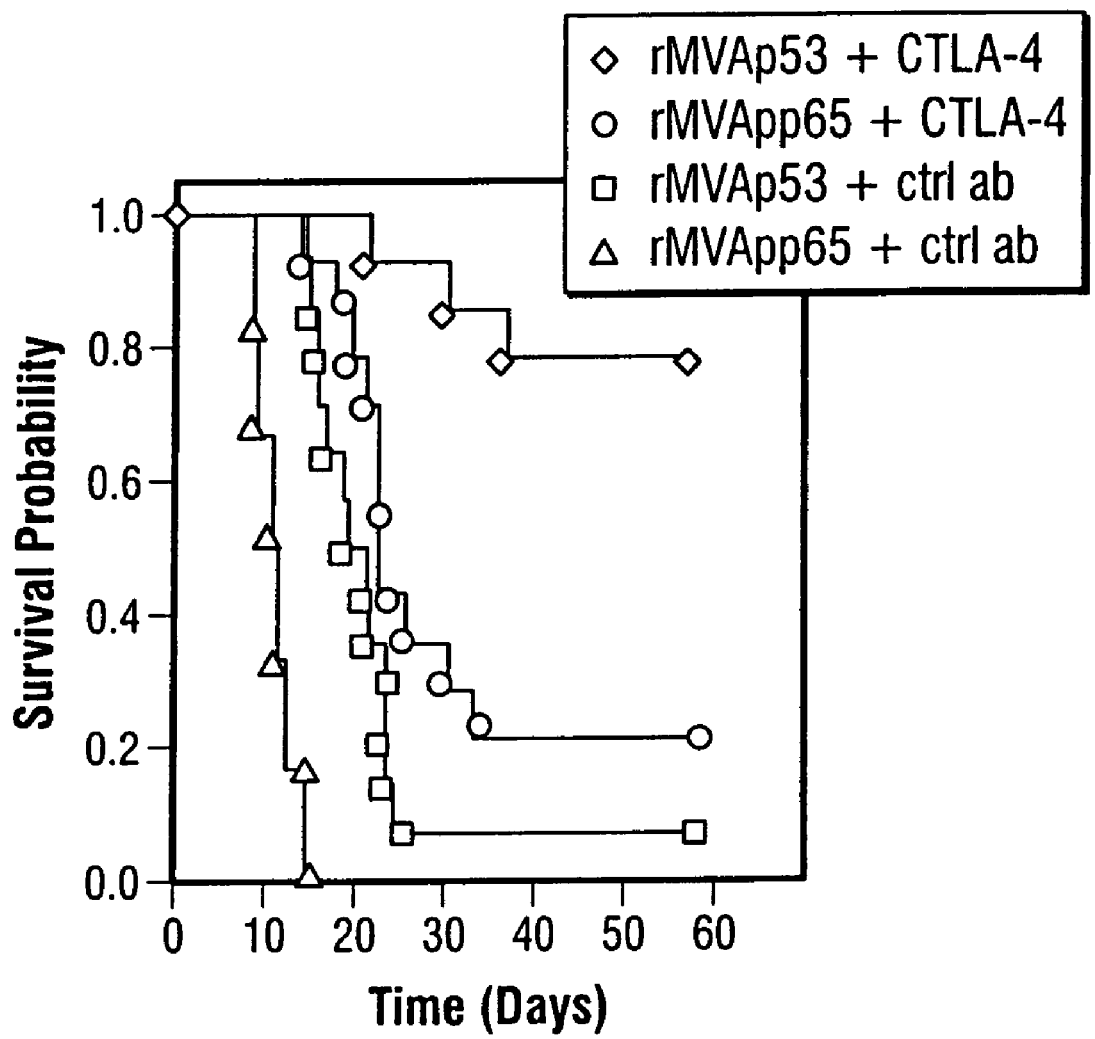
FIG. 5: Effect of vaccination with rMVAmup53 plus anti-CTLA-4 mAb on established Meth A tumors. Mice were injected s.c. with a rapidly lethal dose of $10^6$ Meth A cells. On days 6, 9, and 12 mice were injected i.p. with either anti-CTLA-4 mAb (CTLA4 mAb) or control mAb. On day 7, mice were vaccinated with either $5\times10^7$ pfu rMVAp53 (MVAp53) or $5\times10^7$ pfu rMVApp65 (MVAapp65). The survival plot shows the proportion of surviving animals in each group. The survival advantage of mice vaccinated with rMVAp53 plus anti-CTLA-4 mAb (n=14) over control animals receiving rMVApp65 plus CTLA-4 (n=14), rMVAp53 plus control ab (n=14), or rMVApp65 plus control ab (n=6) is statistically significant (P<0.001) as determined by the log rank test.

One potent strategy for optimizing tumor vaccines involves manipulating negative regulation of T cell responsiveness using an antibody that blocks CTLA-4 engagement with ligand. This phenomenon has been referred to as CTLA-4 blockade. Application of anti-CTLA-4 mAb in combination with cancer vaccines expressing tumor associated autoantigens, in some cases, results in tumor rejection along with breaking of tolerance and induction of autoimmunity. Therefore, mAb specific to CTLA-4 was added to rMVAmup53 vaccination to determine whether it would synergize and augment the anti-tumor activity against Meth A in vivo. A more rigorous tumor model was designed in order to overcome the potent antitumor effect of CTLA-4 blockade alone. Six-week-old Balb/c mice were injected s.c. in the left flank with $10^6$ Meth A cells rather than $5 \times 10^5$ Meth A cells, and treatment was postponed until a palpable tumor nodule was identified (Day 6). This more rigorous model overcame the effect of the CTLA-4 blockade, producing a rapidly lethal tumor in the majority of mice despite anti-CTLA-4 mAb treatment (FIG. 5). On day 7, mice were injected i.p. with $5 \times 10^7$ pfu of rMVAmup53. Controls were the same as above. Anti-CTLA-4 mAb antibody or control hamster Ab were injected i.p. on days 6, 9, and 12 at 100, 50 and 50 µg dose, respectively. 11 of the 14 mice immunized with rMVAmup53 plus anti-CTLA-4 mAb rejected tumors, resulting in tumor free survival for the duration of the 60 day observation period (FIG. 5). By contrast, mice treated with rMVApp65 and control antibody died rapidly of progressive tumor (FIG. 5) as did PBS treated controls (data not shown). The 11 tumor-free rMVAmup53 plus anti-CTLA-4 mAb treated mice also rejected a re-challenge with $10^6$ Meth A tumor cells at 60 days, and remained tumor free for the duration of a 30 day observation period (data not shown).

rMVAmup53 Plus Anti-CTLA-4 mAb vs. 11A-1 Cells

Figure 6:
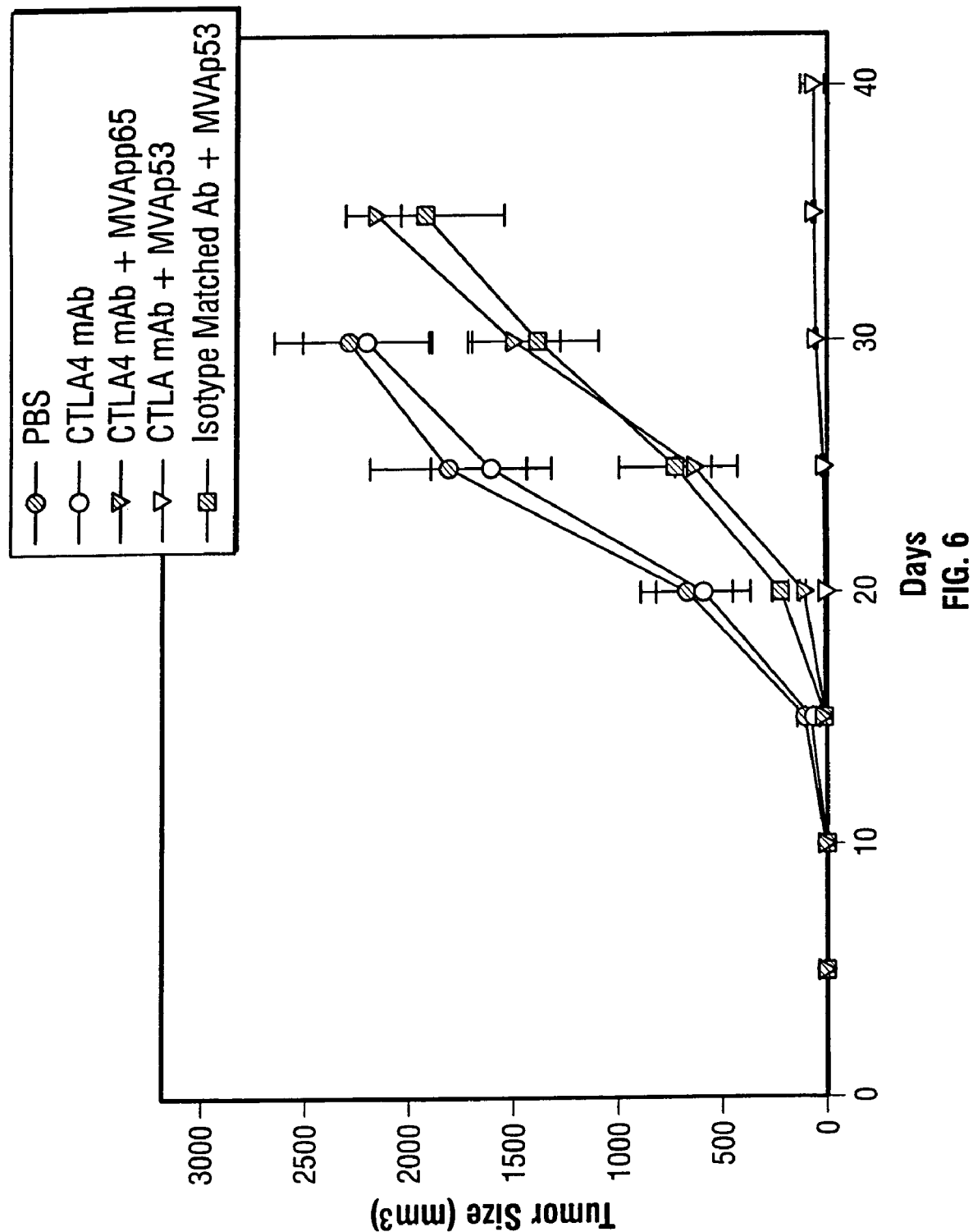
FIG. 6: Effect of vaccination with rMVAmup53 plus anti-CTLA-4 mAb on established 11A-1 tumors. Balb/c mice were injected s.c. with $2\times10^6$ 11A-1 cells (p=0.00044, comparing rMVAmup53 plus anti-CTLA-4 mAb to all other groups). Anti-CTLA-4 mAb 9H10 (CTLA4 mAb) or the control hamster isotype matched polyclonal antibody (isotype matched Ab) were injected i.p. on days 4, 7, and 10 at 100, 50, and 50 µg dose, respectively. On day 5, mice were vaccinated i.p. with either $5\times10^7$ pfu of rMVAmup53 (MVAp53), $5\times10^7$ pfu rMVApp65 (MVApp65), or PBS. Each line represents the mean and standard deviation of eight mice.

Six-week-old Balb/c mice were injected s.c. in the left flank with $2 \times 10^6$ 11A-1 cells. 11A-1 is a rapidly growing malignant cell line that is poorly immunogenic. Mice vaccinated with $10^6$ irradiated 11A-1 tumor cells failed to reject a subsequent challenge with 11A-1 (data not shown). Anti-CTLA-4 mAb or the control hamster antibody was injected i.p. on days 4, 7, and 10 at 100, 50, and 50 µg/dose, respectively. On day 5, mice were vaccinated i.p. with either $5 \times 10^7$ pfu of rMVAmup53, $5 \times 10^7$ MVApp65, or PBS. s.c. tumors were measured twice weekly in three dimensions with calipers. Mice vaccinated with rMVAmup53 plus anti-CTLA-4 mAb rejected their tumors (FIG. 6). Animals treated with anti-CTLA-4 mAb alone or with a control MVA vaccine developed rapidly progressing lethal tumors (p=0.00044, comparing rMVAmup53 with anti-CTLA-4 mAb blockade to control groups).

rMVAmup53 Plus Anti-CTLA-4 mAb vs. MC-38 Cells

Figure 7:
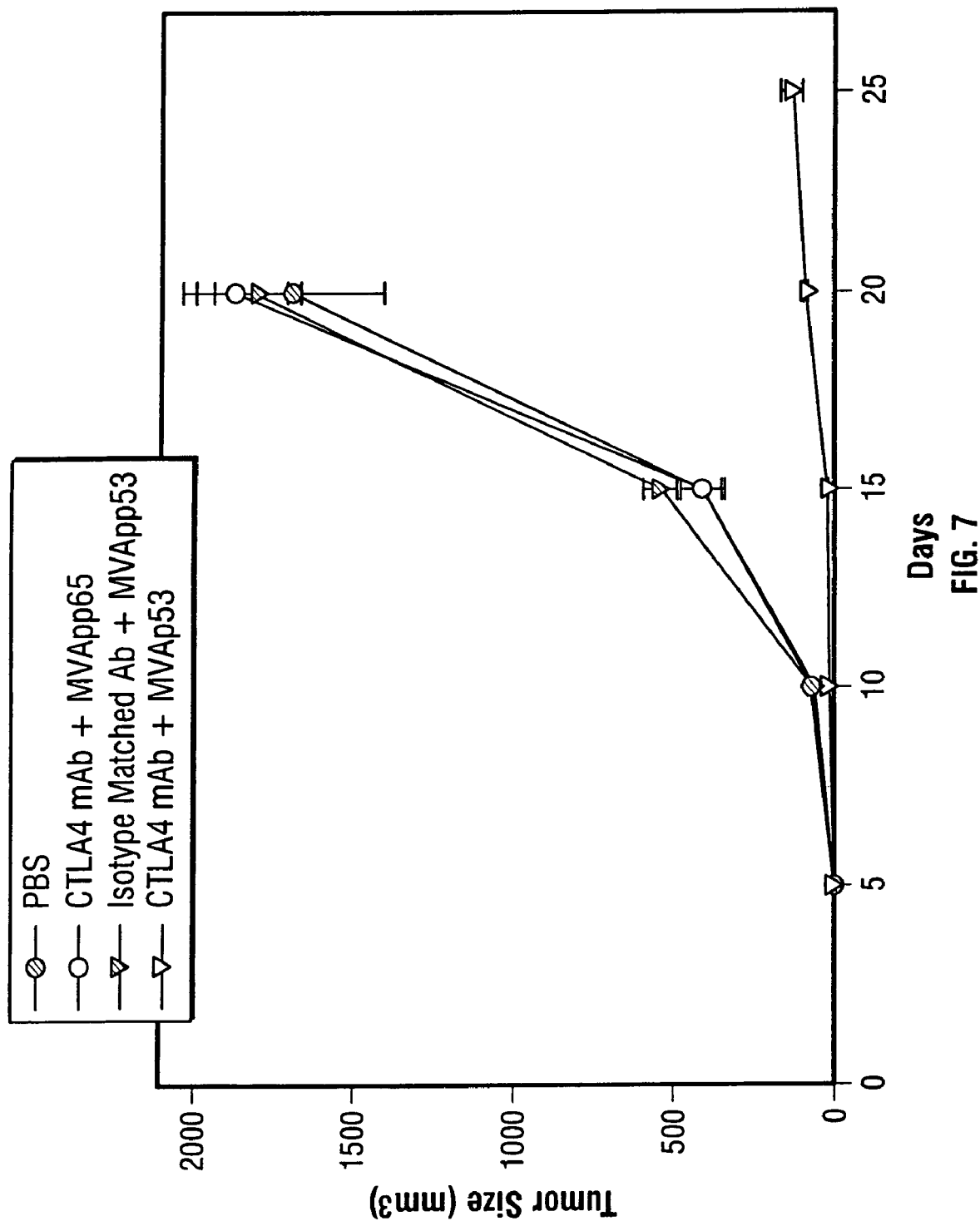
FIG. 7: Effect of vaccination with rMVAmup53 plus anti-CTLA-4 mAb on established MC-38 tumors. C57BL/6 mice were injected s.c. with $1\times10^6$ MC-38 cells (p=0.0001, comparing rMVAmup53 plus anti-CTLA-4 mAb to all other groups). Anti-CTLA-4 mAb 9H10 (CTLA4 mAb) or the control hamster isotype matched polyclonal antibody (isotype matched Ab) were injected i.p. on days 4, 7, and 10 at 100, 50, and 50 µg dose, respectively. On day 5, mice were vaccinated i.p. with either $5\times10^7$ pfu of rMVAmup53 (MVAp53), $5\times10^7$ pfu rMVApp65 (MVApp65), or PBS. Each line represents the mean and standard deviation of eight mice.

Six-week-old C57BL/6 mice, TLR9$^{-/-}$, or IL-6$^{-/-}$ mice were injected s.c. in the left flank with $1 \times 10^6$ MC-38 cells. Anti-CTLA-4 mAb or the control hamster antibody was injected i.p. on days 4, 7, and 10 at 100, 50, and 50 µg/dose, respectively. On day 5, mice were vaccinated i.p. with either $5 \times 10^7$ pfu of rMVAmup53, $5 \times 10^7$ rMVApp65, or PBS. s.c. tumors were measured twice weekly in three dimensions with calipers. Mice vaccinated with rMVAmup53 plus anti-CTLA-4 mAb rejected their tumors, while those treated with anti-CTLA-4 mAb alone or with a control MVA vaccine developed rapidly progressing tumors (p=0.0001, comparing rMVAmup53 with anti-CTLA-4 mAb to control groups) (FIG. 7).

rMVAmup53 Plus CpG ODN vs. 11A-1 Cells

Figure 8:
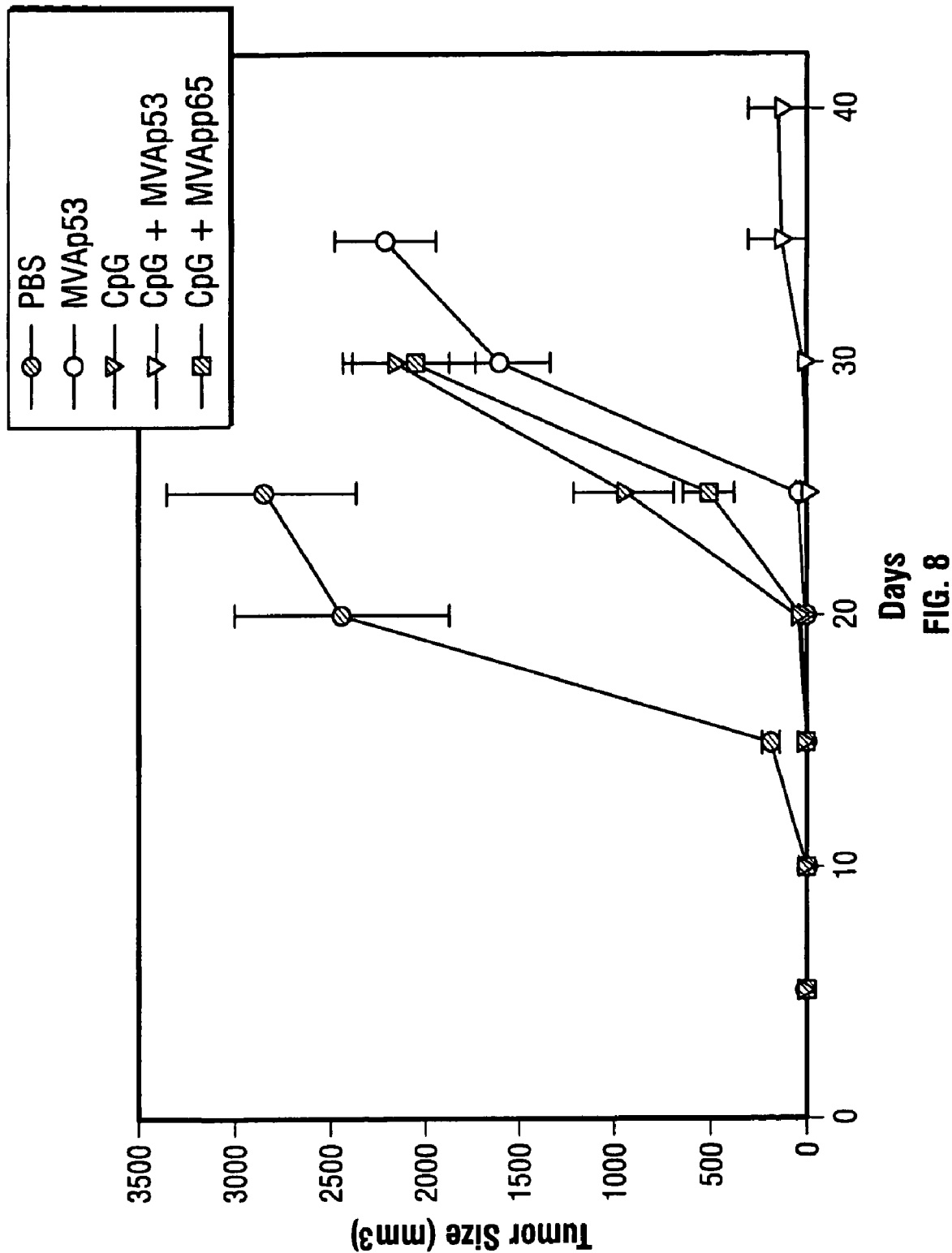
FIG. 8: Effect of vaccination with rMVAmup53 plus CpG ODN on established 11A-1 tumors. Balb/c mice were injected s.c. with $2\times10^6$ 11A-1 cells (p=0.00002, comparing rMVAmup53 plus CpG ODN to all other groups). 15 nmoles of CpG ODN (CpG) was injected i.p. on days 4, 9, and 14. On day 5, the mice were immunized i.p. with either $5\times10^7$ pfu of rMVAmup53 (MVAp53), $5\times10^7$ pfu of rMVApp65 (MVApp65), or PBS.

CpG ODN treatment has been shown to be an effective immunomodulator in a number of experimental tumor vaccine models (Krieg 2002). Mice were challenged with 11A-1 tumor as above. 15 nmoles of CpG ODN or the non-CpG ODN control were injected i.p. on days 4, 9, and 14. On day 5, the mice were vaccinated i.p. with either $5 \times 10^7$ pfu of rMVAmup53, $5 \times 10^7$ rMVApp65, or PBS. The s.c. tumors were measured twice weekly in three dimensions with calipers. While rMVAmup53 and CpG ODN each separately resulted in minimal attenuation of tumor growth, all animals developed progressively lethal tumors. The combination of CpG ODN and rMVAmup53 vaccination resulted in significantly diminished tumor outgrowth (p=0.00002) (FIG. 8). 6 of the 8 animals treated with rMVAmup53 plus CpG ODN did not develop palpable tumors and developed lasting tumor immunity, rejecting a rechallenge with 11A-1 at 60 days (data not shown).

rMVAmup53 Plus CpG ODN vs. Meth A Cells

Figure 9:
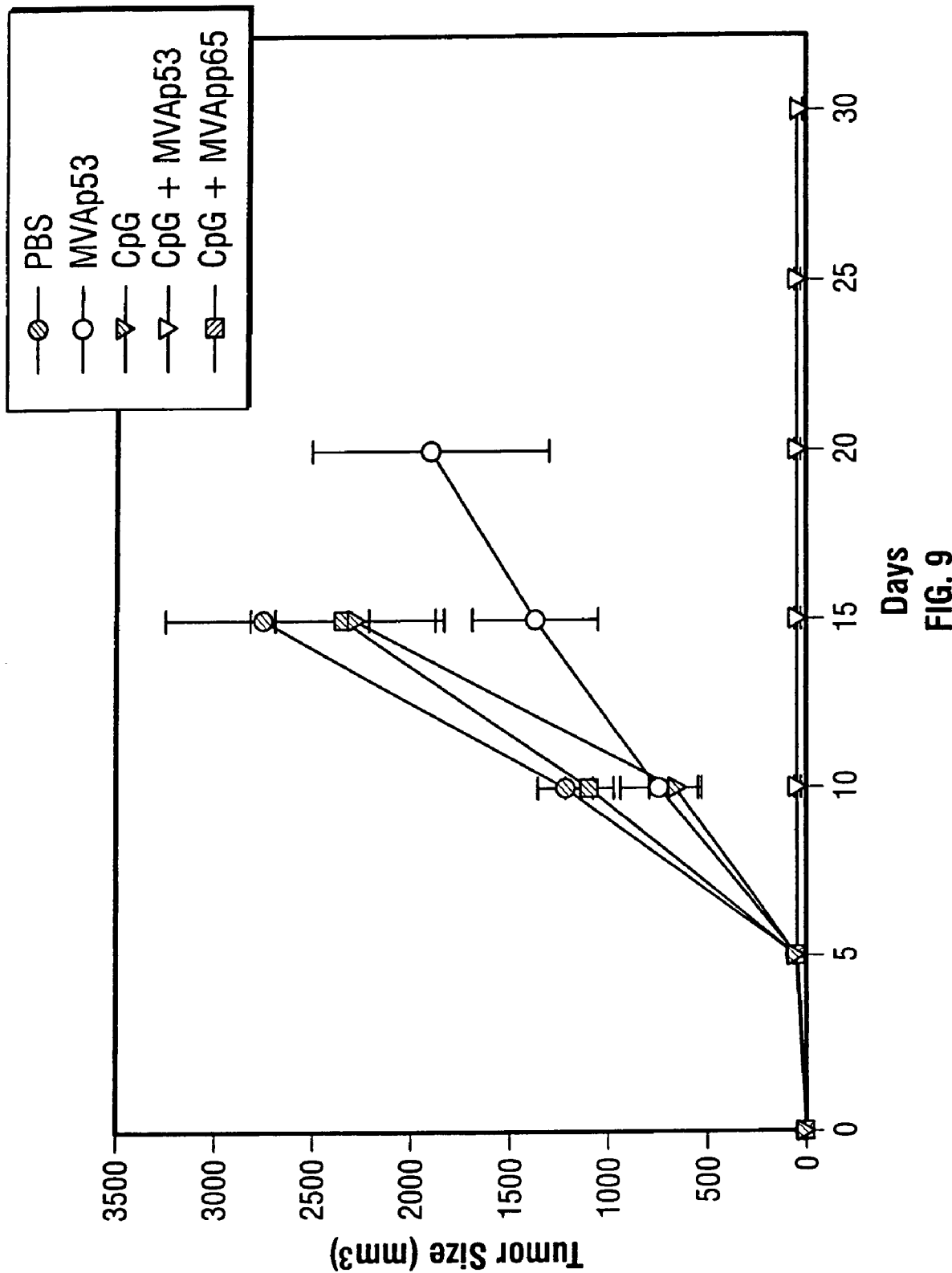
FIG. 9: Effect of vaccination with rMVAmup53 plus CpG ODN on established Meth A tumors. Balb/c mice were injected s.c. with $1\times10^6$ Meth A cells (p=0.0015, comparing rMVAmup53 plus CpG ODN to all other groups). 15 nmoles of CpG ODN (CpG) was injected i.p. on days 4, 9, and 14. On day 5, the mice were immunized i.p. with either $5\times10^7$ pfu of rMVAmup53 (MVAp53), $5\times10^7$ pfu of rMVApp65 (MVApp65), or PBS.

A pattern of tumor rejection similar to that for 11A-1 was seen following treatment of early established Meth A tumors in Balb/c mice (p=0.0015) (FIG. 9).

rMVAmup53 Plus CpG ODN vs. MC-38 Cells

Figure 10:
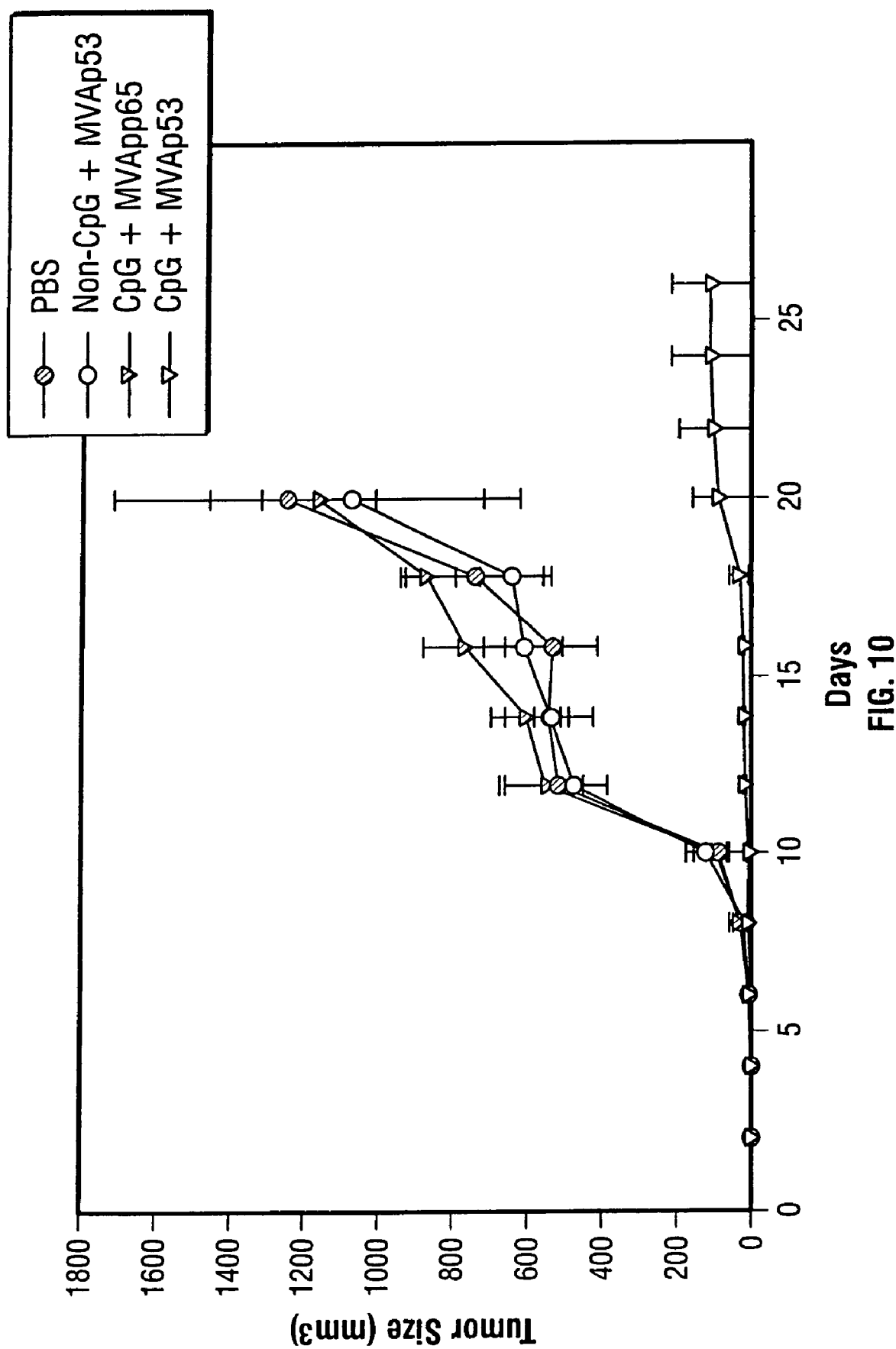
FIG. 10: Effect of vaccination with rMVAmup53 plus CpG ODN on established MC-38 tumors. C57BL/6 mice were injected with $1\times10^6$ MC-38 cells (p=0.0004, comparing rMVAmup53 plus CpG ODN to all other groups). 15 nmoles of CpG ODN (CpG) was injected i.p. on days 4, 9, and 14. On day 5, the mice were immunized i.p. with either $5\times10^7$ pfu of rMVAmup53 (MVAp53), $5\times10^7$ pfu of rMVApp65 (MVApp65), or PBS.

To demonstrate that the immunomodulator effect of CpG ODN on rMVAmup53 vaccination is not strain specific, the vaccination strategy was repeated in C57BL/6 mice bearing early established MC-38 colon cancers. Vaccination with rMVAmup53 plus CpG ODN resulted in significant suppression of tumor growth (p=0.0004) (FIG. 10).

rMVAmup53 Plus Anti-CTLA-4 mAb Plus CpG ODN vs. 11A-1 Cells

Figure 11:
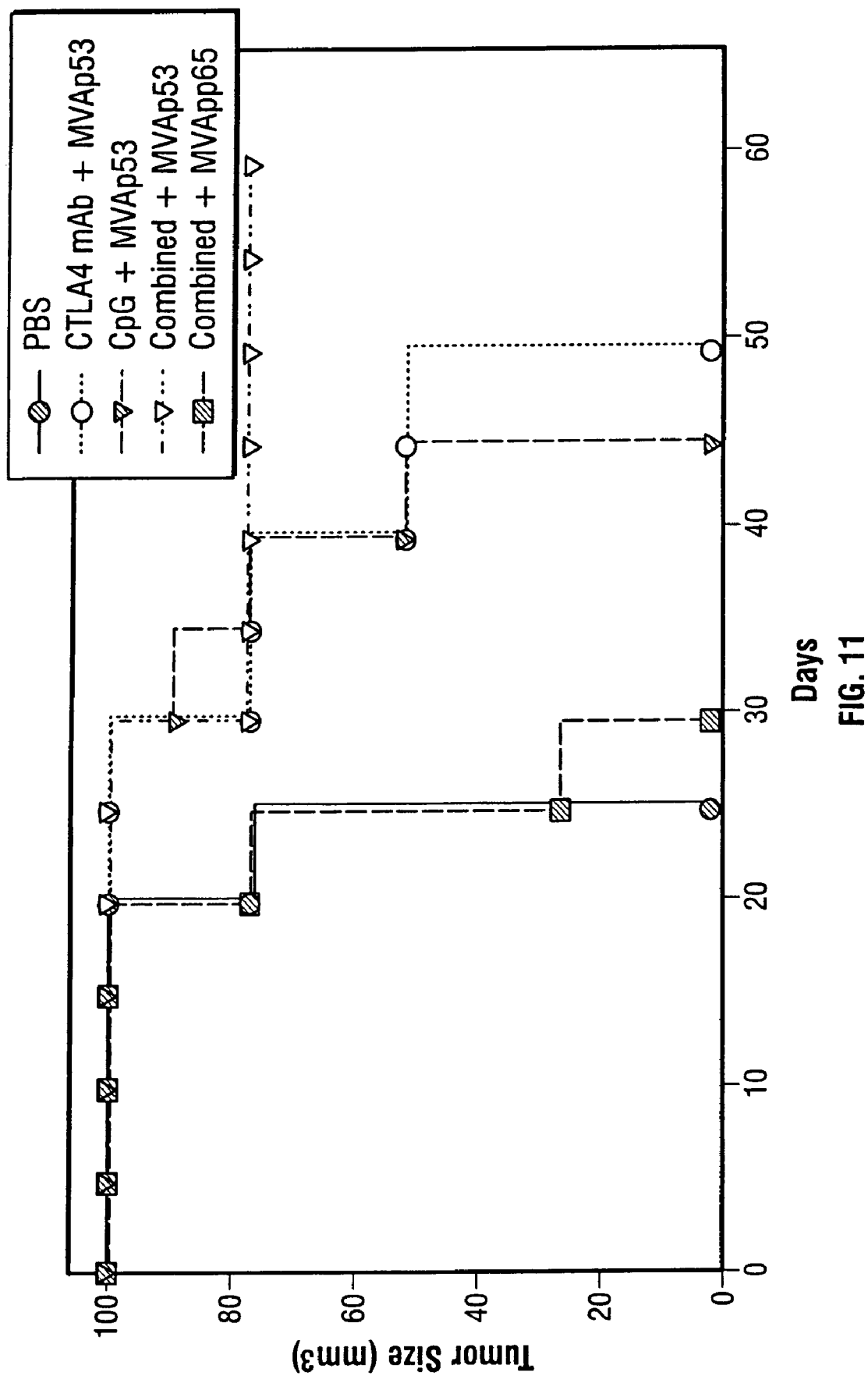
FIG. 11: Effect of vaccination with rMVAmup53 plus anti-CTLA-4 mAb and CpG ODN on established 11A-1 tumors. Balb/c mice (n=8) were injected s.c. with $2\times10^6$ 11A-1 cells. Anti-CTLA-4 mAb (CTLA4 mAb) was injected i.p. on days 14, 17, and 20 at 100, 50, and 50 µg dose, respectively. 15 nmoles of CpG ODN (CpG) was injected i.p. on days 14, 19, and 24. On day 15, mice were vaccinated i.p. with either $5\times10^7$ pfu of rMVAmup53 (MVAp53), $5\times10^7$ pfu rMVApp65, or PBS. The survival plot shows the proportion of surviving animals in each group as a function of days post tumor challenge. p=0.02 comparing combined CpG ODN and anti-CTLA-4 mAb to CpG ODN alone, and p=0.01 comparing combined CpG ODN and anti-CTLA-4 mAb to anti-CTLA-4 mAb alone.

A more rigorous tumor model was designed to evaluate the potential additive effects of CpG ODN and anti-CTLA-4 mAb on rMVAmup53 vaccination. Six-week-old Balb/c mice were injected s.c. in the left flank with $2 \times 10^6$ 11A-1 cells and followed for two weeks until palpable tumors were present. Anti-CTLA-4 mAb or the control hamster antibody was injected i.p. on days 14, 17, and 20, at 100, 50, and 50 µg/dose, respectively. 15 nmoles of CpG ODN was injected i.p. on days 14, 19, and 24. On day 15, the mice were vaccinated i.p. with either $5 \times 10^7$ pfu of rMVAmup53, $5 \times 10^7$ MVApp65, or PBS.

rMVAmup53 vaccination combined with either anti-CTLA-4 mAb or CpG ODN immunomodulators resulted in prolonged survival, but all animals eventually succumbed to progressive tumor growth. The combination of anti-CTLA-4 mAb and CpG ODN administration with rMVAmup53 vaccination resulted in tumor rejection and prolonged survival in the majority of treated animals (FIG. 11). The combination of anti-CTLA-4 mAb and CpG ODN provides better immunomodulator activity than either CpG ODN alone (p=0.02) or anti-CTLA-4 mAb alone (p=0.01). The effect of combined anti-CTLA-4 mAb and CpG ODN administration provides a greater benefit in terms of survival at 60 days than the simple addition of the effects of both immunomodulators separately.

rMVAmup53 Plus Anti-CTLA-4 mAb Plus CpG ODN vs. MC-38 Cells

Figure 12:
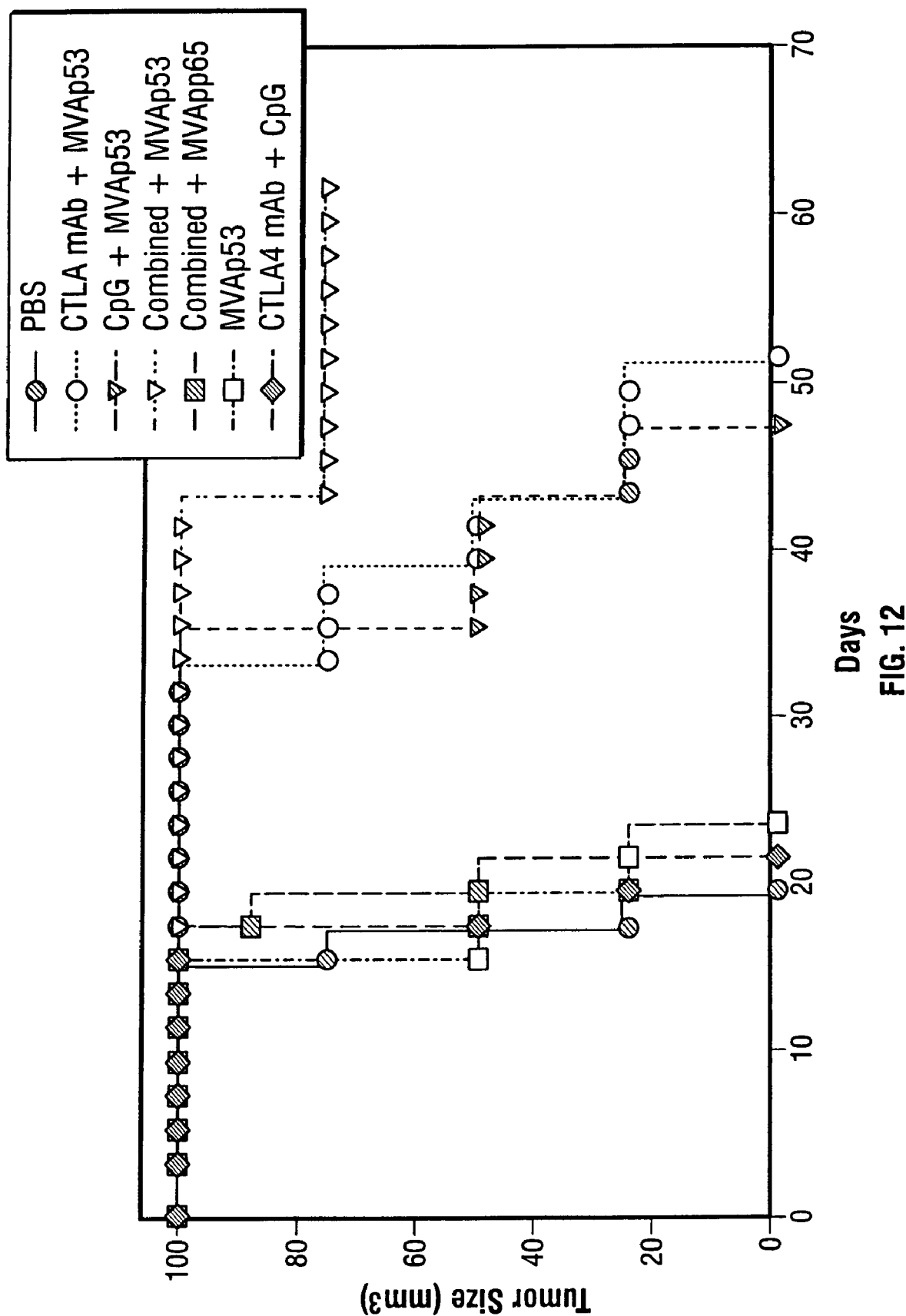
FIG. 12: Effect of vaccination with rMVAmup53 plus anti-CTLA-4 mAb and CpG ODN on established MC-38 tumors. C57BL/6 mice (n=8) were injected s.c. with $1\times10^6$ MC-38 cells. Anti-CTLA-4 mAb was injected i.p. on days 4, 7, and 10 at 100, 50, and 50/g dose, respectively. 15 nmoles of CpG ODN was injected i.p. on days 4, 9, and 14. On day 5, mice were vaccinated i.p. with either $5\times10^7$ pfu rMVAmup53, $5\times10^7$ pfu MVApp65, or PBS. The survival plot shows the proportion of surviving animals in each group as a function of days post tumor challenge. p=0.002 comparing combined CpG ODN and anti-CTLA-4 mAb to CpG alone, and p=0.001 comparing combined CpG ODN and anti-CTLA-4 mAb with anti-CTLA-4 mAb alone.

A similar pattern was seen in C57BL/6 mice bearing MC 38 tumors (FIG. 12). C57BL/6 mice bearing MC-38 tumors were treated with rMVAmup53 plus a combination of anti-CTLA-4 mAb and CpG ODN as described above for 11A-1. In this tumor model, the combination of anti-CTLA-4 mAb and CpG ODN also provided better immunomodulator activity than either CpG ODN alone (p=0.002) or anti-CTLA-4 mAb alone (p=0.001). The combined effect in both tumor models is not simply a dose additive effect, as the CpG ODN and anti-CTLA-4 mAb were both already administered at doses of maximal efficacy. The striking increases in activity found when both immunomodulators are used together in at least two different tumors suggests that further investigation of the combined modality is warranted in humans.

Example 4

Cellular Requirements for Anti-CTLA-4 mAb and CpG ODN Immunomodulator Effect

To determine the cellular requirements for the immunomodulator effect of anti-CTLA-4 mAb and CpG ODN, Balb/c mice were depleted of $CD4^+$, $CD8^+$, or NK cells prior to vaccination. Depletion was accomplished by i.p. injection of 200 µg of $CD4^+$, $CD8^+$, or NK1.1 cell specific mAbs, or a control mAb. Injections were given on days −1, 1, 3, 4, 6, 8, and 15, with a maintenance dose every 7 days until the termination of the animals. This regimen was shown to deplete (>95%) Balb/c mice of $CD4^+$, $CD8^+$, or NK 1.1 cells based on flow cytometry of peripheral blood from treated animals (data not shown).

Figure 13A:
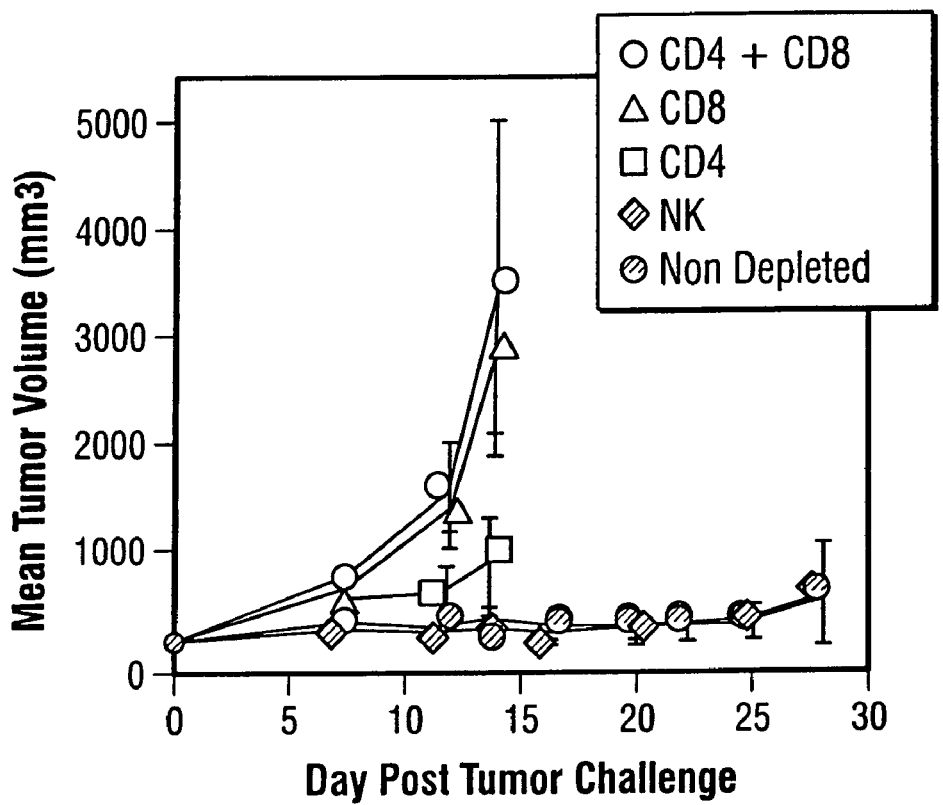
FIG. 13: Cellular requirements for anti-CTLA-4 mAb immunomodulator effect on Meth A tumors. Balb/c mice (a) or IFN-$\gamma^{KO}$ Balb/c mice (b) were injected s.c. with a rapidly lethal dose of $10^6$ Meth A cells. Groups of mice from both populations were injected i.p. with depleting doses of anti-CD4, anti-CD8, anti-NK1.1, or control mAb on days −1, 1, 3, and 10, and weekly thereafter. On days 6, 9, and 12 mice were injected i.p. with either anti-CTLA-4 mAb (CTLA4 mAb) or control mAb. On day 7, mice were vaccinated with either $5\times10^7$ pfu rMVAp53 (MVAp53) or $5\times10^7$ pfu rMVApp65 (MVAapp65). (a) Mean tumor growth was calculated for each group of Balb/c mice, with error bars illustrating standard deviation. The last datapoint for each line represents the first mortality. (b) The proportion of surviving IFN-$\gamma^{KO}$ Balb/c mice is plotted.
Figure 15:
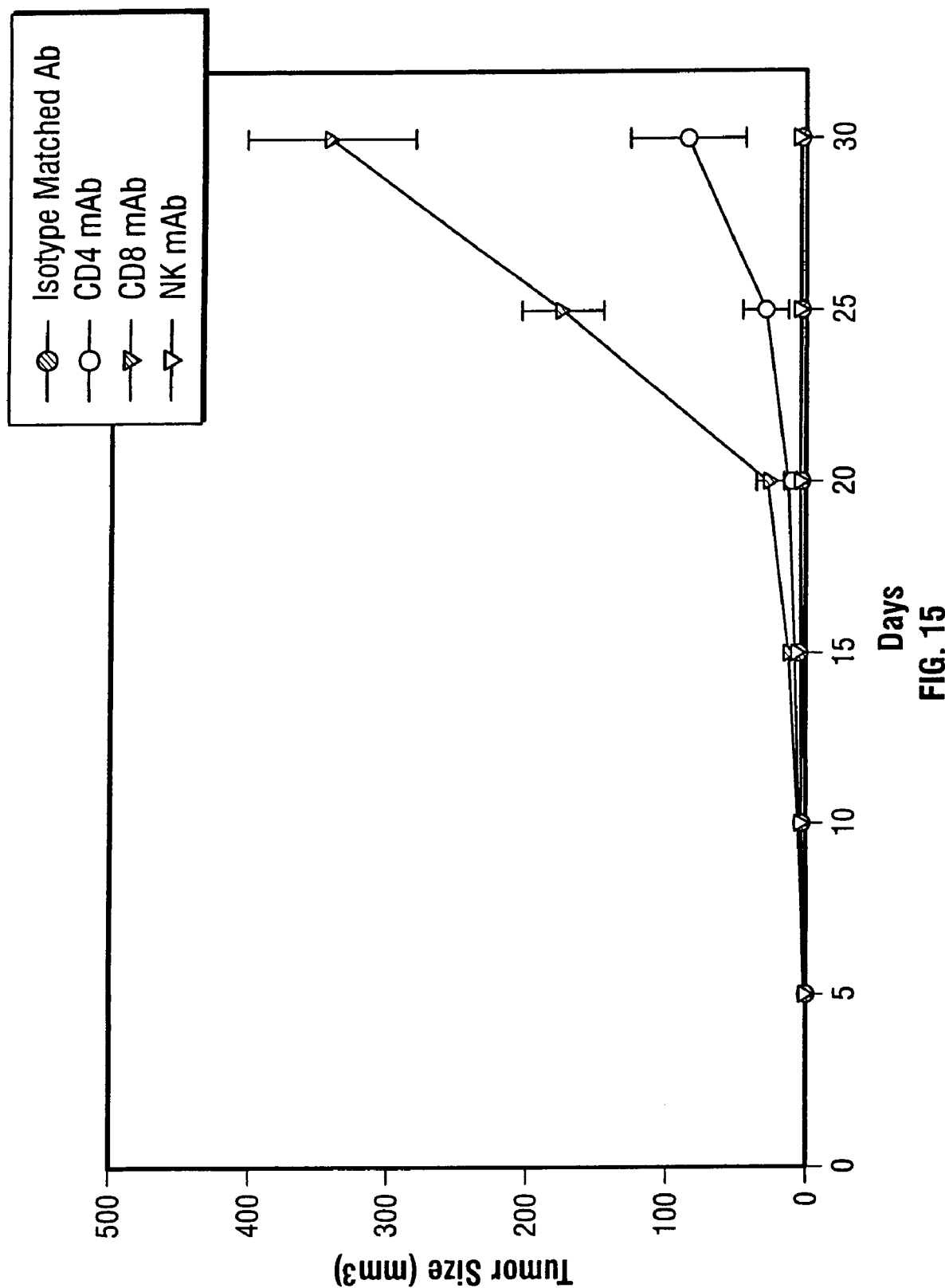
FIG. 15: Cellular requirements for anti-CTLA-4 mAb immunomodulator effects on 11A-1 tumors. Mice were injected s.c. with $2\times10^6$ 11A-1 cells. Anti-CTLA-4 mAb was injected i.p. on days 4, 7, and 10 at 100, 50, and 50 μg/dose, respectively. On day 5, the mice were vaccinated i.p. with $5\times10^7$ pfu rMVAmup53. The mice were depleted of CD8$^+$, CD4$^+$, or NK cells by i.p. injection with the relevant mAb or control mAb on days 4, 6, 8, and 15, and then every 7 days thereafter. Tumors were measured twice weekly in three dimensions with calipers. Each curve represents the mean and standard deviation of 8 mice. p=0.004, comparing CD8$^+$ depleted to all other groups. p=0.008, comparing CD4$^+$ depleted to NK depleted and control groups.

The cellular requirements for the immunomodulator effect of CTLA-4 blockade on rMVAmup53 vaccination were evaluated using the Meth A tumor model in Balb/c mice. Mice depleted of $CD8^+$ T cells or $CD4^+$ and $CD8^+$ T cells simultaneously develop rapidly lethal tumors. These tumors are resistant to vaccination with rMVAmup53 and anti-CTLA-4 mAb. In contrast, $CD4^+$ T cell depletion resulted in only a partial abrogation of response to the vaccine. NK1.1 cell depletion had little effect on the ability of vaccinated mice to reject Meth A (FIG. 13a). Results were the same when the depleting mAbs were administered after vaccine and anti-CTLA-4 mAb treatment (data now shown). Similar results were also obtained when the 11A-1 tumor model was used rather than the Meth A tumor model. The therapeutic effect of rMVAmup53 and anti-CTLA-4 mAb could be eliminated by administering depleting doses of anti-$CD8^+$ mAb (p=0.004) (FIG. 15). The antitumor effect was partially blocked by the administration of depleting anti-$CD4^+$ mAb (p=0.008), and unaffected by the administration of an NK depleting mAb. These results show that the immunomodulator effect of anti-CTLA-4 mAb is entirely dependent on $CD8^+$ cells, partially dependent on $CD4^+$ cells, and not dependent at all on NK cells (Espenschied 2003).

Figure 14:
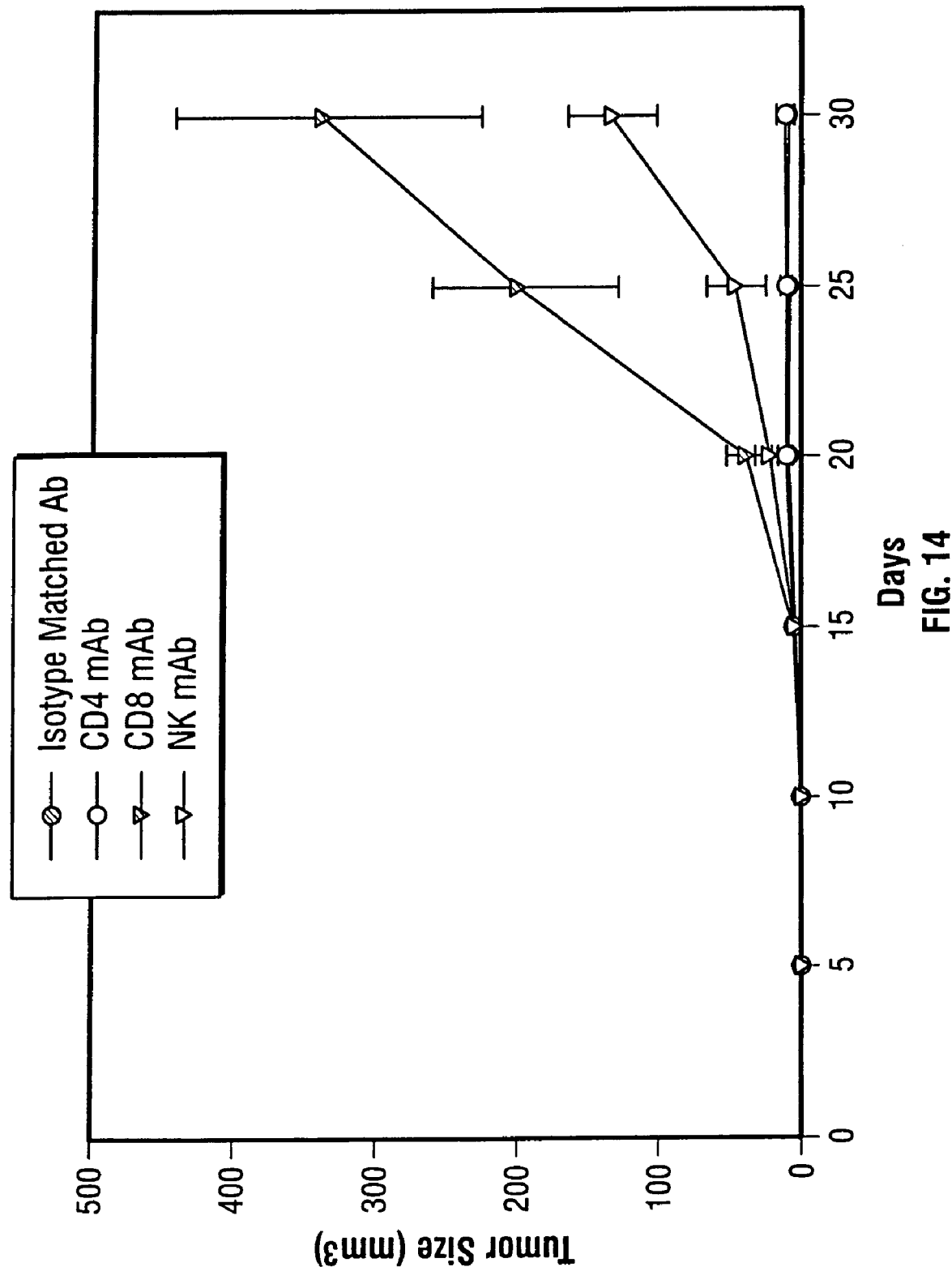
FIG. 14: Cellular requirements for CpG ODN immunomodulator effects on 11A-1 tumors. Balb/c mice were injected s.c. with $2\times10^6$ 11A-1 cells. 15 nmoles of CpG ODN was injected i.p. on days 4, 9, and 14. On day 5, mice were vaccinated i.p. with $5\times10^7$ pfu of rMVAmup53. Mice were injected i.p. with depleting doses of anti-CD4 (CD4), anti-CD8 (CD8), anti-NK1.1 (NK), or control mAb on days 4, 6, 8, and 15, and every 7 days thereafter. Tumors were measured twice weekly in three dimensions. p=0.004 by two-sided Wilcoxon test, comparing CD8$^+$ depleted to all other groups. p=0.007, comparing anti-NK1.1 to anti-CD4 and control mAb.

The cellular requirements for the immunomodulator effect of CpG ODN on rMVAmup53 vaccination were evaluated using Balb/c mice with four-day established 11A-1 tumors. As with anti-CTLA-4 mAb, the immunomodulator effect of CpG ODN on MVAmup53 vaccination could be completely abrogated by the administration of depleting $CD8^{+\ mAb}$ $(p=0.004)$ (FIG. 14). However, unlike anti-CTLA-4 mAb, the immunomodulator effect of CpG ODN was unaffected by $CD4^+$ depletion, while depletion of NK cells partially abrogated the vaccine effect (p=0.007, comparing NK to $CD4^+$ and control antibody depletions). The difference in cellular requirements for $CD4^+$ and NK between anti-CTLA-4 mAb and CpG ODN is striking, because both immunomodulators cause equivalent levels of rejection. These results suggest that the two immunomodulators act through differing immunologic mechanisms. This information, combined with the data regarding the effects of combined anti-CTLA-4 mAb/CpG ODN administration on rMVAmup53, suggest a synergistic effect by the two immunomodulators on tumor growth.

Contribution of IFN-γ

Figure 13B:
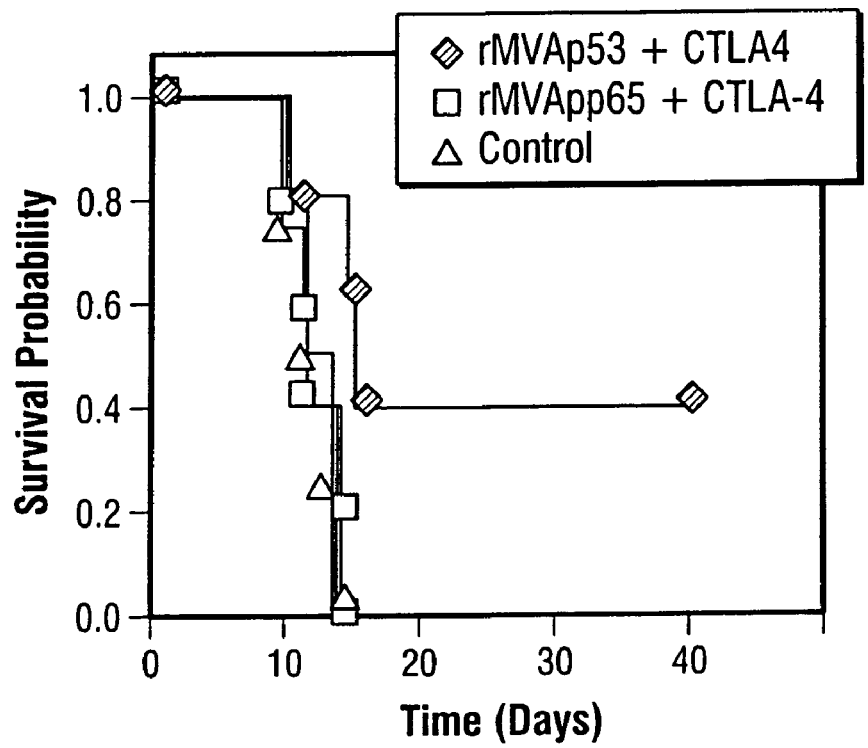

The contribution of IFN-γ secretion to the effect of CTLA-4 blockade and rMVAmup53 vaccination was evaluated in IFN-$γ^{KO}$ mice. Both unvaccinated mice and mice vaccinated with rMVApp65 and anti-CTLA4 mAb developed lethal tumors at a rate similar to that seen in normal Balb/c mice (FIG. 13b). 3 of the 5 IFN-$γ^{KO}$ mice that were vaccinated with rMVAmup53 and anti-CTLA-4 mAb developed lethal tumor growth, confirming a contribution of IFN-γ to the vaccine/CTLA-4 blockade effect.

Contribution of TLR 9

Figure 16:
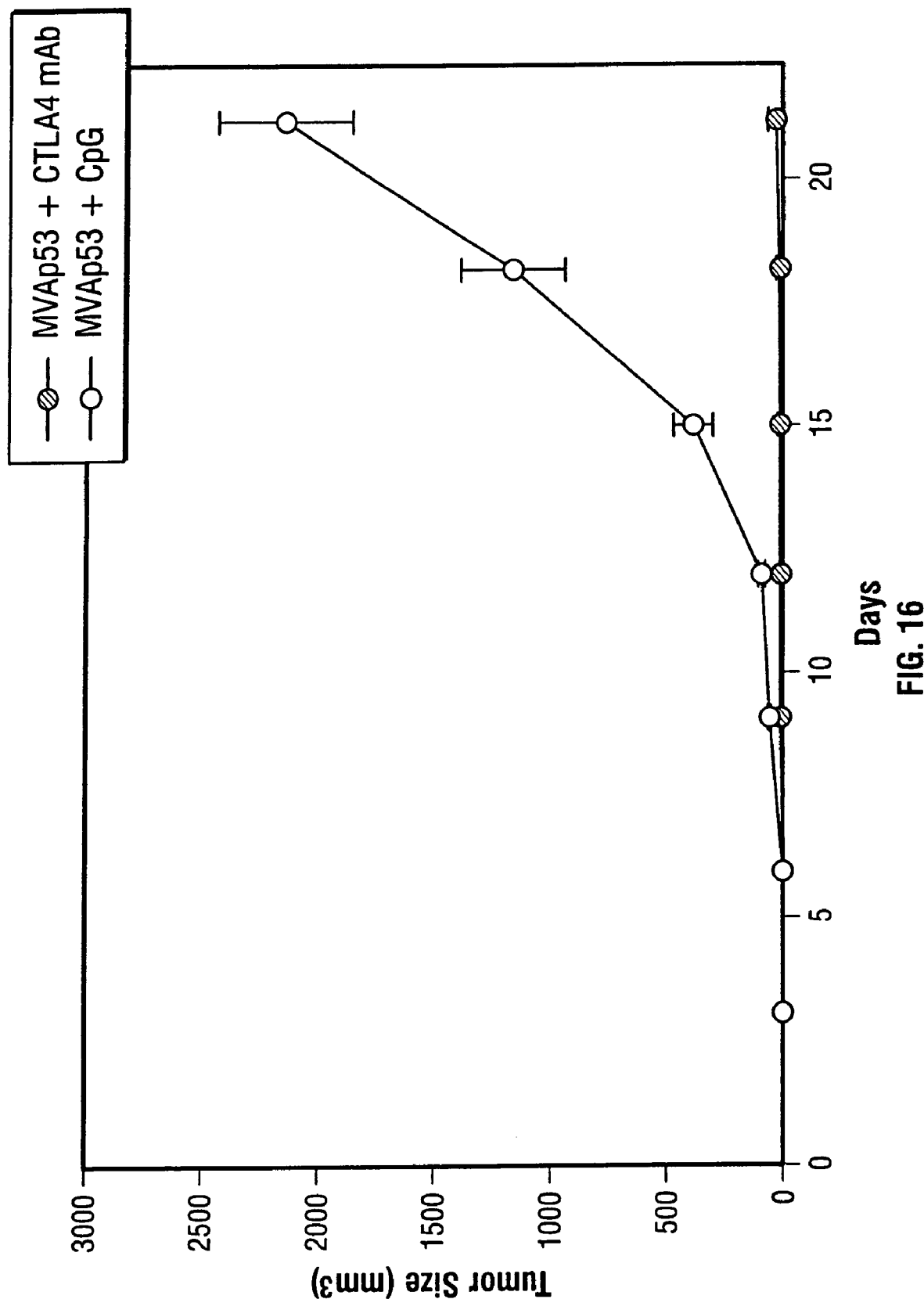
FIG. 16: Contribution of TLR 9 to the CpG ODN immunomodulator effect. TLR9$^{-/-}$ (p=0.0009, comparing anti-CTLA-4 mAb to CpG ODN group) mutant C57BL6 mice were injected s.c. with $1\times10^6$ MC-38 cells. Mice were treated with anti-CTLA-4 mAb (CTLA4 mAb) on days 4, 7, and 10 at 100, 50, and 50 μg/dose, respectively, or with 15 nmoles of CpG ODN on days 4, 9, and 14. On day 5, all mice were vaccinated i.p. with $5\times10^7$ pfu of rMVAmup53. Tumors were measured twice weekly in three dimensions with calipers. Each curve represents the mean and standard deviation of 8 mice.

The cell subset depletion studies suggest that the mechanism of immunomodulator activity of CTLA-4 blockade and CpG ODN is different. CpG ODN activity results from the stimulation of B-cells and plasmacytoid dendritic cells through an interaction with the TLR9 receptor (Chu 1997). CpG treatment causes a bias towards the $T_H1$ cytokine milieu and stimulation of NK cell proliferation, which may account for the partial effect on tumor rejection. To further delineate the divergent pathways involved in the CpG ODN and CTLA-4 blockade immunomodulator effects, MC-38 tumor challenge experiments were conducted in $TLR9^{-/-}$ mice. $TLR9^{-/-}$ mice fail to immunologically respond to CpG ODN administration (Hemmi 2000). As expected, $TLR9^{-/-}$ mice bearing early established MC-38 tumors failed to immunologically respond to CpG ODN and rMVAmup53 vaccination (FIG. 16). In contrast, inclusion of anti-CTLA-4 mAb with rMVAmup53 vaccination resulted in tumor rejection in $TLR9^{-/-}$ mice (p=0.0009) that was similar to that seen in wt C57BL/6 mice (FIG. 16, FIG. 7).

Contribution of IL-6

Figure 17:
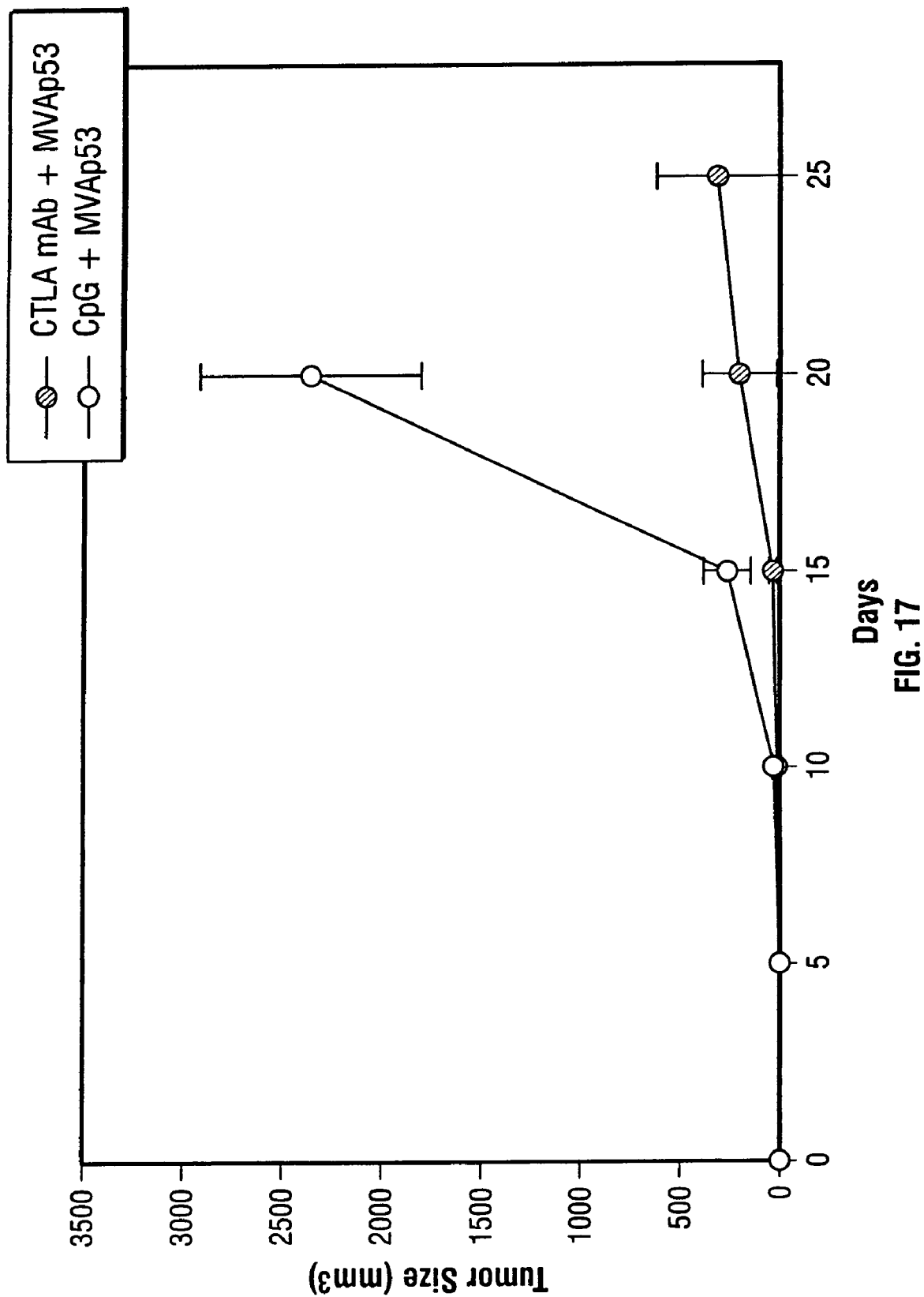
FIG. 17: Contribution of IL-6 to the CpG ODN immunomodulator effect. IL-6$^{-/-}$ (p=0.02, comparing anti-CTLA-4 mAb to CpG ODN group by Wilcoxon 2-sided RankSum Test) mutant C57BL/6 mice were injected s.c. with $1\times10^6$ MC-38 cells. Mice were treated with anti-CTLA-4 mAb (CTLA4 mAb) on days 4, 7, and 10 at 100, 50, and 50 μg/dose, respectively, or with 15 nmoles of CpG ODN on days 4, 9, and 14. On day 5, all mice were vaccinated i.p. with $5\times10^7$ pfu of rMVAmup53. Tumors were measured twice weekly in three dimensions with calipers. Each curve represents the mean and standard deviation of 8 mice.

Both CpG ODN and CTLA-4 blockade inhibit $CD25^+$ $CD4^+$ suppressor or regulatory T cells (Treg), and this effect may contribute to their immunomodulator activity in the described tumor models. Blocking CTLA-4 is thought to have a direct inhibitory affect on Tregs, most of which constitutively express CTLA-4 (Read 2000). In contrast, CpG ODN inhibits Treg activity through the secretion of IL-6 by DC (Pasare 2003). To evaluate the role of IL-6 on the CpG ODN and anti-CTLA-4 mAb immunomodulator effects, tumor challenge experiments were conducted in $IL-6^{-/-}$ mice. $IL-6^{-/-}$ mice bearing early established MC-38 tumors failed to immunologically respond to rMVAmup53 vaccination with CpG ODN by rejecting tumor (FIG. 17). This suggests that CpG ODN could be mediating its immunomodulator effects, at least in part, through the IL-6 dependent pathway of Treg cell inhibition. In contrast, anti-CTLA-4 mAB inclusion with rMVAmup53 vaccination resulted in tumor rejection in $IL-6^{-/-}$ mice (p=0.02) to an extent similar to that seen in wt C57BL/6 mice (FIG. 17, FIG. 7).

Example 5

Expression of Human p53 by rMVAhup53

Figure 18:
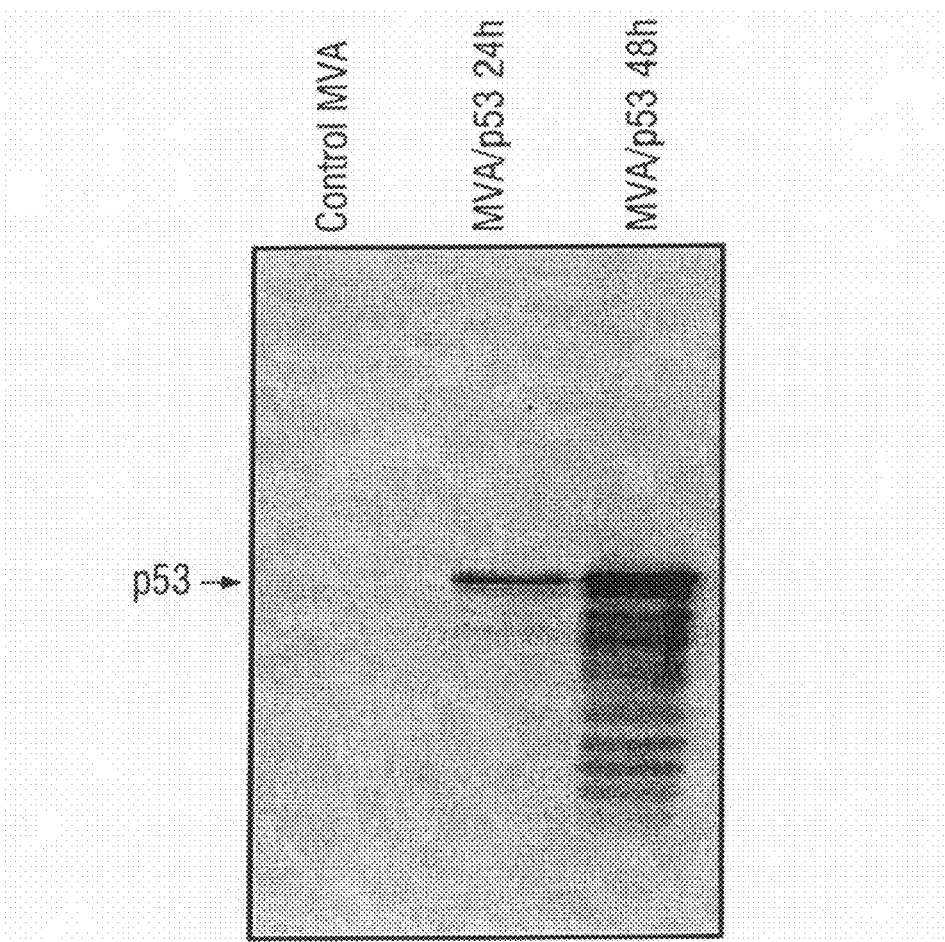
FIG. 18: Expression of hup53 by cells infected with rMVAhup53. BHK cells were injected with purified rMVAhup53 (MVA/p53). Expression of hup53 was measured at 24 and 48 hours. Cell lysates were subjected to SDS-PAGE and Western blotting. Lane 1: BHK cells injected with control MVA; Lane 2: BHK cells infected with rMVAhup53 for 24 hours; Lane 3: BHK cells infected with rMVAhup53 for 48 hours. All lanes were loaded with 20 μl of sample.

BHK cells were infected with purified rMVAhup53. Expression of hup53 was measured at 24 and 48 hours, and analyzed by Western blot and immunohistochemistry. The infected rMVAhup53 cells demonstrated vigorous expression of hup53 at both time periods (FIG. 18).

Example 6

In Vivo rMVAhu53 Tumor Challenge Experiments

Figure 19:
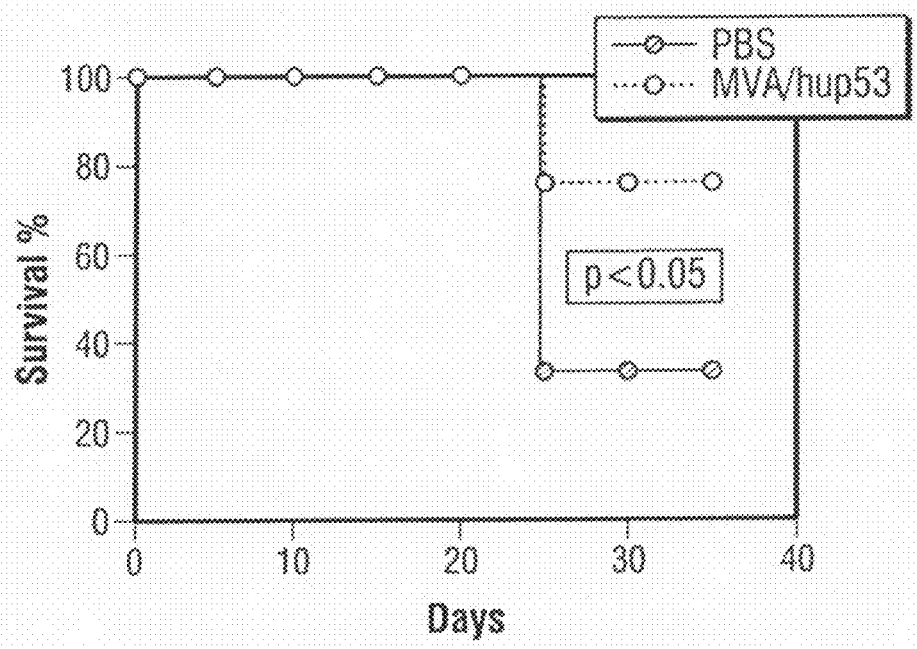
FIG. 19: Effect of vaccination with rMVAhup53 plus anti-CTLA-4 mAb and CpG ODN on established 4T1/hup53 tumors. Mice were injected s.c. with $5\times10^4$ 4T1/hup53, then vaccinated i.p. with $10^7$ pfu rMVAhup53 or PBS control on day 6. On day 16, mice received an rMVAhup53 or PBS booster injection, along with 15 nmole of CpG ODN and 50 μg of anti-CTLA-4 mAb. rMVAhup53 vaccinated mice displayed a significant improvement in survival (p<0.05, two sided T-test) compared to PBS controls.

Hupki mice, a novel murine knock-in model expressing human p53, were obtained from Dr. Monica Hollstein (DKFZ, Heidelberg, Germany) in the 129/Sv genetic background. The mice were backcrossed for 4 generations onto the Balb/c(H-$2^d$) background in order to take advantage of the knock-in transgene in a murine background where tumors and other reagents are readily available. The hupki mice on the Balb/c background were backcrossed to homozygosity as confirmed by PCR analysis, using a mating procedure that minimized inbreeding effects (data not shown). The 4T1 (H-$2^d$) murine breast carcinoma cell line was stably transfected with human p53, and hupki mice were s.c. injected with $5\times10^4$ 4T1/hup53 in the flank. Mice injected with 4T1/hup53 grow progressive tumors, and the majority succumb to these tumors by day 35. To test the efficacy of rMVAhup53, mice were vaccinated with $10^7$ pfu rMVAhup53 by i.p. injection on day 6 after 4T1/hup53 injection. Ten days later, the mice received an rMVAhup53 booster injection, along with CpG-ODN (15 nmole of ODN 1826) and anti-CTLA-4 mAb (50 µg/mouse). rMVAhup53 vaccination resulted in a statistically significant improvement in survival ($p<0.05$, two sided T-test) compared to PBS controls (FIG. 19).

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

Abbreviations used herein: GFP, green fluorescent protein; DC, dendritic cells; IFN-$\gamma^{KO}$, IFN-$\gamma$ knock out; MVA, modified vaccinia virus Ankara; rMVA, recombinant modified vaccinia virus Ankara; rAd-mup53, recombinant Adenovirus expressing murine wild type p53; hup53, wild type human p53; mup53, wild type murine p53; rMVAp53, recombinant MVA expressing p53; rMVAmup53, recombinant MVA expressing wild type murine p53; rMVAhup53, recombinant MVA expressing wild type human p53; rMVApp65, recombinant MVA expressing pp65; rVVmup53, recombinant vaccinia virus expressing murine wild type p53; rVVpp65, recombinant vaccinia virus expressing pp65; wtMVA, wild type MVA; WR, Western Reserve; i.p., intraperitoneal; s.c., subcutaneous; mAb, monoclonal antibody.

REFERENCES

1. Allred, D. C., O'Connell, P., Fuqua, S. A. 1993. Biomarkers in early breast neoplasia. J Cell Biochem Suppl 17G: 125-131.
2. Antoine, G., Scheiflinger, F., Dorner, F., Falkner, F. G. 1998. The complete genomic sequence of the modified vaccinia Ankara strain: comparison with other orthopoxviruses. Virology 244:365-396.
3. Baines, J., Celis, E. 2003. Immune-mediated tumor regression induced by CpG-containing oligodeoxynucleotides. Clin Cancer Res 9:2693-2700.
4. Ballas, Z. K., et al. 2001. Divergent therapeutic and immunologic effects of oligodeoxynucleotides with distinct CpG motifs. J Immunol 167:4878-4886.
5. Baral, R. N., et al. 2003. Immunostimulatory CpG oligonucleotides enhance the immune response of anti-idiotype vaccine that mimics carcinoembryonic antigen. Cancer Immunol Immunother 52:317-327.
6. Berns, E. M., et al. 1998. p53 protein accumulation predicts poor response to tamoxifen therapy of patients with recurrent breast cancer. J Clin Oncol 16:121-127.
7. Berns, E. M., et al. 2000. Complete sequencing of TP53 predicts poor response to systemic therapy of advanced breast cancer. Cancer Res 60:2155-2162.
8. Berson, J. F., et al. A seven-transmembrane domain receptor involved in fusion and entry of T-cell-tropic human immunodeficiency virus type 1 strain. J Virol 70:6288-6295.
9. Blanchard, T. J., Alcami, A, Andrea, P., Smith, G. L. 1998. Modified vaccinia virus Ankara undergoes limited replication in human cells and lacks several immunomodulatory proteins: implications for use as a human vaccine. J Gen Virol 79(Pt 5):1159-1167.
10. Bruggemann, M., et al. 1991. Human antibody production in transgenic mice: expression from 100 kb of the human IgH locus. Eur J Immunol 5:1323-1326.
11. Carpentier, A. F., Chen, L., Maltonti, F., Delattre, J. Y. 1999. Oligodeoxynucleotides containing CpG motifs can induce rejection of a neuroblastoma in mice. Cancer Res 59:5429-5432.
12. Carroll, M. W., Moss, B. 1997a. Host range and cytopathogenicity of the highly attenuated MVA strain of vaccinia virus: propagation and generation of recombinant viruses in a nonhuman mammalian cell line. Virology 238:198-211.
13. Carroll, M. W., et al. 1997b. Highly attenuated modified vaccinia virus Ankara (MVA) as an effective recombinant vector: a murine tumor model. Vaccine 15:387-394.
14. Chakrabarti, S., Brechling, K., Moss, B. 1985. Vaccinia virus expression vector: coexpression of beta-galactosidase provides visual screening of recombinant virus plaques. Mol Cell Biol 5:3403-3409.
15. Chu, R. S., et al. 1997. CpG oligodeoxynucleotides act as adjuvants that switch on T helper 1 (Th1) immunity. J Exp Med 186:1623-1631.
16. Collier, L. H. 1991. Safety of recombinant vaccinia vaccines. Lancet 337:1035-1036.
17. Davila, E., Celis, E. 2000. Repeated administration of cytosine-phosphorothiolated guanine-containing oligonucleotides together with peptide/protein immunization results in enhanced CTL responses with anti-tumor activity. J Immunol 165:539-547.
18. DeLeo, A. B., et al. 1977. Cell surface antigens of chemically induced sarcomas of the mouse. I. Murine leukemia virus-related antigens and alloantigens on cultured fibroblasts and sarcoma cells: description of a unique antigen on BALB/c Meth A sarcoma. J Exp Med 146:720-734.
19. Dialynas, D. P., et al. 1983. Characterization of the murine antigenic determinant, designated L3T4a, recognized by monoclonal antibody GK1.5: expression of L3T4a by functional T cell clones appears to correlate primarily with class II MHC antigen-reactivity. Immunol Rev 74:29-56.
20. Diamond, D. J., et al. 1997. Development of a candidate HLA A*0201 restricted peptide-based vaccine against human cytomegalovirus infection. Blood 90:1751-1767.
21. Drexler, I., et al. 1999. Modified vaccinia virus Ankara for delivery of human tyrosinase as melanoma-associated antigen: induction of tyrosi. Cancer Res 59:4955-4963.
22. Egen, J. G., Kuhns, M. S., Allison, J. P. 2002. CTLA-4: new insights into its biological function and use in tumor immunotherapy. Nat Immunol 3:611-618.
23. Eliyahu, D., et al. 1989. Wild-type p53 can inhibit oncogene-mediated focus formation. Proc Natl Acad Sci USA 86:8763-8767.
24. Elkhuizen, P. H., et al. 2000. High local recurrence risk after breast-conserving therapy in node-negative premenopausal breast cancer patients is greatly reduced by one course of perioperative chemotherapy: A European Organization for Research and Treatment of Cancer Breast Cancer Cooperative Group Study. J Clin Oncol 18:1075-1083.

25. Erdile, L. F., Smith, D. 2000. CD40 activation enhances the magnitude of cellular immune responses against p53 but not the avidity of the effectors. Cancer Immunol Immunother 49:410-416.

26. Espenschied, J., et al. 2003. CTLA-4 blockade enhances the therapeutic effect of an attenuated poxvirus vaccine targeting p53 in an established murine tumor model. J Immunol 170:3401-3407.

27. Finlay, C. A., et al. 1988. Activating mutations for transformation by p53 produce a gene product that forms an hsc70-p53 complex with an altered half-life. Mol Cell Biol 8:531-539.

28. Finlay, C. A., Hinds, P. W., Levine, A. J. 1989. The p53 proto-oncogene can act as a suppressor of transformation. Cell 57:1083-1093.

29. Foote, J., Winter, G. 1992. Antibody framework residues affecting the conformation of the hypervariable loops. J Mol Biol 224(2):487-499.

30. Gibson, L., et al. Human Cytomegalovirus Proteins pp65 and IE1 are Common Targets for CD8+ T cell Responses in Children with Congenital and Postnatal HCMV infection. J Immunol, in press.

31. Gurney, E. G., Harrison, R. O., Fenno, J. 1980. Monoclonal antibodies against simian virus 40 T antigens: evidence for distinct subclasses of large T antigen and for similarities among nonviral T antigens. J Virol 34:752-763.

32. Hainaut, P., Hollstein, M. 2000. p53 and human cancer: the first ten thousand mutations. Adv Cancer Res 77:81-137.

33. Halevy, O., Rodel, J., Peled, A., Oren, M. 1991. Frequent p53 mutations in chemically induced murine fibrosarcoma. Oncogene 6:1593-1600.

34. He, T. C., et al. 1998. A simplified system for generating recombinant adenoviruses. Proc Natl Acad Sci USA 95:2509-2514.

35. Heckelsmiller, K., et al. 2002. Combined dendritic cell- and CpG oligonucleotide-based immune therapy cures large murine tumors that resist chemotherapy. Eur J Immunol 32:3235-3245.

36. Hemmi, H., et al. 2000. A Toll-like receptor recognizes bacterial DNA. Nature 408:740-745.

37. Hernandez, J., Lee, P. P., Davis, M. M., Sherman, L. A. 2000. The use of HLA A2.1/p53 peptide tetramers to visualize the impact of self tolerance on the TCR repertoire. J Immunol 164:596-602.

38. Hilburger, R. M., Abrams, S. I. 2001. Characterization of CD8+ cytotoxic T lymphocyte/tumor cell interactions reflecting recognition of an endogenously expressed murine wild-type p53 determinant. Cancer Immunol Immunother 49:603-612.

39. Hurwitz, A. A., Yu, T. F., Leach, D. R., Allison, J. P. 1998. CTLA-4 blockade synergizes with tumor-derived granulocyte-macrophage colony-stimulating factor for treatment of an experimental mammary carcinoma. Proc Natl Acad Sci USA 95:10067-10071.

40. Hurwitz, A. A., et al. 2000. Combination immunotherapy of primary prostate cancer in a transgenic mouse model using CTLA-4 blockade. Cancer Res 60:2444-2448.

41. Jones, P. T., Dear, P. H., Foote, J., Neuberger, M. S., Winter, G. 1986. Replacing complementarity-determining regions in a human antibody with those from a mouse. Nature 321 (6069):522-525.

42. Kawarada, Y., et al. 2001. NK– and CD8(+) T cell-mediated eradication of established tumors by peritumoral injection of CpG-containing oligodeoxynucleotides. J Immunol 167:5247-5253.

43. Kim, T. Y., et al. 2002. Both E7 and CpG-oligodeoxynucleotide are required for protective immunity against challenge with human papillomavirus 16 (E6/E7) immortalized tumor cells: involvement of CD4+ and CD8+ T cells in protection. Cancer Res 62:7234-7240.

44. Kit, S., Dubbs, D. R., DeTorres, R. A., Melnick, J. L. 1965. Enhanced thymidine kinase activity following infection of green monkey kidney cells by simian adenoviruses, simian papovavirus SV40, and an adenovirus-SV40 "hybrid". Virology 27:453-457.

45. Koo, G. C., Peppard, J. R. 1984. Establishment of monoclonal anti-Nk-1.1 antibody. Hybridoma 3:301-303.

46. Krieg, A. M. 2002. CpG motifs in bacterial DNA and their immune effects. Annu Rev Immunol 20:709-760.

47. Krieg, A. M. 2003. CpG motifs: the active ingredient in bacterial extracts? Nat Med 9:831-835.

48. Krummel, M. F., Allison, J. P. 1995. CD28 and CTLA-4 have opposing effects on the response of T cells to stimulation. J Exp Med 182:459-465.

49. Levine, A. J. 1997. p53, the cellular gatekeeper for growth and division. Cell 88:323-331.

50. Low, N. M., Holliger, P. H., Winter, G. 1986. Mimicking somatic hypermutation: affinity maturation. J Mol Biol 260:359-368.

51. Macpherson, I., Stoker, M. 1962. Polyoma transformation of hamster cell clones—an investigation of genetic factors affecting cell competence. Virology 16:147-151.

52. Mayordomo, J. I., et al. 1996. Therapy of murine tumors with p53 wild-type and mutant sequence peptide-based vaccines. J Exp Med 183:1357-1365.

53. Mayr, A., et al. 1978. [The smallpox vaccination strain MVA: marker, genetic structure, experience gained with the parenteral vaccination and behavior in organisms with a debilitated defense mechanism (author's transl)]. Zentralbl Bakteriol [B] 167:375-390.

54. Mayr, A. 1999. [Historical review of smallpox, the eradication of smallpox and the attenuated smallpox MVA vaccine]. Berlin Munch Tierarztl Wochenschr 112:322-328.

55. Mendez, M. J., et al. 1997. Functional transplant of megabase human immunoglobulin loci recapitulates human antibody response in mice. Nat Genet 2:146-156.

56. Meyer, H., Sutter, G., Mayr, A. 1991. Mapping of deletions in the genome of the highly attenuated vaccinia virus MVA and their influence on virulence. Gen Virol 72(Pt 5):1031-1038.

57. Miconnet, I., et al. 2001. Cancer vaccine design: a novel bacterial adjuvant for peptide-specific CTL induction. J Immunol 166:4612-4619.

58. Millikan, R., et al. 1995. p53 mutations in benign breast tissue. J Clin Oncol 13:2293-2300.

59. Moldoveanu, Z., Love-Homan, L., Huang, W. Q., Krieg, A. M. 1998. CpG DNA, a novel immune enhancer for systemic and mucosal immunization with influenza virus. Vaccine 16:1216-1224.

60. Mulryan, K., et al. Attenuated recombinant vaccinia virus expressing oncofetal antigen (tumor-associated antigen) 5T4 induces active therapy of established tumors. Mol Cancer Ther 1:1129-1137.

61. Noguchi, Y., Richards, E. C., Chen, Y. T., Old, L. J. 1995. Influence of interleukin 12 on p53 peptide vaccination against established Meth A sarcoma. Proc Natl Acad Sci USA 92:2219-2223.

62. Norbury, C. C., et al. 2002. Visualizing priming of virus-specific CD8+ cells by infected dendritic cells in vivo. Nat Immunol 3:265-271.

63. Offringa, R., et al. p53: a potential target antigen for immunotherapy of cancer. Ann N Y Acad Sci 910:223-233.

64. Ourmanov, I., et al. 2000. Comparative efficacy of recombinant modified vaccinia virus Ankara expressing simian immunodeficiency virus (SIV) Gag-Pol and/or Env in macaques challenged with pathogenic SIV. J Virol 74:2740-2751.

65. Pasare, C., Medzhitov, R. 2003. Toll pathway-dependent blockade of CD4+ CD25+ T-cell mediated suppression by dendritic cells. Science 299:1033-1036.

66. Pratap, R., Shousha, S. 1998. Breast carcinoma in women under the age of 50: relationship between p53 immunostaining, tumour grade, and axillary lymph node status. Breast Cancer Res Treat 49:35-39.

67. Querzoli, P., et al. 1998. Modulation of biomarkers in minimal breast carcinoma: a model for human breast carcinoma progression. Cancer 83:89-97.

68. Querzoli, P., et al. 2001. Biophenotypes and survival of BRCA1 and TP53 deleted breast cancer in young women. Breast Cancer Res Treat 66:135-142.

69. Ramirez, J. C., Gherardi, M. M., Rodriguez, D., Esteban, M. 2000a. Attenuated modified vaccinia virus Ankara can be used as an immunizing agent under conditions of preexisting immunity to the vector. J Virol 74:7651-7655.

70. Ramirez, J. C., Gherardi, M. M., Esteban, M. 2000b. Biology of attenuated modified vaccinia virus Ankara recombinant vector in mice: virus fate and activation. J Virol 74:923-933.

71. Read, S., Malmstrom, V., Powrie, F. 2000. Cytotoxic T lymphocyte-associated antigen 4 plays an essential role in the function of CD25(+)CD4(+) regulatory cells that control intestinal inflammation. J Exp Med 192:295-302.

72. Redfield, R. R., et al. 1987. Disseminated vaccinia in a military recruit with human immunodeficiency virus (HIV) disease. N Engl J Med 316:673-676.

73. Reich, N. C., Levine, A. J. 1984. Growth regulation of a cellular tumour antigen, p53, in nontransformed cells. Nature 308:199-201.

74. Rosales, C., et al. A recombinant vaccinia virus containing the papilloma E2 protein promotes tumor regression by stimulating macrophage antibody-dependent cytotoxicity. Cancer Immunol Immunother 49:347-360.

75. Rosenberg, S. A. 2001. Progress in human tumour immunology and immunotherapy. Nature 411:380-384.

76. Sandler, A. D., et al. 2003. CpG oligonucleotides enhance the tumor antigen-specific immune response of a granulocyte macrophage colony-stimulating factor-based vaccine strategy in neuroblastoma. Cancer Res 63:394-399.

77. Schmid, P., Lorenz, A., Hameister, H., Montenarh, M. 1991. Expression of p53 during mouse embryogenesis. Development 113:857-865.

78. Selvanayagam, C. S., Davis, C. M., Cornforth, M. N., Ullrich, R. L. 1995. Latent expression of p53 mutations and radiation-induced mammary cancer. Cancer Res 55:3310-3317.

79. Sharma, S., et al. 2003. Intra-tumoral injection of CpG results in the inhibition of tumor growth in murine Colon-26 and B-16 tumors. Biotechnol Lett 25:149-153.

80. Sirvent, J. J., Fortuna-Mar, A., Olona, M., Orti, A. 2001. Prognostic value of p53 protein expression and clinicopathological factors in infiltrating ductal carcinoma of the breast. Histol Histopathol 16:99-106.

81. Stern, B. V., Boehm, B. O., Tary-Lehmann, M. 2002. Vaccination with tumor peptide in CpG adjuvant protects via IFN-gamma-dependent CD4 cell immunity. J Immunol 168: 6099-6105.

82. Stittelaar, K. J., et al. 2001. Safety of a modified vaccinia virus Ankara (MVA) in immune-suppressed macaques. Vaccine 19:3700-3709.

83. Sukumar, S., McKenzie, K., Chen, Y. 1995. Animal models for breast cancer. Mutat Res 333:37-44.

84. Sutter, G., Moss, B. 1992. Nonreplicating vaccinia virus vector efficiently expresses recombinant genes. Proc Natl Acad Sci USA 89:10847-10851.

85. Tan, M. H., Holyoke, E. D., Goldrosen, M. H. 1976. Murine colon adenocarcinomas: methods for selective culture in vitro. J Natl Cancer Inst 56:871-873.

86. Theobald, M., et al. 1997. Tolerance to p53 by A2.1-restricted cytotoxic T lymphocytes. J Exp Med 185:833-841.

87. Turner, B. C., et al. 2000. Mutant p53 protein overexpression in women with ipsilateral breast tumor recurrence following lumpectomy and radiation therapy. Cancer 88:1091-1098.

88. van Elsas, A., Hurwitz, A. A., Allison, J. P. 1999. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med 190:355-366.

89. Vierboom, M. P., et al. 2000a. High steady-state levels of p53 are not a prerequisite for tumor eradication by wild-type p53-specific cytotoxic T lymphocytes. Cancer Res 60:5508-5513.

90. Vierboom, M. P., et al. 2000b. Cyclophosphamide enhances anti-tumor effect of wild-type p53-specific CTL. Int J Cancer 87:253-260.

91. Vierboom, M. P., et al. 1997. Tumor eradication by wild-type p53-specific cytotoxic T lymphocytes. J Exp Med 186:695-704.

92. Weiner, G. J., et al. 1997. Immunostimulatory oligodeoxynucleotides containing the CpG motif are effective as immune adjuvants in tumor antigen immunization. Proc Natl Acad Sci USA 94:10833-10837.

93. Wiedenfeld, E. A., Fernandez-Vina, M., Berzofsky, J. A., Carbone, D. P. 1994. Evidence for selection against human lung cancers bearing p53 missense mutations which occur within the HLA A*0201 peptide consensus motif. Cancer Res 54:1175-1177.

94. Winter, G., Griffiths, A. D., Hawkins, R. E., Hoogenboom, H. R. 1994. Making antibodies by phage display technology. Annu Rev Immunol 12:433-455.

95. Zambetti, G. P., Levine, A. J. 1993. A comparison of the biological activities of wild-type and mutant p53. FASEB J 7:855-865.

96. Zellars, R. C., et al. 2000. Prognostic value of p53 for local failure in mastectomy-treated breast cancer patients. J Clin Oncol 18:1906-1913.

What is claimed is:

1. A method of generating a p53 specific cytotoxic T lymphocyte (CTL) response in a mammal overexpressing mutant p53 comprising administering a composition comprising recombinant MVA virus containing a nucleic acid sequence encoding wild-type human p53, wherein said nucleic acid sequence comprises the nucleotide sequence set forth in SEQ ID NO:2 and wherein said recombinant MVA virus expresses the encoded wild-type human p53 protein.

2. The method of claim 1, further comprising administering a CTLA-4 blocking agent and a CpG oligodeoxynucleotide.

3. The method of claim 2, wherein said CTLA-4 blocking agent is an antibody.

4. The method of claim 3, wherein said antibody is a monoclonal antibody.

5. The method of claim 2, wherein administration of said CTLA-4 blocking agent and CpG oligodeoxynucleotide occurs simultaneously with administration of the composition comprising recombinant MVA virus.

6. The method of claim 2, wherein administration of said CTLA-4 blocking agent and CpG oligodeoxynucleotide is repeated one or more times.

* * * * *